US011322255B2

(12) United States Patent
Neumann

(10) Patent No.: US 11,322,255 B2
(45) Date of Patent: May 3, 2022

(54) METHODS AND SYSTEMS FOR SELF-FULFILLMENT OF AN ALIMENTARY INSTRUCTION SET BASED ON VIBRANT CONSTITUTIONAL GUIDANCE

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 124 days.

(21) Appl. No.: 16/781,601

(22) Filed: Feb. 4, 2020

(65) Prior Publication Data
US 2020/0321114 A1 Oct. 8, 2020

Related U.S. Application Data

(63) Continuation-in-part of application No. 16/729,330, filed on Dec. 28, 2019, which is a continuation of
(Continued)

(51) Int. Cl.
*G16H 50/00* (2018.01)
*G16H 50/20* (2018.01)
(Continued)

(52) U.S. Cl.
CPC .............. *G16H 50/00* (2018.01); *G06N 20/00* (2019.01); *G06N 5/022* (2013.01); *G06N 20/10* (2019.01);
(Continued)

(58) Field of Classification Search
CPC ........ G16H 50/00; G16H 50/20; G16H 50/30; G16H 50/50; G16H 50/70; G06N 20/00; G06N 20/10; G06N 20/20; G06N 5/022
(Continued)

(56) References Cited

U.S. PATENT DOCUMENTS

| 7,894,849 B2 | 2/2011 | Kass et al. |
| 8,409,104 B2 | 4/2013 | Cobain |

(Continued)

FOREIGN PATENT DOCUMENTS

WO 2018020239 2/2018

OTHER PUBLICATIONS

Westerman, et al.; Longitudinal analysis of biomarker data from a personalized nutrition platform in healthy subjects; Scientific Reports; Oct. 2, 2018; https://www.nature.com/articles/s41598-018-33008-7.pdf.
(Continued)

*Primary Examiner* — Daniel H Pan
(74) *Attorney, Agent, or Firm* — Caldwell Intellectual Property Law; Keegan Caldwell; Katherine Rubino

(57) ABSTRACT

A system for self-fulfillment of an alimentary instruction set based on vibrant constitutional guidance using artificial intelligence. The system includes a computing device designed and configured to receive training data. The computing device is further configured to record at least a biological extraction from a user and generate a diagnostic output. The computing device is further configured to generate a self-fulfillment instruction set utilizing the diagnostic output. The computing device is further configured to receive a user entry containing a completed alimentary self-fulfillment action. The computing device is further configured to update the self-fulfillment instruction set as a function of an alimentary self-fulfillment action.

18 Claims, 28 Drawing Sheets

Related U.S. Application Data application No. 16/375,303, filed on Apr. 4, 2019, now Pat. No. 10,553,316.

(51) Int. Cl.
    *G16H 50/30* (2018.01)
    *G16H 50/50* (2018.01)
    *G06N 20/00* (2019.01)
    *G06N 20/10* (2019.01)
    *G06N 20/20* (2019.01)
    *G06N 5/02* (2006.01)

(52) U.S. Cl.
    CPC .............. *G06N 20/20* (2019.01); *G16H 50/20* (2018.01); *G16H 50/30* (2018.01); *G16H 50/50* (2018.01)

(58) Field of Classification Search
    USPC ................. 712/218–219, 225; 600/300, 301; 706/12, 25, 26, 27
    See application file for complete search history.

(56) References Cited

U.S. PATENT DOCUMENTS

| | | | |
|---|---|---|---|
| 8,532,938 B2 | 9/2013 | Jung et al. | |
| 8,737,971 B2 | 5/2014 | Van Rooyen | |
| 8,762,167 B2 | 6/2014 | Blander et al. | |
| 8,822,225 B2 | 9/2014 | Hu et al. | |
| 9,132,219 B2 | 9/2015 | Akonur et al. | |
| 9,183,757 B2 | 11/2015 | Yamada et al. | |
| 9,589,480 B2 | 3/2017 | Ellis | |
| 9,758,839 B2 | 9/2017 | Apte et al. | |
| 9,838,508 B2 | 12/2017 | Salem | |
| 10,102,345 B2 | 10/2018 | Yanev et al. | |
| 10,127,361 B2 | 11/2018 | Hyde et al. | |
| 10,133,849 B2 | 11/2018 | Yanev et al. | |
| 2005/0240434 A1* | 10/2005 | Wooten ................. G16H 20/60 705/2 |
| 2008/0177149 A1 | 7/2008 | Weinert et al. | |
| 2008/0195594 A1 | 8/2008 | Gerjets et al. | |
| 2008/0306763 A1 | 12/2008 | James | |
| 2010/0098809 A1 | 4/2010 | Bender et al. | |
| 2013/0079612 A1 | 3/2013 | Hunt et al. | |
| 2013/0138447 A1 | 5/2013 | Nova et al. | |
| 2015/0012295 A1 | 1/2015 | Mahoney | |
| 2016/0042152 A1 | 2/2016 | Oran | |
| 2017/0169185 A1* | 6/2017 | Weng .................... G16H 20/17 |
| 2017/0216518 A1 | 8/2017 | Davis et al. | |
| 2017/0225447 A1* | 8/2017 | Varadan ............. H01L 51/0566 |
| 2017/0235906 A1* | 8/2017 | Dorris .................... G16H 20/30 705/2 |
| 2017/0277841 A1* | 9/2017 | Shankar ................ G16H 50/20 |
| 2017/0300647 A1* | 10/2017 | Goldberg ............... G16H 50/20 |
| 2018/0032698 A1 | 2/2018 | Lau et al. | |

OTHER PUBLICATIONS

Inside Tracker; Who we are; file:///C:/Users/LindseyPowell/Downloads/InsideTracker's%20expert%20team_%20scientists . . . pdf.

Bald, Eric; The A.I. Diet; https://www.weizmann-usa.org/news-media/in-the-news/the-ai-diet.

Ramachandran, Swaroopini; Mar. 15, 2019; The algorithm to a perfect diet—AI has answers; http://peasonmoss.com/2019/03/15/the-algorithm-to-a-perfect-diet-ai-has-answers/.

VK, Anirudh; 5 AI-Powered fitness startups in India who are using data science to promote healthy lifestyle; https://www.analyticsindiamag.com/5-ai-powered-fitness-startups-in-india-who-are-using-data-science-to-promote-healthy-lifestyle/.

* cited by examiner

METHODS AND SYSTEMS FOR SELF-FULFILLMENT OF AN ALIMENTARY INSTRUCTION SET BASED ON VIBRANT CONSTITUTIONAL GUIDANCE

RELATED APPLICATION DATA

This application is a continuation-in-part of Ser. No. 16/729,330 filed on Dec. 28, 2019 and entitled "SYSTEMS AND METHODS FOR GENERATING ALIMENTARY INSTRUCTION SETS BASED ON VIBRANT CONSTITUTIONAL GUIDANCE," which is a continuation of U.S. patent application Ser. No. 16/375,303, filed on Apr. 4, 2019 and entitled "SYSTEMS AND METHODS FOR GENERATING ALIMENTARY INSTRUCTION SETS BASED ON VIBRANT CONSTITUTIONAL GUIDANCE," which is hereby incorporated by reference herein in its entirety.

FIELD OF THE INVENTION

The present invention generally relates to the field of artificial intelligence. In particular, the present invention is directed to methods and systems for self-fulfillment of an alimentary instruction set.

BACKGROUND

Generating alimentary instructions is a complex process hampered by the complexity and amount of data involved. Effective and accurate analysis of data to produce practical and useful instruction sets is challenging. Current solutions fail to account for the multivariate complexity in producing meaningful instruction sets.

SUMMARY OF THE DISCLOSURE

These and other aspects and features of non-limiting embodiments of the present invention will become apparent to those skilled in the art upon review of the following description of specific non-limiting embodiments of the invention in conjunction with the accompanying drawings.

In an aspect, a system for self-fulfillment of an alimentary instruction set based on vibrant constitutional guidance. The system includes a computing device, the computing device including a diagnostic engine operating on the computing device, the diagnostic engine configured to receive training data, wherein receiving the training data further comprises receiving a first training set including a plurality of first data entries, each first data entry of the plurality of first data entries including at least an element of physiological state data and at least a correlated first prognostic label; and receiving a second training set including a plurality of second data entries, each second data entry of the plurality of second data entries including at least a second prognostic label and at least a correlated ameliorative process label. The computing device is further configured to record at least a biological extraction from a user wherein the at least a biological extraction contains at least an element of physiological state data. The computing device is further configured to generate a diagnostic output based on the at least a biological extraction and the training data, wherein generating further comprises performing at least a machine-learning algorithm as a function of the training data and the at least a biological extraction. The computing device includes a fulfillment module operating on the at least a server the fulfillment module designed and configured to generate a self-fulfillment instruction set utilizing the diagnostic output wherein the self-fulfillment instruction set identifies a self-fulfillment action. The computing device is further configured to receive at least a user entry containing a completed alimentary self-fulfillment action. The computing device is further configured update the self-fulfillment instruction set as a function of the alimentary self-fulfillment action.

In an aspect, a method of self-fulfillment of an alimentary instruction set based on vibrant constitutional guidance. The method includes receiving by a computing device training data, wherein receiving the training data further comprises receiving a first training set including a plurality of first data entries, each first data entry of the plurality of first data entries including at least an element of physiological state data and at least a correlated first prognostic label; and receiving a second training set including a plurality of second data entries, each second data entry of the plurality of second data entries including at least a second prognostic label and at least a correlated ameliorative process label. The method includes recording by the computing device at least a biological extraction from a user wherein the at least a biological extraction contains at least an element of physiological state data. The method includes generating by the computing device a diagnostic output based on the at least a biological extraction and the training data, wherein generating further comprises performing at least a machine-learning algorithm as a function of the training data and the at least a biological extraction. The method includes generating by the computing device a self-fulfillment instruction set utilizing the diagnostic output wherein the self-fulfillment instruction set identifies a self-fulfillment action. The method includes receiving by the computing device at least a user entry containing a completed alimentary self-fulfillment action. The method includes updating by the computing device the self-fulfillment instruction set as a function of the alimentary self-fulfillment action.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to methods and systems for self-fulfillment of an alimentary instruction set based on vibrant constitutional guidance. In an embodiment, methods and systems are provided for self-fulfillment of an alimentary instruction set. User entries containing actions a user engaged in to self-fulfill an alimentary instruction set may be matched and utilized to update alimentary instruction sets. Alimentary instruction sets may be generated from biological extractions received from a user. Alimentary instruction sets may be updated based on machine learning processes including both supersized and unsupervised processes.

Figure 1:
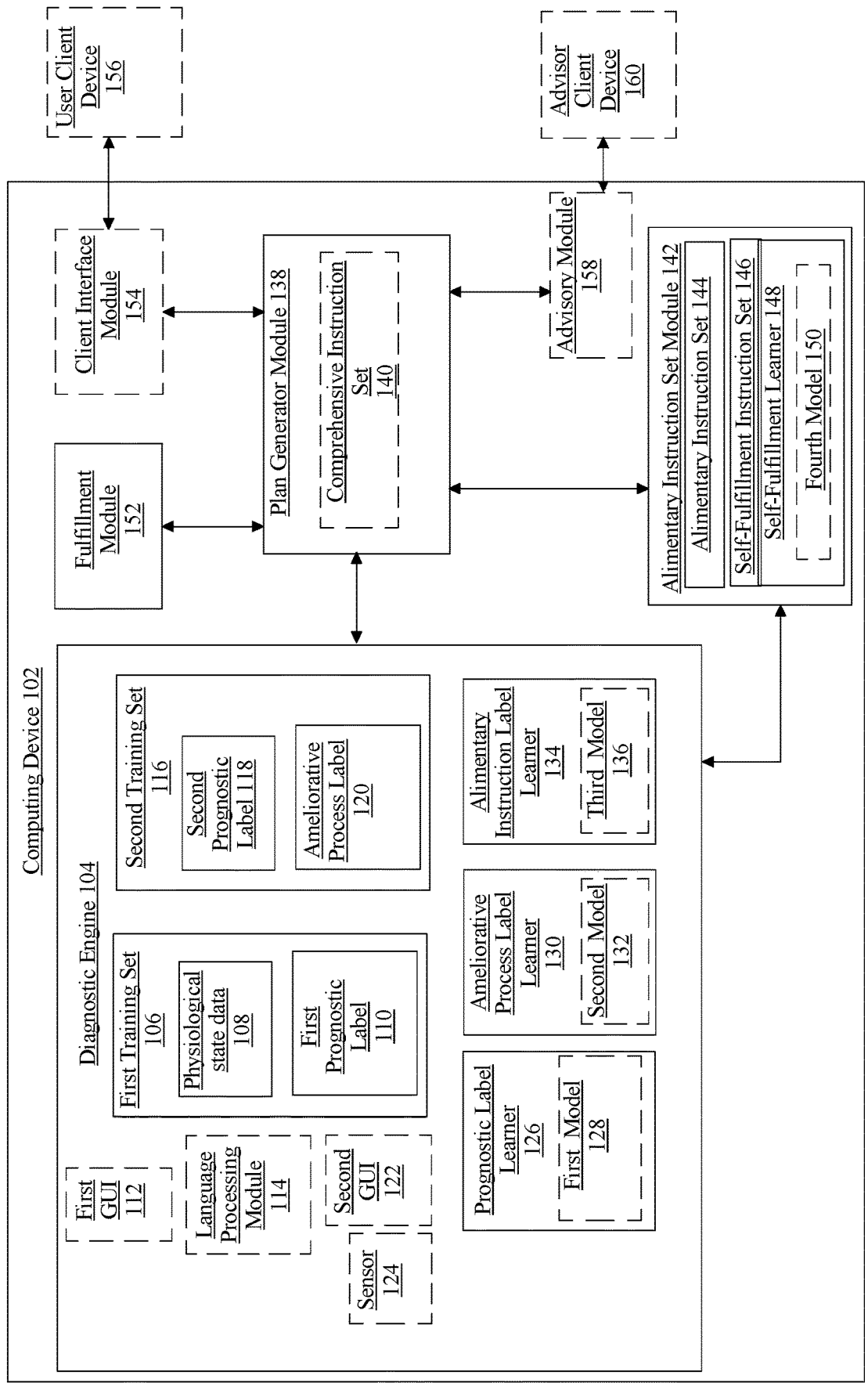
FIG. 1 is a block diagram illustrating an exemplary embodiment of a system for self-fulfillment of an alimentary instruction set based on vibrant constitutional guidance.

Turning now to FIG. 1, a system 100 for self-fulfillment of an alimentary instruction set based on vibrant constitutional guidance is illustrated. System 100 includes a computing device 102. A computing device 102 may include any computing device as described herein, including without limitation a microcontroller, microprocessor, digital signal processor (DSP) and/or system on a chip (SoC) as described herein A computing device 102 may be housed with, may be incorporated in, or may incorporate one or more sensors of at least a sensor. Computing device may include, be included in, and/or communicate with a mobile device such as a mobile telephone or smartphone. A computing device 102 may include a single computing device operating independently, or may include two or more computing device operating in concert, in parallel, sequentially or the like; two or more computing devices may be included together in a single computing device or in two or more computing devices. A computing device 102 with one or more additional devices as described below in further detail via a network interface device. Network interface device may be utilized for connecting a computing device 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. A computing device 102 may include but is not limited to, for example, a computing device 102 or cluster of computing devices in a first location and a second computing device or cluster of computing devices in a second location. A computing device 102 may include one or more computing devices dedicated to data storage, security, distribution of traffic for load balancing, and the like. A computing device 102 may distribute one or more computing tasks as described below across a plurality of computing devices of computing device, which may operate in parallel, in series, redundantly, or in any other manner used for distribution of tasks or memory between computing devices. A computing device 102 may be implemented using a "shared nothing" architecture in which data is cached at the worker, in an embodiment, this may enable scalability of system 100 and/or computing device.

Still referring to FIG. 1, system 100 includes a diagnostic engine 104 operating on the a computing device 102, wherein the diagnostic engine 104 configured to receive a first training set including a plurality of first data entries, each first data entry of the plurality of first data entries including at least an element of physiological state data and at least a correlated first prognostic label; receive a second training set including a plurality of second data entries, each second data entry of the plurality of second data entries including at least a second prognostic label and at least a correlated ameliorative process label; receive at least a biological extraction from a user; and generate a diagnostic output based on the at least a biological extraction, the diagnostic output including at least a prognostic label and at least an ameliorative process label using the first training set, the second training set, and the at least a biological extraction. A computing device 102, diagnostic engine 104, and/or one or more modules operating thereon may be designed and/or configured to perform any method, method step, or sequence of method steps in any embodiment described in this disclosure, in any order and with any degree of repetition. For instance, a computing device 102 and/or diagnostic engine 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device 102 and/or diagnostic engine 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, diagnostic engine 104 may be designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, diagnostic engine 104 may be configured to receive a first training set 106 including a plurality of first data entries, each first data entry of the first training set 106 including at least an element of physiological state data 108 and at least a correlated first prognostic label 110. At least an element of physiological state data 108 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 108 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 108 may include, without limitation, immune function data such as Interleukine-6 (IL-6), TNF-alpha, systemic inflammatory cytokines, and the like.

Continuing to refer to FIG. 1, physiological state data 108 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 108 may include measures of glucose metabolism such as fasting glucose levels and/or hemoglobin A1-C (HbA1c) levels. Physiological state data 108 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 108 may include measures of estimated glomerular filtration rate (eGFR). Physiological state data 108 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 108 may include antinuclear antibody levels. Physiological state data 108 may include aluminum levels. Physiological state data 108 may include arsenic levels. Physiological state data 108 may include levels of fibrinogen, plasma cystatin C, and/or brain natriuretic peptide.

Continuing to refer to FIG. 1, physiological state data 108 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 108 may include a measurement blood pressure, including without limitation systolic and diastolic blood pressure. Physiological state data 108 may include a measure of waist circumference. Physiological state data 108 may include body mass index (BMI). Physiological state data 108 may include one or more measures of bone mass and/or density such as dual-energy x-ray absorptiometry. Physiological state data 108 may include one or more measures of muscle mass. Physiological state data 108 may include one or more measures of physical capability such as without limitation measures of grip strength, evaluations of standing balance, evaluations of gait speed, pegboard tests, timed up and go tests, and/or chair rising tests.

Still viewing FIG. 1, physiological state data 108 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 204 may include one or more measures of psychological function or state, such as without limitation clinical interviews, assessments of intellectual functioning and/or intelligence quotient (IQ) tests, personality assessments, and/or behavioral assessments. Physiological state data 204 may include one or more psychological self-assessments, which may include any self-administered and/or automatedly computer-administered assessments, whether administered within system 100 and/or via a third-party service or platform.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

With continued reference to FIG. 1, physiological state data 108 may include one or more evaluations of sensory ability, including measures of audition, vision, olfaction, gustation, vestibular function and pain. Physiological state data 108 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 108 may include proteomic data, which as used herein, is data describing all proteins produced and/or modified by an organism, colony of organisms, or system of organisms, and/or a subset thereof. Physiological state data 108 may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 108 of a person, and/or on prognostic labels and/or ameliorative processes as described in further detail below. Physiological state data 108 may include any physiological state data 108, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a computing device 102 may present to user a set of assessment questions designed or intended to evaluate a current state of mind of the user, a current psychological state of the user, a personality trait of the user, or the like; at least a computing device 102 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or auto-immune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *Cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies'* and *Methanosphaera stadtmanae*. Fungi may include *Candida* species and *Malassezia* species. Viruses may include bacteriophages. *Microbiome* species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's *muciniphila, Anaerotruncus colihominis*, bacteriology, *Bacteroides vulgates', Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, examples of physiological state data 108 described in this disclosure are presented for illustrative purposes only and are not meant to be exhaustive. Persons skilled in the art, upon reviewing the entirety of this disclosure, will be aware of various additional examples of physiological state data 108 that may be used consistently with descriptions of systems and methods as provided in this disclosure.

Continuing to refer to FIG. 1, each element of first training set 106 includes at least a first prognostic label 110. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or healthy aging. At least a prognostic label may be associated with a physical and/or somatic condition, a mental condition such as a mental illness, neurosis, or the like, or any other condition affecting human health that may be associated with one or more elements of physiological state data 108 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, *Leishmania*, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrine disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 1, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 1, in each first data element of first training set 106, at least a first prognostic label 110 of the data element is correlated with at least an element of physiological state data 108 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the first training set 106. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 106 and/or first data element consistently with this disclosure.

In an embodiment, and still referring to FIG. 1, diagnostic engine 104 may be designed and configured to associate at least an element of physiological state data 108 with at least a category from a list of significant categories of physiological state data 108. Significant categories of physiological state data 108 may include labels and/or descriptors describing types of physiological state data 108 that are identified as being of high relevance in identifying prognostic labels. As a non-limiting example, one or more categories may identify significant categories of physiological state data 108 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, diagnostic engine 104 may receive the list of significant categories according to any suitable process; for instance, and without limitation, diagnostic engine 104 may receive the list of significant categories from at least an expert. In an embodiment, diagnostic engine 104 and/or a user device connected to diagnostic engine 104 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like Still referring to FIG. 1, diagnostic engine 104 may receive the list of significant categories according to any suitable process; for instance, and without limitation, diagnostic engine 104 may receive the list of significant categories from at least an expert. In an embodiment, diagnostic engine 104 and/or a user device connected to diagnostic engine 104 may provide a graphical user interface 112, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 112 or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface 112 may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like With continued reference to FIG. 1, data information describing significant categories of physiological data, relationships of such categories to prognostic labels, and/or significant categories of prognostic labels may alternatively or additionally be extracted from one or more documents using a language processing module 114. Language processing module 114 may include any hardware and/or software module. Language processing module 114 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning; and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains" for example for use as a Markov chain or Hidden Markov Model.

Still referring to FIG. 1, language processing module 114 may compare extracted words to categories of physiological data recorded at diagnostic engine 104, one or more prognostic labels recorded at diagnostic engine 104, and/or one or more categories of prognostic labels recorded at diagnostic engine 104; such data for comparison may be entered on diagnostic engine 104 as described above using expert data inputs or the like. In an embodiment, one or more categories may be enumerated, to find total count of mentions in such documents. Alternatively or additionally, language processing module 114 may operate to produce a language processing model. Language processing model may include a program automatically generated by diagnostic engine 104 and/or language processing module 114 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at diagnostic engine 104, or the like.

Still referring to FIG. 1, language processing module 114 and/or diagnostic engine 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. in an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 114 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 114 may use a corpus of documents to generate associations between language elements in a language processing module 114, and diagnostic engine 104 may then use such associations to analyze words extracted from one or more documents and determine that the one or more documents indicate significance of a category of physiological data, a given relationship of such categories to prognostic labels, and/or a given category of prognostic labels. In an embodiment, diagnostic engine 104 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into diagnostic engine 104. Documents may be entered into diagnostic engine 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of physiological sample, which then may be subjected to ranking, comparison to thresholds and/or elimination as described above.

Still referring to FIG. 1, diagnostic engine 104 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, diagnostic engine 104 may be configured, for instance as part of receiving the first training set 106, to associate at least correlated first prognostic label 110 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result diagnostic engine 104 may modify list of significant categories to reflect this difference.

Still referring to FIG. 1, diagnostic engine 104 is designed and configured to receive a second training set 116 including a plurality of second data entries. Each second data entry of the second training set 116 includes at least a second prognostic label 118; at least a second prognostic label 118 may include any label suitable for use as at least a first prognostic label 110 as described above. Each second data entry of the second training set 116 includes at least an ameliorative process label 120 correlated with the at least a second prognostic label 118, where correlation may include any correlation suitable for correlation of at least a first prognostic label 110 to at least an element of physiological data as described above. As used herein, an ameliorative process label 120 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

Continuing to refer to FIG. 1, in an embodiment diagnostic engine 104 may be configured, for instance as part of receiving second training set 116, to associate the at least second prognostic label 118 with at least a category from a list of significant categories of prognostic labels. This may be performed as described above for use of lists of significant categories with regard to at least a first prognostic label 110. Significance may be determined, and/or association with at least a category, may be performed for prognostic labels in first training set 106 according to a first process as described above and for prognostic labels in second training set 116 according to a second process as described above.

Still referring to FIG. 1, diagnostic engine 104 may be configured, for instance as part of receiving second training set 116, to associate at least a correlated ameliorative process label 120 with at least a category from a list of significant categories of ameliorative process labels 120. In an embodiment, diagnostic engine 104 and/or a user device connected to diagnostic engine 104 may provide a second graphical user interface 122 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 114 or the like as described above.

In an embodiment, and still referring to FIG. 1, diagnostic engine 104 may extract at least a second data entry from one or more documents; extraction may be performed using any language processing method as described above. Diagnostic engine 104 may be configured, for instance as part of receiving second training set 116, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label 120; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 120, and/or efficacy of ameliorative process labels 120 may be extracted from and/or determined from one or more medical history documents using any processes for language processing as described above; for instance, language processing module 114 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 1, diagnostic engine 104 may be configured, for instance as part of receiving second training set 116, to receiving at least a second data entry of the plurality of second data entries from at least an expert. This may be performed, without limitation using second graphical user interface as described above.

Continuing to refer to FIG. 1, diagnostic engine 104 may be configured to record at least a biological extraction. At least a biological extraction may include any element and/or elements of data suitable for use as at least an element of physiological state data as described above. At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor 124 may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor 124 may include any electromagnetic sensor, including without limitation electroencephalographic sensors, magnetoencephalographic sensors, electrocardiographic sensors, electromyographic sensors, or the like. At least a sensor 124 may include a temperature sensor. At least a sensor 124 may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor 124 may detect any hematological parameter including blood oxygen level, pulse rate, heart rate, pulse rhythm, blood sugar, and/or blood pressure. At least a sensor 108 may be configured to detect internal and/or external biomarkers and/or readings. At least a sensor 124 may be a part of system 100 or may be a separate device in communication with system 100.

Still referring to FIG. 1, at least a biological extraction may include any data suitable for use as physiological state data as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, a computing device 102 may present to user a set of assessment questions designed or intended to evaluate a current state of mind of the user, a current psychological state of the user, a personality trait of the user, or the like; a computing device 102 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure. At least a physiological sample may be added to biological extraction database 200.

With continued reference to FIG. 1, system 100 may include a prognostic label learner 126 operating on the diagnostic engine 104, the prognostic label learner 126 designed and configured to generate the at least a prognostic output as a function of the first training set 106 and the at least a biological extraction. Prognostic label learner 126 may include any hardware and/or software module. Prognostic label learner 126 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, prognostic label learner 126 may be designed and configured to generate at least a prognostic output by creating at least a first machine-learning model 128 relating physiological state data 108 to prognostic labels using the first training set 106 and generating the at least a prognostic output using the first machine-learning model 128; at least a first machine-learning model 128 may include one or more models that determine a mathematical relationship between physiological state data 108 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, machine-learning algorithms may generate prognostic output as a function of a classification of at least a prognostic label. Classification as used herein includes pairing or grouping prognostic labels as a function of a shared commonality. Classification may include for example, groupings, pairings, and/or trends between physiological data and current prognostic label, future prognostic label, and the like. In an embodiment, machine-learning algorithms may examine relationships between a future propensity of a user to develop a condition based on current user physiological data. Machine-learning algorithms may include any and all algorithms as performed by any modules, described herein for prognostic label learner 126. For example, machine-learning algorithms may relate fasting blood glucose readings of a user to user's future propensity to develop diabetes. Machine-learning algorithms may examine precursor condition and future propensity to develop a subsequent disorder. For example, machine-learning algorithms may examine a user diagnosed with chicken pox and user's future propensity to subsequently develop shingles. In yet another non-limiting example, machine-learning algorithms may examine infection with human papillomavirus (HPV) and subsequent cancer diagnosis. Machine-learning algorithms may examine a user's propensity to have recurring attacks of a disease or condition, for example a user with elevated uric acid levels and repeated attacks of gout. Machine-learning algorithms may examine user's genetic predisposition to develop a certain condition or disease. For example, machine-learning algorithms may examine presence of hereditary non-polyposis colorectal cancer (HNPCC) commonly known as lynch syndrome, and subsequent diagnosis of colorectal cancer. In yet another non-limiting example, machine-learning algorithms may examine presence of abnormal squamous cells and/or abnormal glandular cells in the cervix and subsequent development of cervical cancer. Machine-learning algorithms may examine progression of disease state, for example progression of human immunodeficiency virus (HIV) is marked by decline of CD4+T-Cells, with a count below 200 leading to a diagnosis of acquired immunodeficiency syndrome (AIDS). In yet another non-limiting example, progression of diabetes may be marked by increases of hemoglobin A1C levels with a level of 6.5% indicating a diagnosis of diabetes. Machine-learning algorithms may examine progression of disease by certain age groups. For example, progression of Multiple Sclerosis in users between the age of 20-30 as compared to progression of Multiple Sclerosis in users between the age of 70-80. Machine-learning algorithms may be examining progression of aging such as measurements of telomere length and/or oxidative stress levels and chance mortality risk. Machine-learning algorithms may examine development of co-morbid conditions when a disease or conditions is already present. For example, machine-learning algorithms may examine a user diagnosed with depression and subsequent diagnosis of a co-morbid condition such as migraines, generalized anxiety disorder, antisocial personality disorder, agoraphobia, obsessive-compulsive disorder, drug dependence alcohol dependence, and/or panic disorder. Machine-learning algorithms may examine a user's lifetime chance of developing a certain disease or condition, such as a user's lifetime risk of heart disease, Alzheimer's disease, diabetes and the like. Machine-learning algorithms may be grouped and implemented according to any of the methodologies as described below in reference to FIG. 19.

Continuing to refer to FIG. 1, machine-learning algorithm used to generate first machine-learning model 128 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, prognostic label learner 126 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 106; the trained network may then be used to apply detected relationships between elements of physiological state data 108 and prognostic labels.

With continued reference to FIG. 1, machine-learning algorithms may include unsupervised processes; unsupervised processes may, as a non-limiting example, be executed by an unsupervised learning module executing on diagnostic engine 104 and/or on another computing device in communication with diagnostic engine 104, which may include any hardware or software module as described in more detail below in reference to FIG. 7. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, prognostic label learner 126 and/or diagnostic engine 104 may perform an unsupervised machine learning process on first training set 106, which may cluster data of first training set 106 according to detected relationships between elements of the first training set 106, including without limitation correlations of elements of physiological state data 108 to each other and correlations of prognostic labels to each other; such relations may then be combined with supervised machine learning results to add new criteria for prognostic label learner 126 to apply in relating physiological state data 108 to prognostic labels. As a non-limiting, illustrative example, an unsupervised process may determine that a first element of physiological data acquired in a blood test correlates closely with a second element of physiological data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data 108 and second element of physiological state data 108 may indicate that the second element is also a good predictor for the prognostic label; second element may be included in a new supervised process to derive a relationship or may be used as a synonym or proxy for the first physiological element by prognostic label learner 126.

Still referring to FIG. 1, diagnostic engine 104 and/or prognostic label learner 126 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, prognostic label learner 126 and/or diagnostic engine 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 1, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 1, prognostic label learner 126 may alternatively or additionally be designed and configured to generate at least a prognostic output by executing a lazy learning process as a function of the first training set 106 and the at least a biological extraction; lazy learning processes may be performed by a lazy learning module executing on diagnostic engine 104 and/or on another computing device in communication with diagnostic engine 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 106. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 126 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

Continuing to refer to FIG. 1, prognostic label learner 126 may generate a plurality of prognostic labels having different implications for a particular person. For instance, where the at least a physiological sample includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 126 and/or diagnostic engine 104 may perform additional processes to resolve ambiguity. Processes may include presenting multiple possible results to a medical practitioner, informing the medical practitioner that one or more follow-up tests and/or physiological samples are needed to further determine a more definite prognostic label. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, prognostic label learner 126 and/or diagnostic engine 104 may operate a further algorithm to determine which of the multiple outputs is most likely to be correct; algorithm may include use of an additional supervised and/or unsupervised model. Alternatively or additionally, prognostic label learner 126 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 712 may be provided to user output device as described in further detail below.

Still referring to FIG. 1, diagnostic engine 104 includes an ameliorative process label learner 130 operating on the diagnostic engine 104, the ameliorative process label learner 130 designed and configured to generate the at least an ameliorative output as a function of the second training set 116 and the at least a prognostic output. Ameliorative process label learner 130 may include any hardware or software module suitable for use as a prognostic label learner 126 as described above. Ameliorative process label learner 130 is a machine-learning module as described above; ameliorative process label learner 130 may perform any machine-learning process or combination of processes suitable for use by a prognostic label learner 126 as described above. For instance, and without limitation, and ameliorative process label learner 130 may be configured to create a second machine-learning model 132 relating prognostic labels to ameliorative labels using the second training set 116 and generate the at least an ameliorative output using the second machine-learning model 132; second machine-learning model 132 may be generated according to any process, process steps, or combination of processes and/or process steps suitable for creation of first machine learning model. In an embodiment, ameliorative process label learner 130 may use data from first training set 106 as well as data from second training set 116; for instance, ameliorative process label learner 130 may use lazy learning and/or model generation to determine relationships between elements of physiological data, in combination with or instead of prognostic labels, and ameliorative labels. Where ameliorative process label learner 130 determines relationships between elements of physiological data and ameliorative labels directly, this may determine relationships between prognostic labels and ameliorative labels as well owing to the existence of relationships determined by prognostic label learner 126.

With continued reference to FIG. 1, diagnostic engine 104 may include an alimentary instruction label learner 134 operating on the diagnostic engine 104, the alimentary instruction label learner 134 designed and configured to generate at least an alimentary data output as a function of the second training set 116 and the at least a prognostic output. Alimentary instruction label learner 134 may include any hardware or software module suitable for use as a prognostic label learner 126 as described above. Alimentary instruction label learner 134 may include a machine-learning module as described above; alimentary instruction label learner 134 may perform any machine-learning process or combination of processes suitable for use by a prognostic label learner 126 as described above. For instance, and without limitation, and alimentary instruction label learner 134 may be configured to create a third machine-learning model 136 relating prognostic labels to alimentary labels using the second training set 116 and generate the at least an alimentary data output using the third machine-learning model 136; third machine-learning model 136 may be generated according to any process, process steps, or combination of processes and/or process steps suitable for creation of first machine learning model. In an embodiment, alimentary instruction label learner 134 may use data from first training set 106 as well as data from second training set 116; for instance, alimentary instruction label learner 134 may use lazy learning and/or model generation to determine relationships between elements of physiological data, in combination with or instead of prognostic labels, and alimentary labels, which may include, without limitation, a subset of ameliorative labels corresponding to alimentary processes. Where alimentary instruction label learner 134 determines relationships between elements of physiological data and alimentary labels directly, this may determine relationships between prognostic labels and alimentary labels as well owing to the existence of relationships determined by prognostic label learner 126.

With continued reference to FIG. 1, system 100 includes a plan generator module 138 operating on a computing device 102. Plan generator module 138 may include any suitable hardware or hardware module. In an embodiment, plan generator module 138 is designed and configured to generate a comprehensive instruction set associated with the user as a function of the diagnostic output. In an embodiment, comprehensive instruction set 140 is a data structure containing instructions to be provided to the user to explain the user's current prognostic status, as reflected by one or more prognostic outputs and provide the user with a plan based on the at least an ameliorative output, to achieve that. In an embodiment, comprehensive instruction set 140 may be generated based on at least an informed advisor output. Comprehensive instruction set 140 may include but is not limited to a program, strategy, summary, recommendation, or any other type of interactive platform that may be configured to comprise information associated with the user, an applicable verified external source, and one or more outputs derived from the analyses performed on the extraction from the user. Comprehensive instruction set 140 may describe to a user a future prognostic status to aspire to. Comprehensive instruction set 140 may reflect analyses and diagnostics associated with a user.

With continued reference to FIG. 1, system 100 includes an alimentary instruction set module 142 operating on a computing device 102. Alimentary instruction set module 142 may include any suitable hardware or hardware module. In an embodiment, alimentary instruction set module is designed and configured to generate as a function of the comprehensive instruction set an alimentary instruction set associated with the user. In an embodiment, alimentary instruction set 144 is a data structure containing a solution and/or suggestion to nourishment requirements or constitutional or chemical deficiencies. Alimentary instruction set 144 may be generated as a function of comprehensive instruction set 140. For example, comprehensive instruction set 140 that contains a recommendation to increase iron intake based on at least a biological extraction from a user reflecting anemia, may be utilized to generate an alimentary instruction set that includes a suggestion for a user to increase consumption of organ meats and green leafy vegetables. In yet another non-limiting example, alimentary instruction set 144 may contain a component seeking to remedy a B vitamin deficiency of a user based on a comprehensive instruction set 140 showing blood levels of B vitamins below normal acceptable values.

With continued reference to FIG. 1, alimentary instruction set 144 may be generated upon receiving at least an element of including a constitutional restriction. Element of user data as used herein, is any element of data describing the user, user needs, and/or user preferences. At least an element of user data may include a constitutional restriction. At least a constitutional restriction may include any constitutional reason that a user may be unable to engage in an alimentary instruction set process; at least a constitutional restriction may include a contraindication such as an injury, a diagnosis such as by an informed advisor including a functional medicine doctor, an allergy or food sensitivity issue, a contraindication to a medication or supplement and the like. For example, a user diagnosed with a blood clot and currently taking a blood thinning medication such as warfarin may report a constitutional restriction that includes a need to eat a consistent amount of Vitamin K containing foods such as leafy greens each day.

With continued reference to FIG. 1, alimentary instruction set may be generated upon receiving at least an element of user data including at least a user preference. At least a user preference may include, without limitation, any preference to engage in or eschew any alimentary instruction set process and/or other potential elements of comprehensive instruction set 140. At least a user preference may include for example religious preferences such as forbidden foods, medical interventions, exercise routines and the like. At least a user preference may include a user's dislike such as for example a user aversion to certain foods or nutrient groups, such as for example an aversion to eggs or an aversion to beets. At least a user preference may include for example a user's likes such as a user's preference to consume animal products or full fat dairy and the like. In an embodiment, alimentary instruction set 144 may be transmitted by alimentary instruction set module 142 to a user such as to a user client device 156, utilizing any of the transmission methodologies as described herein any network transmissions.

With continued reference to FIG. 1, alimentary instruction set module 142 may be configured to transmit a self-fulfillment instruction set to a user such as to user client device 156. Transmission may occur utilizing any of the transmission methodologies as described herein including any network transmissions. A "self-fulfillment instruction set" as used herein, is a data structure containing suggestions to be provided to the user to explain different ways in which a user can self-fulfill alimentary instruction set 144. Self-fulfillment instruction set 146 may contain suggestions as to foods and/or meals that a user may consume to correct nutrient and/or chemical deficiencies. Self-fulfillment instruction set 146 may be generated as a function of user geolocation. A user geolocation, as used in this disclosure, is an identification of a real-world geographical location of a user. A user geolocation may be obtained from a radar source, user client device such as a mobile phone, and/or internet connected device location. A user geolocation may include a global positioning system (GPS) of a system. A user geolocation may include geographic coordinates that specify the latitude and longitude where a user is located. User location including geographic location of a user may be utilized to generate a self-fulfillment instruction set that may contain ingredients or selections that may be available to a user in a certain geographical location. For example, a user with an alimentary instruction set that contains a deficiency of essential fatty acids may receive a self-fulfillment instruction set 146 that contains suggestions as to increasing one's consumption of salmon, herring, and cod. In an embodiment, self-fulfillment instruction set may be generated as a function of geolocation of a user. For example, a user with an essential fatty acid deficiency who is located in Seattle, Washington may receive a self-fulfillment instruction set 146 to increase consumption of locally available wild fish such as yellow perch, walleye, and striped bass, while a user with an essential fatty acid deficiency who is located in Naples, Florida may receive a self-fulfillment instruction set to increase one's consumption of red snapper, black grouper, and Florida pompano. In an embodiment, self-fulfillment instruction set 146 may include a plurality of different suggestions as to ways in which user can self-fulfill alimentary instruction set 144. For example, self-fulfillment instruction set may include suggested recipes a user may wish to cook, suggested groceries a user may wish to purchase, suggested meals a user may wish to consume, suggested meal plans a user may wish to follow, suggested eating habits a user may wish to follow, suggested restaurants a user may wish to eat at and the like. In an embodiment, self-fulfillment instruction set may include suggestions based on user location. For example, user may receive a suggested grocery list based on grocery stores in user's area where user is physically present.

With continued reference to FIG. 1, alimentary instruction set module 142 may include self-fulfillment learner 148. Self-fulfillment learner 148 may contain any hardware or software module suitable for use as prognostic label learner 126 as described above. Self-fulfillment learner 148 may include a machine-learning module as described above, self-fulfillment learner may perform any machine-learning process or combination of processes suitable for use by prognostic label learner 126 as described above. For instance and without limitation, self-fulfillment learner 148 may be configured to create a fourth machine-learning model 150 relating self-fulfillment instruction sets to ameliorative process labels and/or user entries containing an alimentary self-fulfillment action. An alimentary self-fulfillment action, is data describing how a user self-fulfilled. Fourth machine-learning model 150 may be generated according to any process, process steps, or combination of processes and/or process steps suitable for creation of first machine-learning model. In an embodiment, self-fulfillment learner 148 may use data from first training set 106, second training set 116; for instance, self-fulfillment learner 148 may use lazy learning and/or model generation to determine relationships between elements of physiological data, in combination with or instead of prognostic labels, and alimentary labels, which may include, without limitation, a subset of self-fulfillment labels corresponding to self-fulfillment actions. For example, user entry, as described in more detail below, may contain a description pertaining to how user self-fulfilled an alimentary instruction set, such as by shopping for groceries at a local grocery store. Subsequent self-fulfillment instruction sets 146 may be generated based on trends and data collected from user entries. User entries that contain trends and/or repeat habits established by a user may be utilized in machine-learning algorithms to generate subsequent self-fulfillment instruction sets 146. For example, a user entry that contains self-fulfillment actions that include actions such as cooking meals at home may be utilized to generate subsequent self-fulfillment instruction sets that focuses on new recipes as opposed to potential restaurants a user may want to visit. In yet another example, a user entry that contains self-fulfillment actions such as ordering takeout from a restaurant may be utilized to generate subsequent self-fulfillment instruction sets that may not focus on new recipes or grocery shopping lists but instead may focus on different restaurants a user may want to try.

With continued reference to FIG. 1, self-fulfillment learner 148 may perform machine-learning algorithms using a loss function analysis utilizing linear regression based on past interactions between a user and system 100 and self-fulfillment instruction sets to generate self-fulfillment instruction sets. In an embodiment, self-fulfillment learner 148 may compare one or more self-fulfillment options to a mathematical expression representing an optimal combination of self-fulfillment variables. Mathematical expression may include a linear combination of variables, weighted by coefficients representing relative importance of each variables in generating an optimal self-fulfillment action. For instance, a variable such as total transit time in seconds of a self-fulfillment action may be multiplied by a first coefficient representing the importance of total transit time, a total cost of a self-fulfillment action may be multiplied by a second coefficient representing the importance of cost, a degree of variance from an self-fulfillment instruction set may be represented as another parameter, which may be multiplied by another coefficient representing the importance of that parameter, a degree of variance from a requested recipe may be multiplied by an additional coefficient representing an importance of that parameter, and/or a parameter representing a degree of variance from one or more dietary restrictions may be provided a coefficient representing the importance of such a variance; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, self-fulfillment learner may calculate variables of each of a plurality of self-fulfillment actions, calculate an output of mathematical expression using the variables, and select a self-fulfillment action that produces an output having the lowest size, according to a given definition of "size," of the set of outputs representing each of the plurality of self-fulfillment actions; size may, for instance, included absolute value, numerical size, or the like. Selection of different loss functions may result in identification of different self-fulfillment actions as generating minimal outputs; for instance, where transit time is associated in a first loss function with a large coefficient or weight, a self-fulfillment action having a short transit time may minimize the first loss function, whereas a second loss function wherein transit time has a smaller coefficient but degree of variance from a dietary restriction has a larger coefficient may produce a minimal output for a different self-fulfillment action having a longer transit time but more closely hewing to a dietary restriction.

Alternatively or additionally, and still referring to FIG. 1, each self-fulfillment action may be represented by a mathematical expression having the same form as mathematical expression; self-fulfillment learner 148 may compare the former to the latter using an error function representing average difference between the two mathematical expressions. Error function may, as a non-limiting example, be calculated using the average difference between coefficients corresponding to each variable. A self-fulfillment action having a mathematical expression minimizing the error function may be selected, as representing an optimal expression of relative importance of variables to a system or user. In an embodiment, error function and loss function calculations may be combined; for instance, a self-fulfillment action resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to self-fulfillment action variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable to the user. Sliders or other inputs may be initialized prior to user entry as equal, or may be set to default values based on results of any machine-learning processes or combinations thereof as described in further detail below.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary provision options.

Self-fulfillment learner may generate a loss function of user specific variables and minimize the loss function. Self-fulfillment learner 148 may generate self-fulfillment instruction set 146 utilizing loss function analysis. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. Self-fulfillment learner 148 may utilize variables to model relationships between past interactions between a user and system 100 and self-fulfillment instruction sets. In an embodiment loss function analysis may utilize variables that may impact user interactions and/or self-fulfillment instruction sets. Variables may include user's habits, such as if user shops for groceries, how often user prepares meals at home, how often user eats out at restaurants or fast food stops, and the like. Variables may include for example, product quality which may include scores for a user's desire to consume organic or locally sourced ingredients. Variables may include for example product ingredients which may include scores for how different products may fulfill a user's alimentary instruction set needs, such as for example products that may contain iron for a user with anemia. Variables may include cost such as for example how much money a user is willing to pay for an ingredient or quality and how cost may factor into a user's overall budget for food. For example, a user with a fixed budget may be satisfied eating a nonorganic apple and avoiding the apple core where the pesticides reside as compared to spending more money on an organic apple. Variables may include travel time and geographical location such as for example how far a user is willing to travel to a grocery store or restaurant to acquire ingredients or a meal. Variables may include a user preference for certain foods or food groups such as a user who doesn't wish to consume foods containing monosodium glutamate (MSG) or a user who seeks to avoid trans fats. Variables may include user preferences such as a user's preference to consume user's favorite foods or meals. Variables may include availability of certain products and ingredients such as for example, availability of fresh seafood in Denver, Colo. or availability of fresh avocados in Boston, Mass. Loss function analysis may be user specific so as to create algorithms and outputs that are customize to variables for an individual user. User behaviors and user past responses may be utilized as training data to generate outputs. Variables contained within loss function analysis may be weighted and given different numerical scores. Variables may be stored and utilized to predict subsequent outputs. Outputs may seek to predict user behavior and past user interactions with system 100 and self-fulfillment instruction sets.

With continued reference to FIG. 1, system 100 includes fulfillment module 152. Fulfillment module 152 may include any suitable hardware or hardware module. Fulfillment module 152 is configured to generate a self-fulfillment instruction set utilizing a diagnostic output. Self-fulfillment instruction set includes any of the self-fulfillment instruction sets as described above in more detail above. Fulfillment module 152 is configured to generate a self-fulfillment instruction set utilizing a machine-learning model. Fulfillment module 152 is configured to receive user training data. User training data, as used in this disclosure, is training data that contains a plurality of previous user entries containing previous user alimentary instruction sets and a plurality of correlated self-fulfillment instruction sets. User training data is training data generated from previously generated alimentary instruction sets and self-fulfillment instruction sets generated for a user. In an embodiment, one or more previous user entries may be stored within variables database as described below in more detail. Fulfillment module 152 generates a self-fulfillment instruction set utilizing user training data and a fulfillment machine-learning model. Fulfillment machine-learning model, as used in this disclosure, is a machine learning model that utilizes alimentary instruction sets as an input and outputs self-fulfillment instruction sets. Fulfillment machine-learning model includes any of the machine-learning models as described herein. For instance and without limitation, fulfillment machine-learning model may include a supervised machine-learning model or an unsupervised machine-learning model. In yet another non-limiting example, fulfillment machine-learning model may include a classification algorithm, including any of the classification algorithms as described above. Fulfillment module 152 generates a self-fulfillment instruction set utilizing user training data and fulfillment machine-learning model.

With continued reference to FIG. 1, fulfillment module 152 is configured to receive from a user client device an element of user data describing a user geolocation. A user geolocation, as used in this disclosure, is an identification of a real-world geographical location of a user. A user geolocation may be obtained from a radar source, user client device such as a mobile phone, and/or internet connected device location. A user geolocation may include a global positioning system (GPS) of a system. A user geolocation may include geographic coordinates that specify the latitude and longitude where a user is located. A user geolocation may identify a location where a user spends a certain amount of time, such as a house where user resides during the week or an apartment where user stays on the weekend. In yet another non-limiting example, a user geolocation may identify an office building where a user works during the day or a home address in a tropical location where a user spends winter months. Fulfillment module 152 generates a self-fulfillment instruction set to identify a self-fulfillment action located within a user geolocation. For instance and without limitation, self-fulfillment instruction set may identify available groceries for sale at a grocery store located within the user geolocation. In yet another non-limiting example, self-fulfillment instruction set may recommend a specific meal that can be purchased at a restaurant located within the user geolocation. In yet another non-limiting example, self-fulfillment instruction set may recommend a meal delivery option that will deliver to the user geolocation. Fulfillment module 152 may be configured to receive one or more network transmissions from one or more computing devices and/or servers operated by a third party. A third party, may include any party that may offer fulfillment options. For example, a third party may include a restaurant that sells meals or a grocery store that sells packaged goods. In yet another non-limiting example, a third party may include a home kitchen where meals are prepared and available for purchase by a chef. In yet another non-limiting example, a third party may include any online or retail location where groceries are available for purchase.

With continued reference to FIG. 1, fulfillment module 146 is configured to receive a user entry containing a completed alimentary self-fulfillment action. In an embodiment, fulfillment module 152 may receive a user entry containing a completed alimentary self-fulfillment action from a user client device 156 operated by a user. User client device may include any of the user client devices as described in more detail below. Fulfillment module 152 may receive a user entry containing a completed alimentary self-fulfillment action utilizing any network methodology as described herein. A completed alimentary self-fulfillment action as used herein, includes any user entry containing data describing as to how a user self-fulfilled. Self-fulfilled as used herein, includes any action or step a user performed or didn't perform based on an alimentary instruction set. User entry may include a user generated response that may include text, graphics, photographs, descriptions, sentences, words, selections, choices, and the like describing how a user self-fulfilled an alimentary instruction set 144. For example, user entry may contain a photograph a meal a user consumed for breakfast the previous day. In yet another non-limiting example, alimentary instruction set 144 may contain a recommendation for a user to increase intake of monounsaturated and polyunsaturated fats to increase low levels of high density lipoprotein (HDL). User entry may include a user generated response that may contain a description of a meal user consumed for lunch consisting of a chopped salad topped with avocado, walnuts, and chicken. User entry may include a description of any self-fulfillment action that a user contemplated or thought about performing. For instance and without limitation, user entry may describe a list of groceries a user contemplated purchasing or a meal at a restaurant that a user is considering purchasing. User entry may include a graphic such as a photograph a user may take of user's meal and transmit to fulfillment module. In an embodiment, user may select from a list certain foods user may have consumed. In an embodiment, user may generate a user entry at timed intervals, such as after every meal user consumes or at the end of each day. In an embodiment, user may generate a user entry sporadically or at untimed intervals. For example, a user who has an alimentary instruction set 144 that includes recommendations to increase consumption of melatonin rich foods such as cherries when user experiences insomnia, may cause a user to generate a user entry sporadically when a user experiences insomnia. Fulfillment module 152 may be configured to match user entry containing an alimentary instruction set as a function of the user entry to at least a self-fulfillment instruction set as described in more detail below. Fulfillment module 152 may be configured to match user entry containing an alimentary instruction set as a function off the user entry to at least an alimentary instruction set as described in more detail below.

With continued reference to FIG. 1, fulfillment module 146 is configured to receive at an image capture device located on computing device a wireless transmission from a user client device. An image capture device, as used in this disclosure, includes any device suitable to take a picture and/or photograph. Image capture device may include for example, a camera, mobile phone camera, scanner or the like. In an embodiment, image capture device may be located on user client device, such as a mobile phone camera. Image capture device is configured to receive a photograph of a completed alimentary self-fulfillment action. For instance and without limitation, image capture device may receive a photograph of a completed alimentary self-fulfillment action that contains receipt data. Receipt data, as used in this disclosure, includes any data describing any purchase of goods relating to a self-fulfillment action. For instance and without limitation, receipt data may contain data describing groceries a user purchased at a grocery store. In yet another non-limiting example, receipt data may contain data describing a meal kit that a user purchased or a selection of meals that a user ordered from a restaurant and had delivered to the user's office. Receipt data may include receipts from online purchases such as groceries ordered online from a grocery store. Receipt data may include receipts from purchases in person at a store.

With continued reference to FIG. 1, fulfillment module is configured to classify a user entry containing a photograph of a self-fulfillment action utilizing a self-fulfillment classifier. A classifier, as used in this disclosure, is a machine-learning model, such as a mathematical model, neural net, or program generated by a machine-learning algorithm known as a classification algorithm, that sorts inputs into categories or bins of data, outputting the categories or bins of data and/or labels associated therewith. A self-fulfillment classifier, as used in this disclosure, is a classifier configured to input a photograph of a self-fulfillment action and output a self-fulfillment activity category label. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. A self-fulfillment activity category label, as used in this disclosure, is data describing a class of a completed alimentary self-fulfillment action. A class of a completed alimentary self-fulfillment action may indicate the method or way in which a self-fulfillment action was completed. A class of a completed alimentary self-fulfillment action may indicate an activity that a user performed For instance and without limitation, a class may indicate if a user consumed food through food delivery, if a user went grocery shopping in person at a store, if a user ordered groceries from an online retail app, if a user ordered a meal kit, if a user prepared a meal kit, if a user cooked dinner at home, if a user had a chef prepare a meal, if a user had precooked meals sent to the user's house, if a user bought a carry out meal at a grocery store and the like. Fulfillment module 152 utilizes a self-fulfillment activity category label to update self-fulfillment instruction set. For instance and without limitation, fulfillment module 152 may utilize a self-fulfillment category label to recommend subsequent self-fulfillment actions based on repeated activities and habits of a user. For example, a user entry that contains a photograph of meals a user has ordered from restaurants in the area may be utilized by fulfillment module to generate an updated self-fulfillment instruction set that recommends other meal options within the user's geographic location. In yet another non-limiting example, a user entry that contains a photograph of groceries that a user purchased at a grocery store may be utilized to update a self-fulfillment instruction that contains instructions for how a user can self-fulfill with subsequent grocery purchases. In yet another non-limiting example, a user entry that is not classified to a self-fulfillment activity category label may be utilized by fulfillment module 152 to generate a self-fulfillment instruction set that does not contain other non-selected self-fulfillment category labels in subsequent self-fulfillment instruction sets. For example, three photographs of user entries classified to a self-fulfillment category label of grocery shopping may be utilized to update a self-fulfillment instruction set that contains a self-fulfillment action of grocery shopping and does not contain recommendations for meal delivery or meals from restaurants. With continued referenced to FIG. 1, fulfillment module 152 is configured to generate a loss function. Loss function includes any of the loss functions as described above in more detail. Fulfillment module 152 is configured to receive a user input from a user client device. A user input as used in this disclosure, includes any preference related to fulfillment. Fulfillment module 152 receives a user input utilizing any network methodology as described herein. A user input may contain a user preference relating to one or more variables preferences relating to self-fulfillment. A variable preference, as used in this disclosure, is data describing a user's selection and/or input relating to self-fulfillment variables. Variables may include any factor that may affect self-fulfillment including cost, access to certain foods, time to travel to locate certain foods, and the like. For example, a variable may specify how far by distance or how far in time a user prefers to travel to a store to purchase groceries. In yet another non-limiting example, a variable may specify a user's preference regarding product quality, such as if a user prefers to consume organic produce or conventionally raise meats. In yet another non-limiting example, a variable may specify if a user prefers to purchase groceries in person at a particular grocery store or if a user purchases produce at a farm stand or through a community sponsored agriculture (CSA) program. In yet another non-limiting example, a variable may specify certain foods that a user enjoys eating such as kale, broccoli, and spinach but that a user dislikes red bell pepper. In yet another non-limiting example, a variable may specify if a user follows a certain diet or way of eating based on certain health conditions, ethical beliefs, religious reasons and the like. In yet another non-limiting example, a variable may specify a certain cost or threshold amount that a user is willing to spend on a self-fulfillment action. Fulfillment module 152 generates a loss function utilizing a user input and minimizes the loss function. This may be performed utilizing any of the methodologies as described above in more detail.

With continued reference to FIG. 1, fulfillment module is configured to update a self-fulfillment instruction set utilizing an indication of user digestibility. Fulfillment module is configured to record a second biological extraction. A second biological extraction includes any biological extraction as described above in more detail. A second biological extraction contains an element of user physiological data containing an indication as to user digestibility. User digestibility includes any process in which nutrition is broken up physically and chemically and converted into a substance suitable for absorption and assimilation into the body. An element of user physiological data containing an indication as to user digestibility includes any biological extraction pertaining to and/or relating to user digestibility. For example, an element of user physiological data containing an indication as to user digestibility may include a biological extraction related to one or more dimensions of the human body. An element of user physiological data may contain a stool test analyzed for parasites or a marker of gut wall absorption analyzed for d-lactate, lactulose, and mannitol levels. In yet another non-limiting example, an element of user physiological data may contain a blood test analyzed for one or more nutrient levels. Fulfillment module updates a self-fulfillment instruction set utilizing an indication of user digestibility. For example, an indication of user digestibility that indicates a user has an altered microbiome may be utilized to update a self-fulfillment instruction set to contain a recommendation to purchase foods rich in beneficial bacterial at a grocery store such as sauerkraut or kombucha or to purchase a meal from a restaurant that is high in prebiotic fiber including asparagus, banana, leeks, and onion.

With continued reference to FIG. 1, system 100 may include a client-interface module 152. Client-interface module 152 may include any suitable hardware or software module. Client-interface module 152 may designed and configured to transmit comprehensive instruction set 140 to at least a user client device 156 associated with the user. A user client device 156 may include, without limitation, a display in communication with diagnostic engine 104; display may include any display as described herein. A user client device 156 may include an addition computing device, such as a mobile device, laptop, desktop computer, or the like; as a non-limiting example, the user client device 156 may be a computer and/or workstation operated by a medical professional. Output may be displayed on at least a user client device 156 using an output graphical user interface; output graphical user interface may display at least a current prognostic descriptor, at least a future prognostic descriptor, and/or at least an ameliorative process descriptor.

With continued reference to FIG. 1, system 100 may include at least an advisory module executing on the computing device 102. At least an advisory module 158 may include any suitable hardware or software module. In an embodiment, at least an advisory module 158 is designed and configured to generate at least an advisory output as a function of the comprehensive instruction set 140 and may transmit the advisory output to at least an advisor client device 160. At least an advisor client device 160 may include any device suitable for use as a user client device 156 as described above. At least an advisor client device 160 may operate on system 100 and may be a user client device 156 as described above; that is, at least an advisory output may be output to the user client device 156. Alternatively or additionally, at least an advisor client device 160 may be operated by an informed advisor, defined for the purposes of this disclosure as any person besides the user who has access to information usable to aid user in interaction with artificial intelligence advisory system. An informed advisor may include, without limitation, a medical professional such as a doctor, nurse, nurse practitioner, functional medicine practitioner, any professional with a career in medicine, nutrition, genetics, fitness, life sciences, insurance, and/or any other applicable industry that may contribute information and data to system 100 regarding medical needs. An informed advisor may include a spiritual or philosophical advisor, such as a religious leader, pastor, imam, rabbi, or the like. An informed advisor may include a physical fitness advisor, such as without limitation a personal trainer, instructor in yoga or martial arts, sports coach, or the like. Advisory module 158 may generate at least an advisory output while consulting information contained within advisory database as described below in more detail in reference to FIGS. 15-17.

Figure 2:
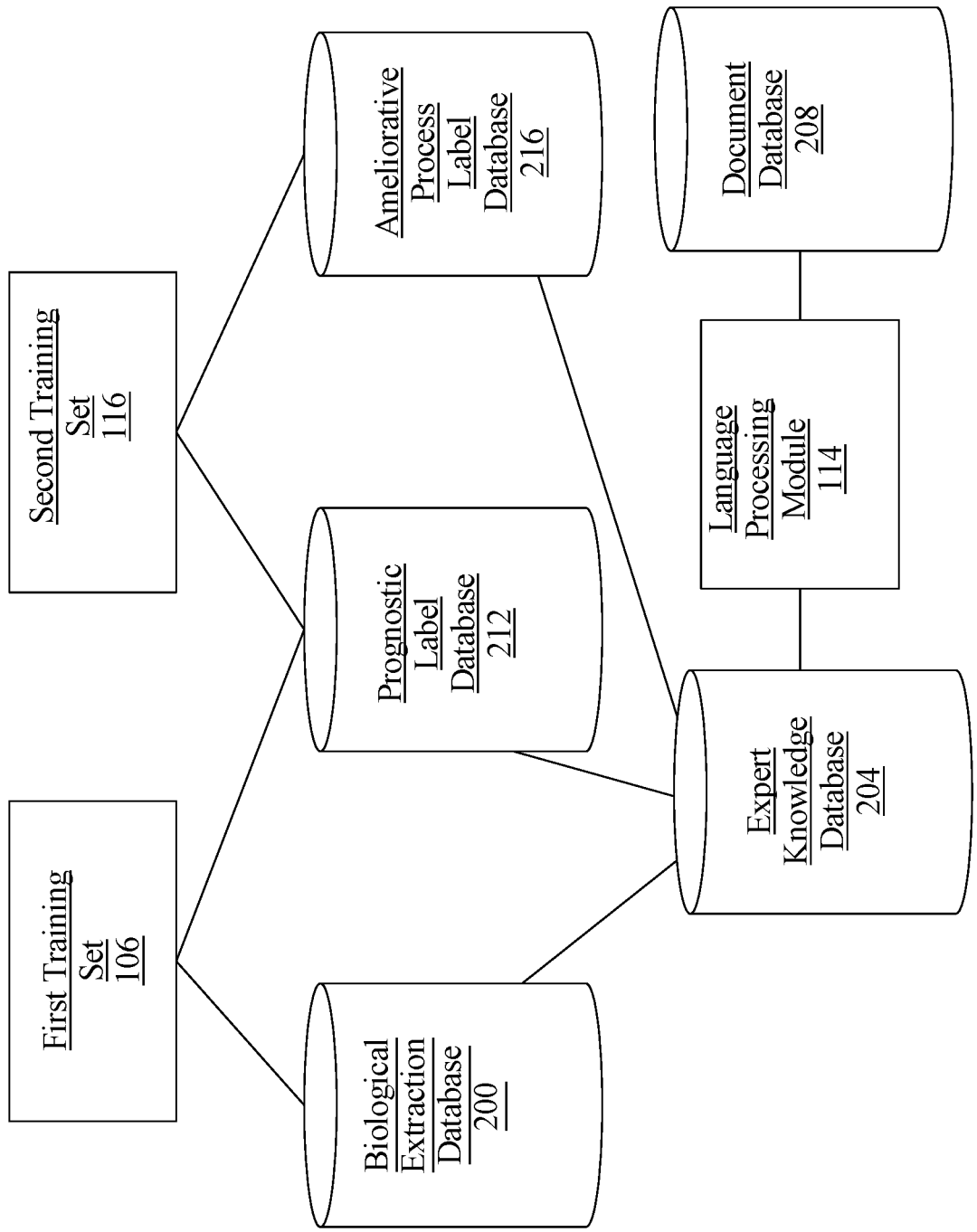
FIG. 2 is a block diagram illustrating embodiments of data storage facilities for use in disclosed systems and methods.

Referring now to FIG. 2, data incorporated in first training set 106 and/or second training set 116 may be incorporated in one or more databases. As a non-limiting example, one or elements of physiological state data may be stored in and/or retrieved from a biological extraction database 200. A biological extraction database 200 may include any data structure for ordered storage and retrieval of data, which may be implemented as a hardware or software module. A biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a biological extraction database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 200 may reflect categories, cohorts, and/or populations of data consistently with this disclosure.

With continued reference to FIG. 2, diagnostic engine 104 may be configured to have a feedback mechanism. In an embodiment, diagnostic engine 104 may be configured to receive a first training set 200 and/or a second training set 220 generated by system 100. For example, data about a user that has been previously been analyzed by diagnostic engine 104 may be utilized in algorithms by first model 240 and/or second model 248. Such algorithms may be continuously updated as a function of such data. In yet another embodiment, data analyzed by language processing module 216 may be utilized as part of training data generating algorithms by first model 240 and/or second model 248 and/or any other machine learning process performed by diagnostic engine 104.

Figure 3:
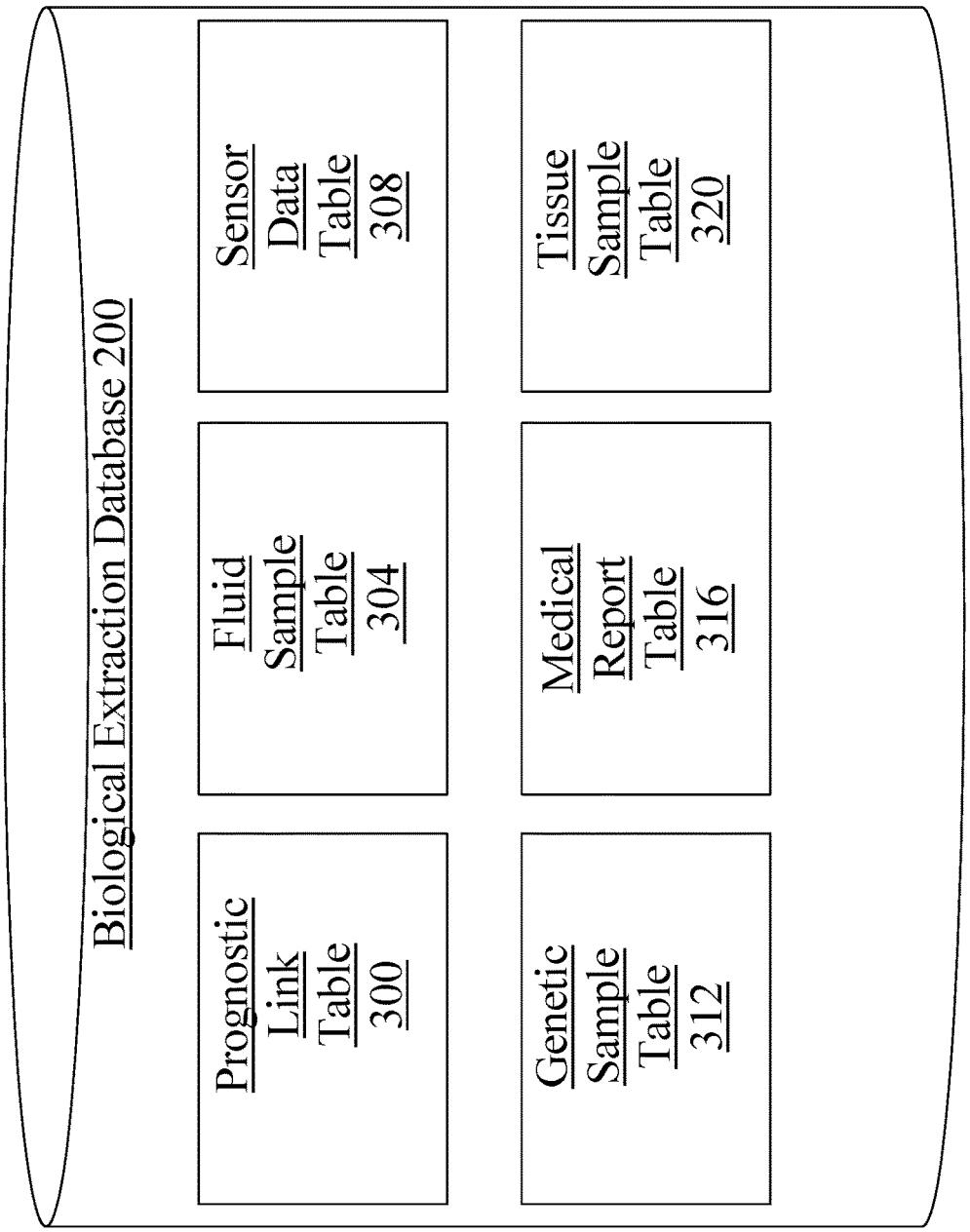
FIG. 3 is a block diagram illustrating an exemplary embodiment of a biological extraction database.

Referring now to FIG. 3, one or more database tables in biological extraction database 200 may include, as a non-limiting example, a prognostic link table 300. Prognostic link table 300 may be a table relating physiological sample data as described above to prognostic labels; for instance, where an expert has entered data relating a prognostic label to a category of physiological sample data and/or to an element of physiological sample data via first graphical user interface 112 as described above, one or more rows recording such an entry may be inserted in prognostic link table 300. Alternatively or additionally, linking of prognostic labels to physiological sample data may be performed entirely in a prognostic label database as described below.

With continued reference to FIG. 3, biological extraction database 200 may include tables listing one or more samples according to sample source. For instance, and without limitation, biological extraction database 200 may include a fluid sample table 304 listing samples acquired from a person by extraction of fluids, such as without limitation blood, lymph cerebrospinal fluid, or the like. As another non-limiting example, biological extraction database 200 may include a sensor data table 308, which may list samples acquired using one or more sensors, for instance as described in further detail below. As a further non-limiting example, biological extraction database 200 may include a genetic sample table 312, which may list partial or entire sequences of genetic material. Genetic material may be extracted and amplified, as a non-limiting example, using polymerase chain reactions (PCR) or the like. As a further example, also non-limiting, biological extraction database 200 may include a medical report table 316, which may list textual descriptions of medical tests, including without limitation radiological tests or tests of strength and/or dexterity or the like. Data in medical report table may be sorted and/or categorized using a language processing module 312, for instance, translating a textual description into a numerical value and a label corresponding to a category of physiological data; this may be performed using any language processing algorithm or algorithms as referred to in this disclosure. As another non-limiting example, biological extraction database 200 may include a tissue sample table 320, which may record physiological samples obtained using tissue samples. Tables presented above are presented for exemplary purposes only; persons skilled in the art will be aware of various ways in which data may be organized in biological extraction database 200 consistently with this disclosure.

Referring again to FIG. 2, diagnostic engine 104 and/or another device in system 100 may populate one or more fields in biological extraction database 200 using expert information, which may be extracted or retrieved from an expert knowledge database 204. An expert knowledge database 204 may include any data structure and/or data store suitable for use as a biological extraction database 200 as described above. Expert knowledge database 204 may include data entries reflecting one or more expert submissions of data such as may have been submitted according to any process described above in reference to FIG. 1, including without limitation by using first graphical user interface 112 and/or second graphical user interface 140. Expert knowledge database may include one or more fields generated by language processing module 114, such as without limitation fields extracted from one or more documents as described above. For instance, and without limitation, one or more categories of physiological data and/or related prognostic labels and/or categories of prognostic labels associated with an element of physiological state data as described above may be stored in generalized from in an expert knowledge database 204 and linked to, entered in, or associated with entries in a biological extraction database 200. Documents may be stored and/or retrieved by diagnostic engine 104 and/or language processing module 114 in and/or from a document database 208; document database 208 may include any data structure and/or data store suitable for use as biological extraction database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
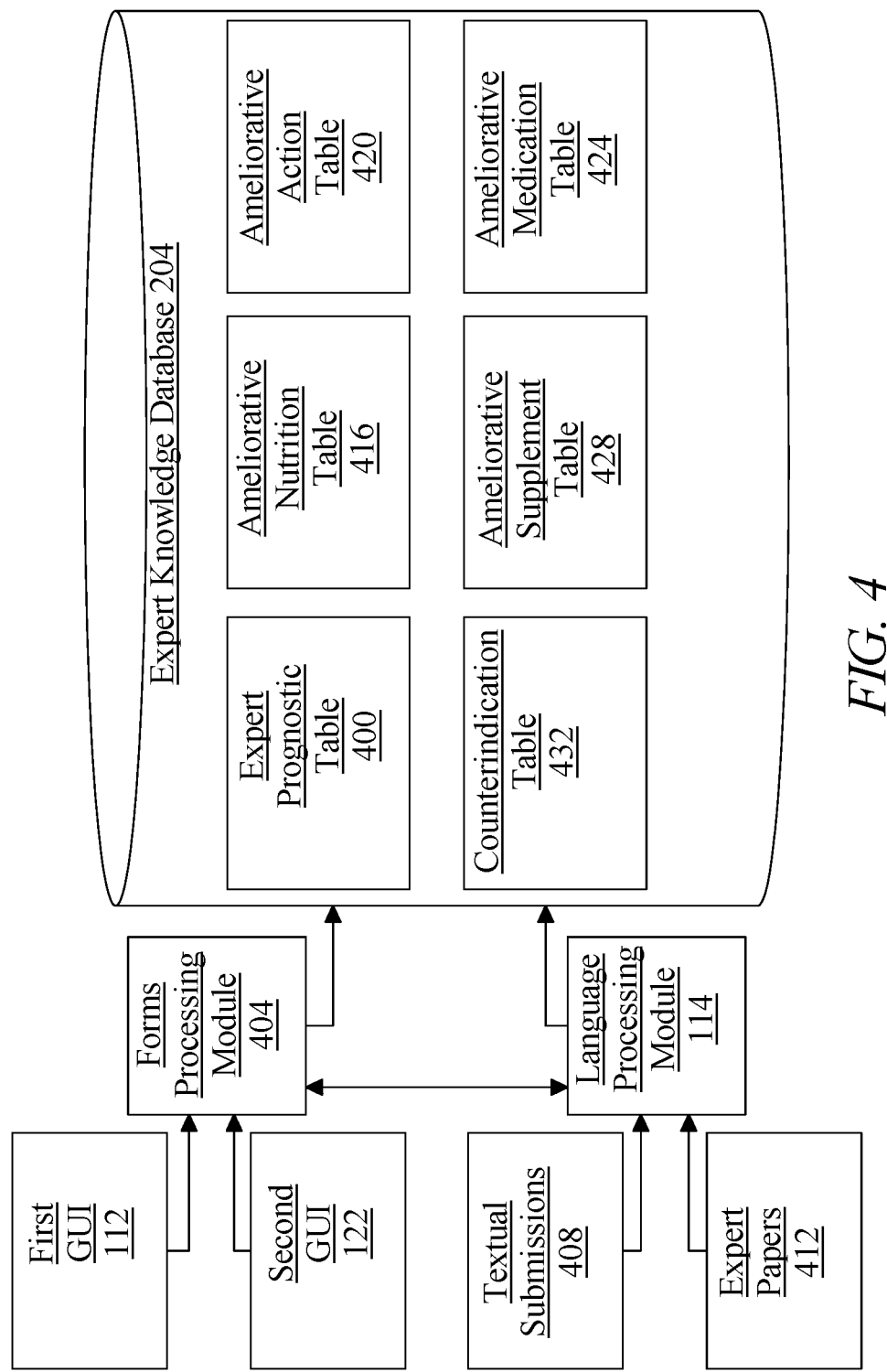
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via first graphical user interface 112 as described above, one or more rows recording such an entry may be inserted in expert prognostic table 400. In an embodiment, a forms processing module 404 may sort data entered in a submission via first graphical user interface 112 by, for instance, sorting data from entries in the first graphical user interface 112 to related categories of data; for instance, data entered in an entry relating in the first graphical user interface 112 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 114 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 114. Data may be extracted from expert papers 412, which may include without limitation publications in medical and/or scientific journals, by language processing module 114 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more ameliorative process labels; expert data populating such tables may be provided, without limitation, using any process described above, including entry of data from second graphical user interface 140 via forms processing module 404 and/or language processing module 114, processing of textual submissions 408, or processing of expert papers 412. For instance, and without limitation, an ameliorative nutrition table 416 may list one or more ameliorative processes based on nutritional instructions, and/or links of such one or more ameliorative processes to prognostic labels, as provided by experts according to any method of processing and/or entering expert data as described above. As a further example an ameliorative action table 420 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above. As an additional example, an ameliorative supplement table 424 may list one or more ameliorative processes based on nutritional supplements, such as vitamin pills or the like, and/or links of such one or more ameliorative processes to prognostic labels, as provided by experts according to any method of processing and/or entering expert data as described above. As a further non-limiting example, an ameliorative medication table 428 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above. As an additional example, a counterindication table 432 may list one or more counterindications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 204 consistently with this disclosure.

Referring again to FIG. 2, a prognostic label database 212, which may be implemented in any manner suitable for implementation of biological extraction database 200, may be used to store prognostic labels used in system 100, including any prognostic labels correlated with elements of physiological data in first training set 106 as described above; prognostic labels may be linked to or refer to entries in biological extraction database 200 to which prognostic labels correspond. Linking may be performed by reference to historical data concerning physiological samples, such as diagnoses, prognoses, and/or other medical conclusions derived from physiological samples in the past; alternatively or additionally, a relationship between a prognostic label and a data entry in biological extraction database 200 may be determined by reference to a record in an expert knowledge database 204 linking a given prognostic label to a given category of physiological sample as described above. Entries in prognostic label database 212 may be associated with one or more categories of prognostic labels as described above, for instance using data stored in and/or extracted from an expert knowledge database 204.

Figure 5:
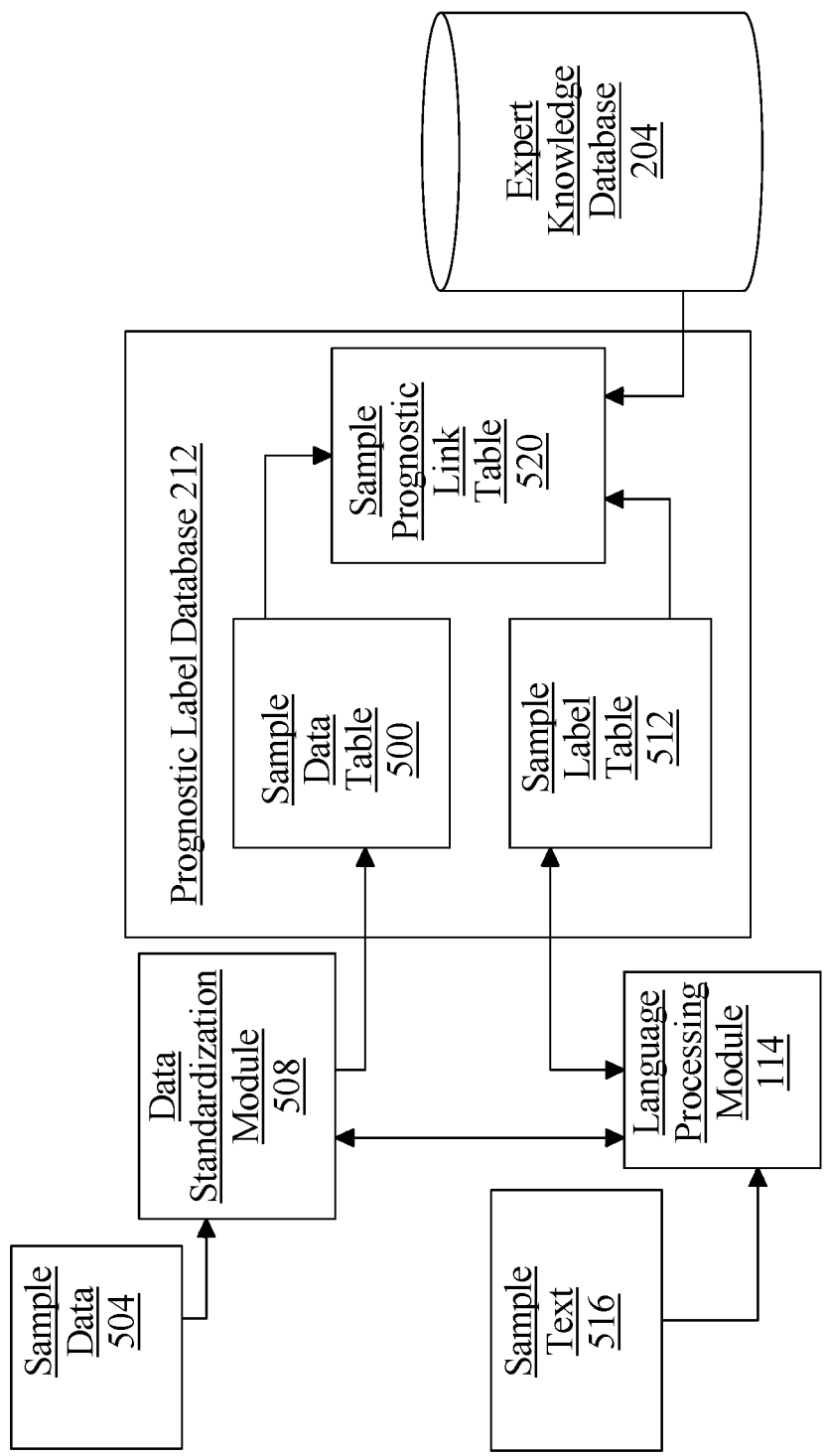
FIG. 5 is a block diagram illustrating an exemplary embodiment of a prognostic label database.

Referring now to FIG. 5, an exemplary embodiment of a prognostic label database 212 is illustrated. Prognostic label database 212 may, as a non-limiting example, organize data stored in the prognostic label database 212 according to one or more database tables. One or more database tables may be linked to one another by, for instance, common column values. For instance, a common column between two tables of prognostic label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in prognostic label database 212 may include, as a non-limiting example, a sample data table 500. Sample data table 500 may be a table listing sample data, along with, for instance, one or more linking columns to link such data to other information stored in prognostic label database 212. In an embodiment, sample data 504 may be acquired, for instance from biological extraction database 200, in a raw or unsorted form, and may be translated into standard forms, such as standard units of measurement, labels associated with particular physiological data values, or the like; this may be accomplished using a data standardization module 508, which may perform unit conversions. Data standardization module 508 may alternatively or additionally map textual information, such as labels describing values tested for or the like, using language processing module 114 or equivalent components and/or algorithms thereto.

Continuing to refer to FIG. 5, prognostic label database 212 may include a sample label table 512; sample label table 512 may list prognostic labels received with and/or extracted from physiological samples, for instance as received in the form of sample text 516. A language processing module 114 may compare textual information so received to prognostic labels and/or form new prognostic labels according to any suitable process as described above. Sample prognostic link table may combine samples with prognostic labels, as acquired from sample label table and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Referring again to FIG. 2, first training set 106 may be populated by retrieval of one or more records from biological extraction database 200 and/or prognostic label database 212; in an embodiment, entries retrieved from biological extraction database 200 and/or prognostic label database 212 may be filtered and or select via query to match one or more additional elements of information as described above, so as to retrieve a first training set 106 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from biological extraction database 200 and/or prognostic label database to generate a first training set to reflect individualized group data pertaining to a person of interest in operation of system and/or method, including without limitation a person with regard to whom at least a physiological sample is being evaluated as described in further detail below. Diagnostic engine 104 may alternatively or additionally receive a first training set 106 and store one or more entries in biological extraction database 200 and/or prognostic label database 212 as extracted from elements of first training set 106.

Still referring to FIG. 2, system 100 may include or communicate with an ameliorative process label database 216; an ameliorative process label database 216 may include any data structure and/or datastore suitable for use as a biological extraction database 200 as described above. An ameliorative process label database 216 may include one or more entries listing labels associated with one or more ameliorative processes as described above, including any ameliorative labels correlated with prognostic labels in second training set 116 as described above; ameliorative process labels may be linked to or refer to entries in prognostic label database 212 to which ameliorative process labels correspond. Linking may be performed by reference to historical data concerning prognostic labels, such as therapies, treatments, and/or lifestyle or dietary choices chosen to alleviate conditions associated with prognostic labels in the past; alternatively or additionally, a relationship between an ameliorative process label and a data entry in prognostic label database 212 may be determined by reference to a record in an expert knowledge database 204 linking a given ameliorative process label to a given category of prognostic label as described above. Entries in ameliorative process label database 212 may be associated with one or more categories of prognostic labels as described above, for instance using data stored in and/or extracted from an expert knowledge database 204.

Figure 6:
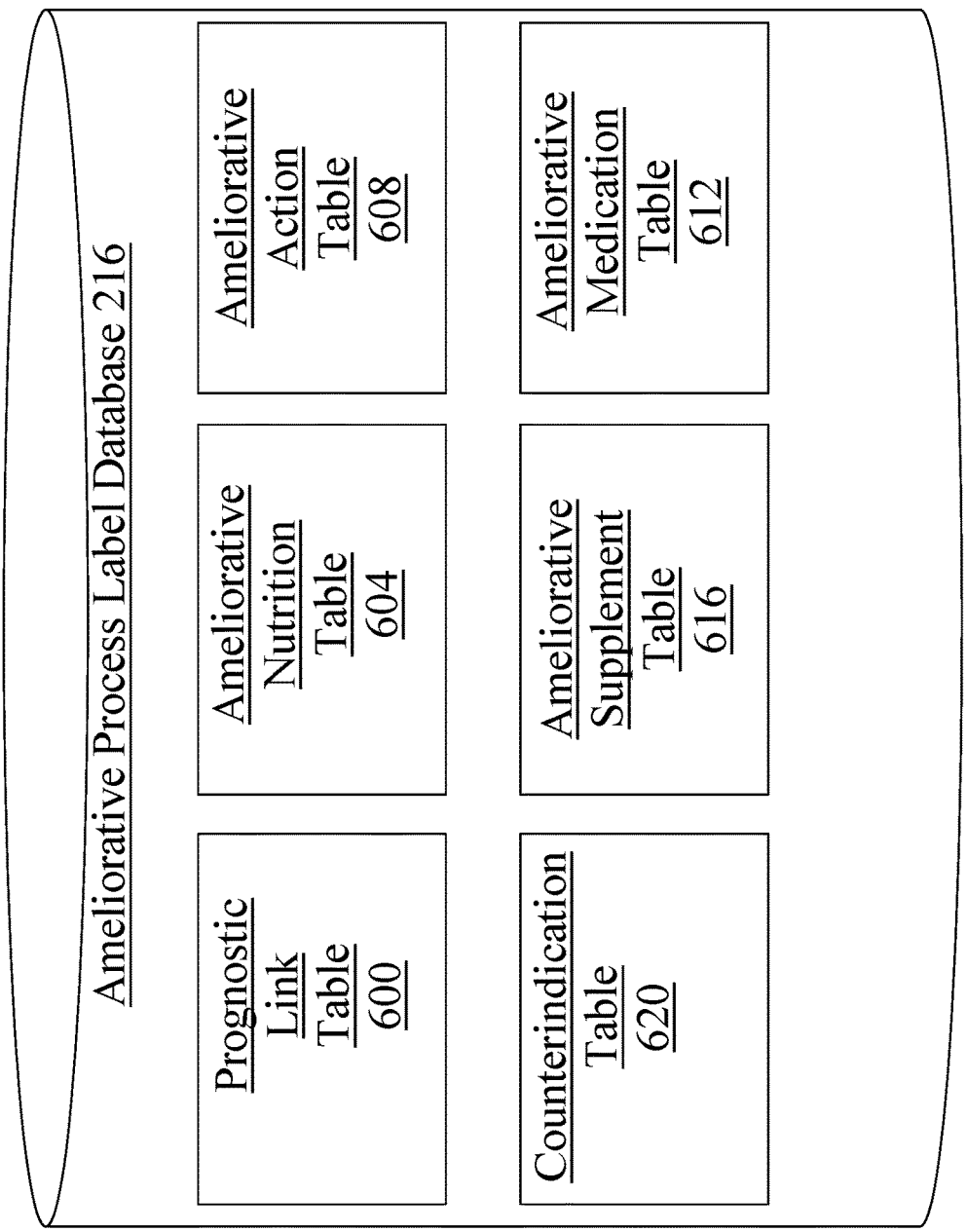
FIG. 6 is a block diagram illustrating an exemplary embodiment of an ameliorative process label database.

Referring now to FIG. 6, an exemplary embodiment of an ameliorative process label database 216 is illustrated. Ameliorative process label database 216 may, as a non-limiting example, organize data stored in the ameliorative process label database 216 according to one or more database tables. One or more database tables may be linked to one another by, for instance, common column values. For instance, a common column between two tables of ameliorative process label database 216 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, ameliorative process label database 216 may include a prognostic link table 600; prognostic link table may link ameliorative process data to prognostic label data, using any suitable method for linking data in two or more tables as described above. Ameliorative process label database 216 may include an ameliorative nutrition table 604, which may list one or more ameliorative processes based on nutritional instructions, and/or links of such one or more ameliorative processes to prognostic labels, for instance as provided by experts according to any method of processing and/or entering expert data as described above, and/or using one or more machine-learning processes as set forth in further detail below. As a further example an ameliorative action table 608 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above and/or using one or more machine-learning processes as set forth in further detail below. As an additional example, an ameliorative supplement table 612 may list one or more ameliorative processes based on nutritional supplements, such as vitamin pills or the like, and/or links of such one or more ameliorative processes to prognostic labels, as provided by experts according to any method of processing and/or entering expert data as described above and/or using one or more machine-learning processes as set forth in further detail below. As a further non-limiting example, an ameliorative medication table 616 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above and/or using one or more machine-learning processes as set forth in further detail below. As an additional example, a counter-indication table 620 may list one or more counter-indications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like; this may be acquired using expert submission as described above and/or using one or more machine-learning processes as set forth in further detail below. Tables presented above are presented for exemplary purposes only; persons skilled in the art will be aware of various ways in which data may be organized in ameliorative process database 216 consistently with this disclosure Referring again to FIG. 2, second training set 116 may be populated by retrieval of one or more records from prognostic label database 212 and/or ameliorative process label database 216; in an embodiment, entries retrieved from prognostic label database 212 and/or ameliorative process label database 216 may be filtered and or select via query to match one or more additional elements of information as described above, so as to retrieve a second training set 116 including data belonging to a given cohort, demographic population, or other set, so as to generate outputs as described below that are tailored to a person or persons with regard to whom system 100 classifies prognostic labels to ameliorative process labels as set forth in further detail below. Persons skilled in the art, upon reviewing the entirety of this disclosure, will be aware of various ways in which records may be retrieved from prognostic label database 212 and/or ameliorative process label database 216 to generate a second training set 116 to reflect individualized group data pertaining to a person of interest in operation of system and/or method, including without limitation a person with regard to whom at least a physiological sample is being evaluated as described in further detail below. Diagnostic engine 104 may alternatively or additionally receive a second training set 116 and store one or more entries in prognostic label database 212 and/or ameliorative process label database 216 as extracted from elements of second training set 116.

With continued reference to FIG. 2, diagnostic engine 104 may receive an update to one or more elements of data represented in first training set 106 and/or second training set 116, and may perform one or more modifications to first training set 106 and/or second training set 116, or to biological extraction database 200, expert knowledge database 204, prognostic label database 212, and/or ameliorative process label database 216 as a result. For instance, a physiological sample may turn out to have been erroneously recorded; diagnostic engine 104 may remove it from first training set 106, second training set 116, biological extraction database 200, expert knowledge database 204, prognostic label database 212, and/or ameliorative process label database 216 as a result. As a further example, a medical and/or academic paper, or a study on which it was based, may be revoked; diagnostic engine 104 may remove it from first training set 106, second training set 116, biological extraction database 200, expert knowledge database 204, prognostic label database 212, and/or ameliorative process label database 216 as a result. Information provided by an expert may likewise be removed if the expert loses credentials or is revealed to have acted fraudulently.

Continuing to refer to FIG. 2, elements of data first training set 106, second training set 116, biological extraction database 200, expert knowledge database 204, prognostic label database 212, and/or ameliorative process label database 216 may have temporal attributes, such as timestamps; diagnostic engine 104 may order such elements according to recency, select only elements more recently entered for first training set 106 and/or second training set 116, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Figure 7:
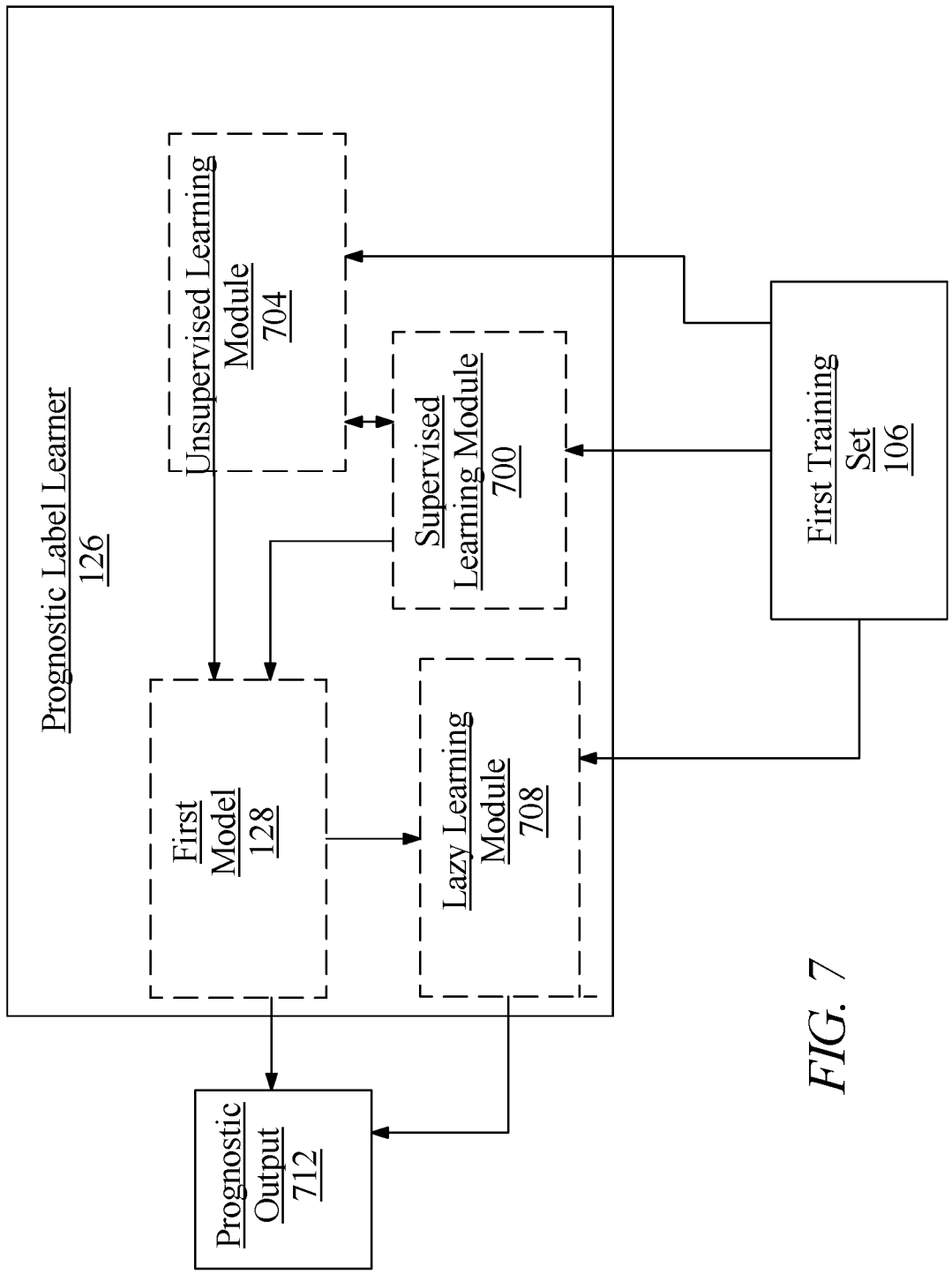
FIG. 7 is a block diagram illustrating an exemplary embodiment of a prognostic label learner and associated system elements.

Referring now to FIG. 7, machine-learning algorithms used by prognostic label learner 126 may include supervised machine-learning algorithms, which may, as a non-limiting example be executed using a supervised learning module 700 executing on diagnostic engine 104 and/or on another computing device in communication with diagnostic engine 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data 108 and/or combination of elements of physiological data is associated with a given prognostic label and/or combination of prognostic labels to minimize the probability that a given element of physiological state data 108 and/or combination of elements of physiological state data 108 is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 106. Persons skilled in the art, upon reviewing the entirety of this disclosure, will be aware of various possible variations of supervised machine learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

Figure 8:
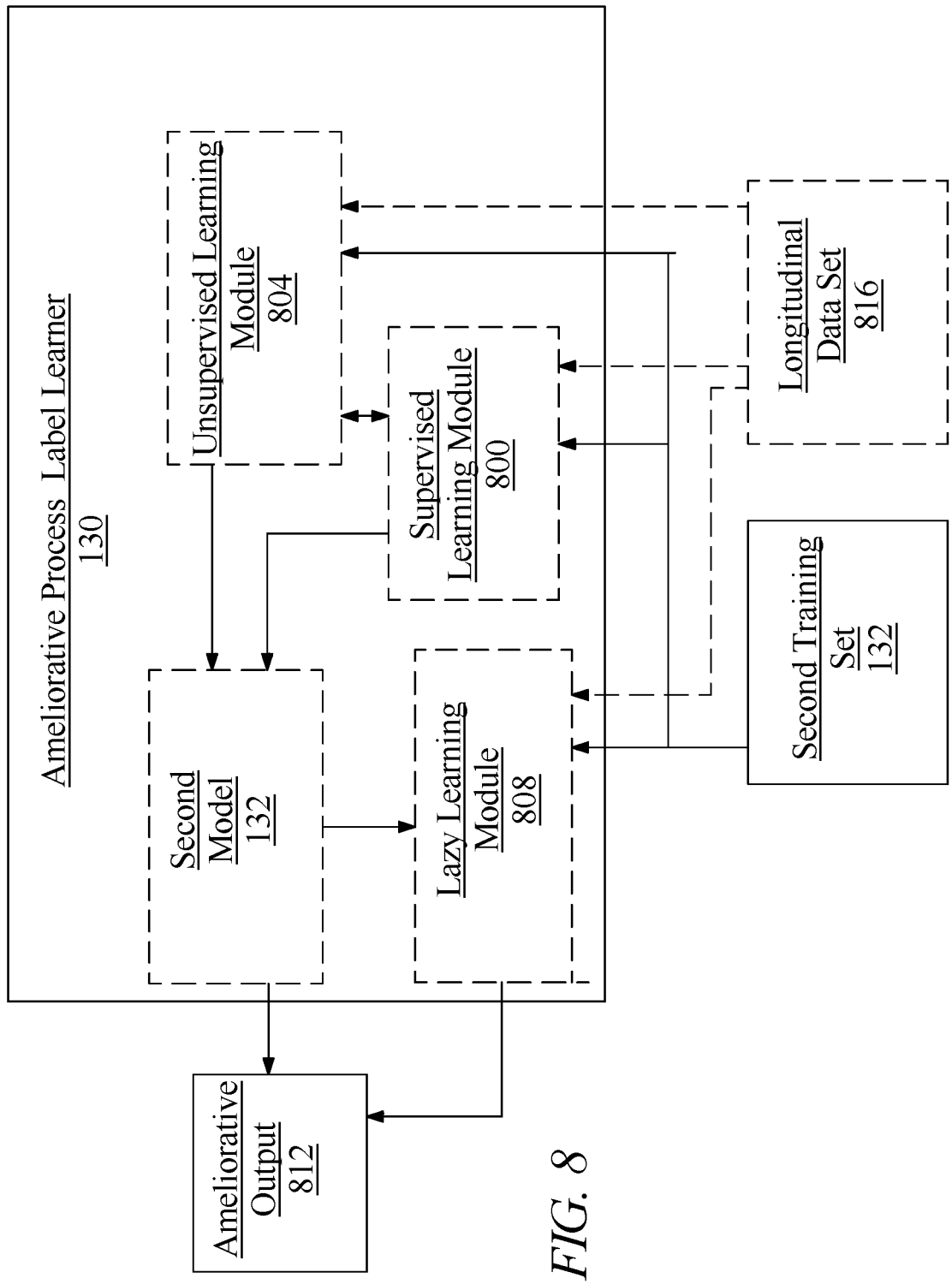
FIG. 8 is a block diagram illustrating an exemplary embodiment of an ameliorative process label learner and associated system elements.

Referring now to FIG. 8, ameliorative process label learner 130 may be configured to perform one or more supervised learning processes, as described above; supervised learning processes may be performed by a supervised learning module 800 executing on diagnostic engine 104 and/or on another computing device in communication with diagnostic engine 104, which may include any hardware or software module. For instance, a supervised learning algorithm may use prognostic labels as inputs, ameliorative labels as outputs, and a scoring function representing a desired form of relationship to be detected between prognostic labels and ameliorative labels; scoring function may, for instance, seek to maximize the probability that a given prognostic label and/or combination of prognostic labels is associated with a given ameliorative label and/or combination of ameliorative labels to minimize the probability that a given prognostic label and/or combination of prognostic labels is not associated with a given ameliorative label and/or combination of ameliorative labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of ameliorative labels, for instance because the ameliorative processes corresponding to the set of ameliorative labels are hypothesized or suspected to have an ameliorative effect on conditions represented by the prognostic labels, and/or are specified as linked to a medical specialty and/or field of medicine covering a particular set of prognostic labels and/or ameliorative labels. As a non-limiting example, a particular set prognostic labels corresponding to a set of cardiovascular conditions may be typically treated by cardiologists, and a supervised machine-learning process may be performed to relate those prognostic labels to ameliorative labels associated with various treatment options, medications, and/or lifestyle changes.

With continued reference to FIG. 8, ameliorative process label learner 130 may perform one or more unsupervised machine-learning processes as described above; unsupervised processes may be performed by an unsupervised learning module 804 executing on diagnostic engine 104 and/or on another computing device in communication with diagnostic engine 104, which may include any hardware or software module. For instance, and without limitation, ameliorative process label learner 130 and/or diagnostic engine 104 may perform an unsupervised machine learning process on second training set 116, which may cluster data of second training set 116 according to detected relationships between elements of the second training set 116, including without limitation correlations of prognostic labels to each other and correlations of ameliorative labels to each other; such relations may then be combined with supervised machine learning results to add new criteria for ameliorative process label learner 130 to apply in relating prognostic labels to ameliorative labels. As a non-limiting, illustrative example, an unsupervised process may determine that a first prognostic label 110 correlates closely with a second prognostic label 118, where the first prognostic label 110 has been linked via supervised learning processes to a given ameliorative label, but the second has not; for instance, the second prognostic label 118 may not have been defined as an input for the supervised learning process, or may pertain to a domain outside of a domain limitation for the supervised learning process. Continuing the example, a close correlation between first prognostic label 110 and second prognostic label 118 may indicate that the second prognostic label 118 is also a good match for the ameliorative label; second prognostic label 118 may be included in a new supervised process to derive a relationship or may be used as a synonym or proxy for the first prognostic label 110 by ameliorative process label learner 130. Unsupervised processes performed by ameliorative process label learner 130 may be subjected to any domain limitations suitable for unsupervised processes performed by prognostic label learner 126 as described above.

Still referring to FIG. 8, diagnostic engine 104 and/or ameliorative process label learner 130 may detect further significant categories of prognostic labels, relationships of such categories to ameliorative labels, and/or categories of ameliorative labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, ameliorative process label learner 130 and/or diagnostic engine 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 8, ameliorative labels may be generated based on classification of the at least a prognostic output. Classification as used herein includes pairing or grouping prognostic outputs as a function of some shared commonality. Prognostic outputs may be grouped with certain endocrine disorders such as diabetes, metabolic syndrome, and/or pre-diabetes which may generate an ameliorative label associated with a physical exercise recommendation that may include aerobic exercises such as running, brisk walking, cycling, and/or swimming in an attempt to reduce elevated blood sugar levels in patients with such endocrine disorders. Prognostic outputs grouped with certain alarm conditions such as chest pains, shortness of breath, cold sweat, and sudden dizziness may generate an ameliorative label associated with medical tests, diagnostics, and/or procedures for a suspected myocardial infarction such as an electrocardiogram (EKG), measurement of serum troponin levels, complete blood count (CBC), chest x-ray, echocardiogram, cardiac CT, cardiac MRI, and/or coronary catheterization. Ameliorative label may be generated based on groupings such as severity of prognostic output. For example, a user who presents with mild chest pain and some indigestion may be grouped to a category of prognostic labels that is serious but not alarming and may generate an ameliorative label that includes a blood test for troponin levels to rule out a potential myocardial infarction. A user who presents with crushing chest pain, tingling down one or both arms, shortness of breath, and cold and clammy skin may be grouped into a category of alarm so as to generate an ameliorative label that includes a cardiac CT or cardiac MRI to see if user is suffering from some type of coronary occlusion and may be a candidate for a possible coronary catheterization. In yet another non-limiting example, ameliorative label may be generated as a function of severity and/or progression of prognostic output. For example, a prognostic label that includes a diagnosis of hypothyroidism as evidenced by a thyroid stimulating level (TSH) of 6.0 (normal range is 1.4-5.5) may generate an ameliorative label that includes 150 mcg per day of iodine supplementation to lower TSH within normal limits due to mild TSH elevation and/or mild progression of hypothyroidism. A prognostic output that includes a diagnosis of hypothyroidism as evidenced by a TSH of 15.0 may generate an ameliorative label that includes 300 mcg per day of iodine supplementation as well as a prescription for a T-4 containing medication such as Synthroid and a T-3 containing medication such as Cytomel due to the more severe progression of hypothyroidism. Classification of at least a prognostic output may include staging of a prognostic label. Staging may include dividing a disease state or condition into categories on a spectrum of disease progression and symptomology. For example, a user with a prognostic output that indicates peri-menopause as evidenced by increasing prevalence of hot flashes may generate an ameliorative label that includes a recommendation for supplementation with black cohosh, while a user with a prognostic output that indicates progression to menopause as evidenced by persistent hot flashes, night sweats, absence of menstruation, dry hair, and fatigue may generate an ameliorative label that contains recommendations for supplementation with bio-identical hormone replacement therapy such as estrone (E1), estradiol (E2), estriol (E3), progesterone, testosterone, dehydroepiandrosterone (DHEA), and/or pregnenolone. In yet another non-limiting example, early stage of a disease such as Alzheimer's disease as demonstrated by mild cognitive impairment may generate an ameliorative label that includes no recommended medical treatment except for watchful waiting. However, advanced Alzheimer's disease may warrant an ameliorative label that includes medical intervention and may require a prescription medication. Ameliorative label may be generated by any of the methodologies as described below in reference to FIG. 19.

Continuing to view FIG. 8, ameliorative process label learner 130 may be configured to perform a lazy learning process as a function of the second training set 116 and the at least a prognostic output to produce the at least an ameliorative output; a lazy learning process may include any lazy learning process as described above regarding prognostic label learner 126. Lazy learning processes may be performed by a lazy learning module 808 executing on diagnostic engine 104 and/or on another computing device in communication with diagnostic engine 104, which may include any hardware or software module. Ameliorative output 812 may be provided to a user output device as described in further detail below.

In an embodiment, and still referring to FIG. 8, ameliorative process label learner 130 may generate a plurality of ameliorative labels having different implications for a particular person. For instance, where a prognostic label indicates that a person has a magnesium deficiency, various dietary choices may be generated as ameliorative labels associated with correcting the deficiency, such as ameliorative labels associated with consumption of almonds, spinach, and/or dark chocolate, as well as ameliorative labels associated with consumption of magnesium supplements. In such a situation, ameliorative process label learner 130 and/or diagnostic engine 104 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, ameliorative process label learner 130 may perform one or more lazy learning processes using a more comprehensive set of user data to identify a more probably correct result of the multiple results. Results may be presented and/or retained with rankings, for instance to advise a medical professional of the relative probabilities of various ameliorative labels being correct or ideal choices for a given person; alternatively or additionally, ameliorative labels associated with a probability of success or suitability below a given threshold and/or ameliorative labels contradicting results of the additional process, may be eliminated. As a non-limiting example, an additional process may reveal that a person is allergic to tree nuts, and consumption of almonds may be eliminated as an ameliorative label to be presented.

Continuing to refer to FIG. 8, ameliorative process label learner 130 may be designed and configured to generate further training data and/or to generate outputs using longitudinal data 816. As used herein, longitudinal data 816 may include a temporally ordered series of data concerning the same person, or the same cohort of persons; for instance, longitudinal data 816 may describe a series of blood samples taken one day or one month apart over the course of a year. Longitudinal data 816 may related to a series of samples tracking response of one or more elements of physiological data recorded regarding a person undergoing one or more ameliorative processes linked to one or more ameliorative process labels. Ameliorative process label learner 130 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given ameliorative process over time on a physiological parameter. Functions may be compared to each other to rank ameliorative processes; for instance, an ameliorative process associated with a steeper slope in curve representing improvement in a physiological data element, and/or a shallower slope in a curve representing a slower decline, may be ranked higher than an ameliorative process associated with a less steep slope for an improvement curve or a steeper slope for a curve marking a decline. Ameliorative processes associated with a curve and/or terminal data point representing a value that does not associate with a previously detected prognostic label may be ranked higher than one that is not so associated. Information obtained by analysis of longitudinal data 816 may be added to ameliorative process database and/or second training set.

Figure 9:
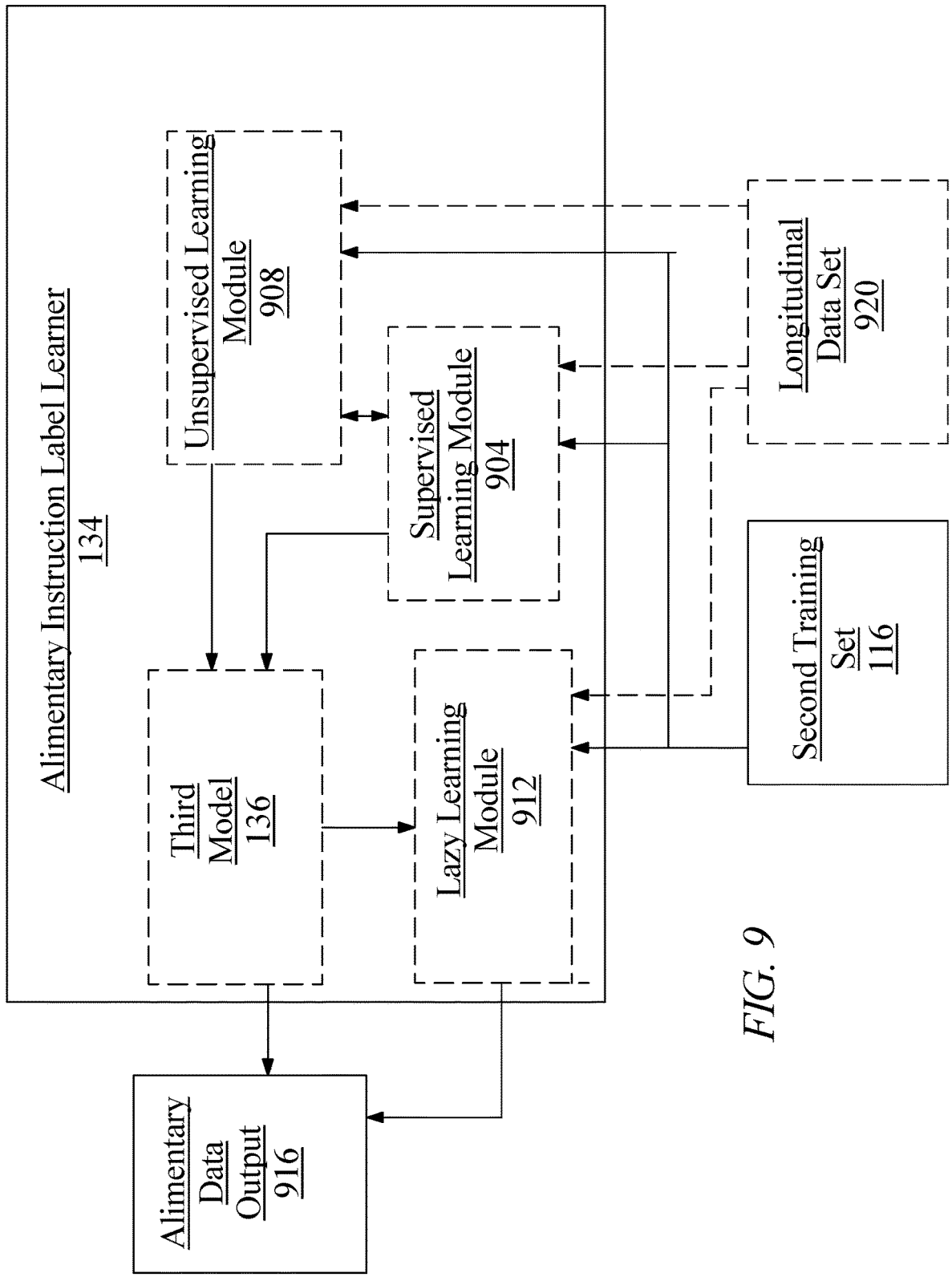
FIG. 9 is a block diagram illustrating an exemplary embodiment of an alimentary instruction label learner and associated system elements.

Referring now to FIG. 9, an exemplary embodiment of alimentary instruction label learner 134 is illustrated. alimentary instruction label learner 134 may be configured to perform one or more supervised learning processes, as described above; supervised learning processes may be performed by a supervised learning module 904 executing on diagnostic engine 104 and/or on another computing device in communication with diagnostic engine 104, which may include any hardware or software module. For instance, a supervised learning algorithm may use prognostic labels as inputs, alimentary labels as outputs, and a scoring function representing a desired form of relationship to be detected between prognostic labels and alimentary labels; scoring function may, for instance, seek to maximize the probability that a given prognostic label and/or combination of prognostic labels is associated with a given alimentary label and/or combination of alimentary labels to minimize the probability that a given prognostic label and/or combination of prognostic labels is not associated with a given alimentary label and/or combination of alimentary labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of alimentary labels, for instance because the alimentary processes corresponding to the set of alimentary labels are hypothesized or suspected to have an ameliorative effect on conditions represented by the prognostic labels, and/or are specified as linked to a medical specialty and/or field of medicine covering a particular set of prognostic labels and/or alimentary labels. As a non-limiting example, a particular set prognostic labels corresponding to a set of cardiovascular conditions may be typically treated by cardiologists, and a supervised machine-learning process may be performed to relate those prognostic labels to alimentary labels associated with various alimentary options.

With continued reference to FIG. 9, alimentary instruction label learner 134 may perform one or more unsupervised machine-learning processes as described above; unsupervised processes may be performed by an unsupervised learning module 908 executing on diagnostic engine 104 and/or on another computing device in communication with diagnostic engine 104, which may include any hardware or software module. For instance, and without limitation, alimentary instruction label learner 134 and/or diagnostic engine 104 may perform an unsupervised machine learning process on second training set 116, which may cluster data of second training set 116 according to detected relationships between elements of the second training set 116, including without limitation correlations of prognostic labels to each other and correlations of alimentary labels to each other; such relations may then be combined with supervised machine learning results to add new criteria for alimentary instruction label learner 134 to apply in relating prognostic labels to alimentary labels. As a non-limiting, illustrative example, an unsupervised process may determine that a first prognostic label 110 correlates closely with a second prognostic label 118, where the first prognostic label 110 has been linked via supervised learning processes to a given alimentary label, but the second has not; for instance, the second prognostic label 118 may not have been defined as an input for the supervised learning process, or may pertain to a domain outside of a domain limitation for the supervised learning process. Continuing the example, a close correlation between first prognostic label 110 and second prognostic label 118 may indicate that the second prognostic label 118 is also a good match for the alimentary label; second prognostic label 118 may be included in a new supervised process to derive a relationship or may be used as a synonym or proxy for the first prognostic label 110 by alimentary instruction label learner 134. Unsupervised processes performed by alimentary instruction label learner 134 may be subjected to any domain limitations suitable for unsupervised processes performed by prognostic label learner 126 as described above.

Still referring to FIG. 9, diagnostic engine 104 and/or alimentary instruction label learner 134 may detect further significant categories of prognostic labels, relationships of such categories to alimentary labels, and/or categories of alimentary labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to diagnostic engine 104, alimentary instruction label learner 134 and/or diagnostic engine 104 may continuously or iteratively perform unsupervised machine-learning processes to detect relationships between different elements of the added and/or overall data; in an embodiment, this may enable diagnostic engine 104 to use detected relationships to discover new correlations between known biomarkers, prognostic labels, and/or alimentary labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable alimentary labels. Use of unsupervised learning may greatly enhance the accuracy and detail with which system may detect prognostic labels and/or alimentary labels.

Continuing to view FIG. 9, alimentary instruction label learner 134 may be configured to perform a lazy learning process as a function of the second training set 116 and the at least a prognostic output to produce the at least an alimentary output; a lazy learning process may include any lazy learning process as described above regarding prognostic label learner 126. Lazy learning processes may be performed by a lazy learning module 912 executing on diagnostic engine 104 and/or on another computing device in communication with diagnostic engine 104, which may include any hardware or software module. Alimentary output 916 may be provided to a user output device as described in further detail below.

With continued reference to FIG. 9, alimentary instruction label learner 134 may generate a plurality of alimentary labels having different implications for a particular person. For instance, where a prognostic label indicates that a person has a magnesium deficiency, various dietary choices may be generated as alimentary labels associated with correcting the deficiency, such as alimentary labels associated with consumption of almonds, spinach, and/or dark chocolate, as well as alimentary labels associated with consumption of magnesium supplements. In such a situation, alimentary instruction label learner 134 and/or diagnostic engine 104 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, alimentary instruction label learner 134 may perform one or more lazy learning processes using a more comprehensive set of user data to identify a more probably correct result of the multiple results. Results may be presented and/or retained with rankings, for instance to advise a medical professional of the relative probabilities of various alimentary labels being correct or ideal choices for a given person; alternatively or additionally, alimentary labels associated with a probability of success or suitability below a given threshold and/or alimentary labels contradicting results of the additional process, may be eliminated. As a non-limiting example, an additional process may reveal that a person is allergic to tree nuts, and consumption of almonds may be eliminated as an alimentary label to be presented.

Continuing to refer to FIG. 9, alimentary instruction label learner 134 may be designed and configured to generate further training data and/or to generate outputs using longitudinal data 920. As used herein, longitudinal data 920 may include a temporally ordered series of data concerning the same person, or the same cohort of persons; for instance, longitudinal data 920 may describe a series of blood samples taken one day or one month apart over the course of a year. Longitudinal data 920 may relate to a series of samples tracking response of one or more elements of physiological data recorded regarding a person undergoing one or more alimentary processes linked to one or more alimentary process labels. Alimentary instruction label learner 134 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given alimentary process over time on a physiological parameter. Functions may be compared to each other to rank alimentary processes; for instance, an alimentary process associated with a steeper slope in curve representing improvement in a physiological data element, and/or a shallower slope in a curve representing a slower decline, may be ranked higher than an alimentary process associated with a less steep slope for an improvement curve or a steeper slope for a curve marking a decline. Alimentary processes associated with a curve and/or terminal data point representing a value that does not associate with a previously detected prognostic label may be ranked higher than one that is not so associated. Information obtained by analysis of longitudinal data 920 may be added to alimentary process database and/or second training set.

With continued reference to FIG. 9, embodiments of diagnostic engine 104 may furnish augmented intelligence systems that facilitate diagnostic, prognostic, curative, and/or therapeutic decisions by nutrition, diet, and wellness professionals such as nutritionists, dietitians, or applicable trainers/coaches/mentors. Diagnostic engine 104 may provide fully automated tools and resources for each applicable professional to handle, process, diagnosis, develop alimentary, diet, or wellness plans, facilitate and monitor all patient implementation, and record each patient status. Provision of expert system elements via expert inputs and document-driven language analysis may ensure that recommendations generated by diagnostic engine 104 are backed by the very best medical and alimentary knowledge and practices in the world. Models and/or learners with access to data in depth may enable generation of recommendations that are directly personalized for each patient, providing complete confidence, mitigated risk, and complete transparency. Access to well-organized and personalized knowledge in depth may greatly enhance efficiency of nutrition consultations; in embodiments, a comprehensive session may be completed in as little as 10 minutes. Recommendations may further suggest follow up testing, therapy, and/or delivery of substances, ensuring an effective ongoing treatment and prognostic plan.

Figure 10:
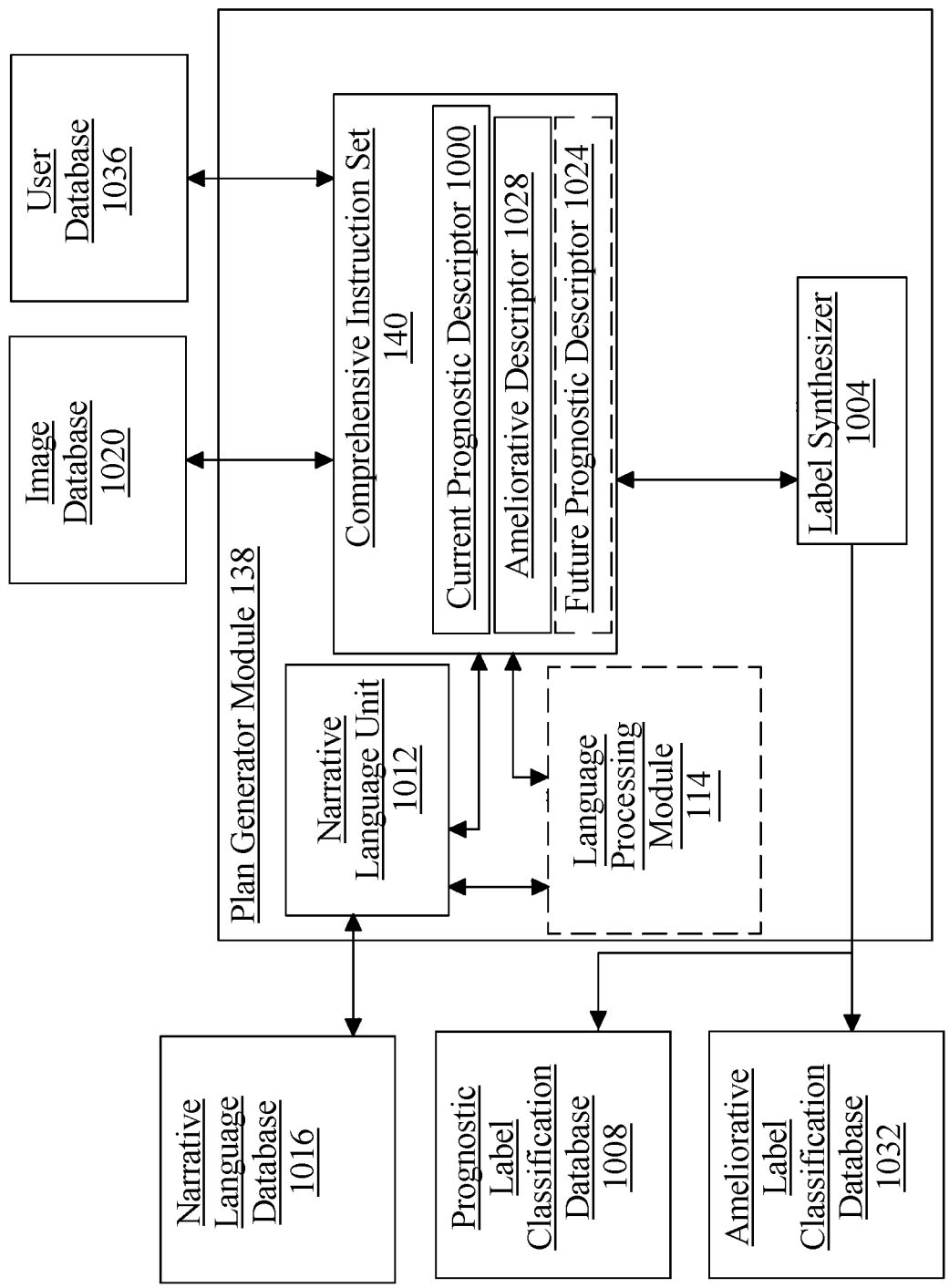
FIG. 10 is a block diagram illustrating an exemplary embodiment of a plan generator module and associated system elements.

Referring now to FIG. 10, an exemplary embodiment of a plan generator module 138 is illustrated. Comprehensive instruction set 140 includes at least a current prognostic descriptor 1000 which as used in this disclosure is an element of data describing a current prognostic status based on at least one prognostic output. Plan generator module 138 may produce at least a current prognostic descriptor 1000 using at least a prognostic output. In an embodiment, plan generator module 138 may include a label synthesizer 1004. Label synthesizer 1004 may include any suitable software or hardware module. In an embodiment, label synthesizer 1004 may be designed and configured to combine a plurality of labels in at least a prognostic output together to provide maximally efficient data presentation. Combination of labels together may include elimination of duplicate information. For instance, label synthesizer 1004 and/or a computing device 102 may be designed and configure to determine a first prognostic label of the at least a prognostic label is a duplicate of a second prognostic label of the at least a prognostic label and eliminate the first prognostic label. Determination that a first prognostic label is a duplicate of a second prognostic label may include determining that the first prognostic label is identical to the second prognostic label; for instance, a prognostic label generated from test data presented in one biological extraction of at least a biological extraction may be the same as a prognostic label generated from test data presented in a second biological extraction of at least a biological extraction. As a further non-limiting example, a first prognostic label may be synonymous with a second prognostic label, where detection of synonymous labels may be performed, without limitation, by a language processing module 114 as described above.

Continuing to refer to FIG. 10, label synthesizer 1004 may group prognostic labels according to one or more classification systems relating the prognostic labels to each other. For instance, plan generator module 138 and/or label synthesizer 1004 may be configured to determine that a first prognostic label of the at least a prognostic label and a second prognostic label of the at least a prognostic label belong to a shared category. A shared category may be a category of conditions or tendencies toward a future condition to which each of first prognostic label and second prognostic label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with prognostic labels as well. A given prognostic label may belong to a plurality of overlapping categories. Plan generator module 138 may be configured to add a category label associated with a shared category to comprehensive instruction set 140, where addition of the label may include addition of the label and/or a datum linked to the label, such as a textual or narrative description. In an embodiment, relationships between prognostic labels and categories may be retrieved from a prognostic label classification database 1008, for instance by generating a query using one or more prognostic labels of at least a prognostic output, entering the query, and receiving one or more categories matching the query from the prognostic label classification database 1008.

Figure 11:
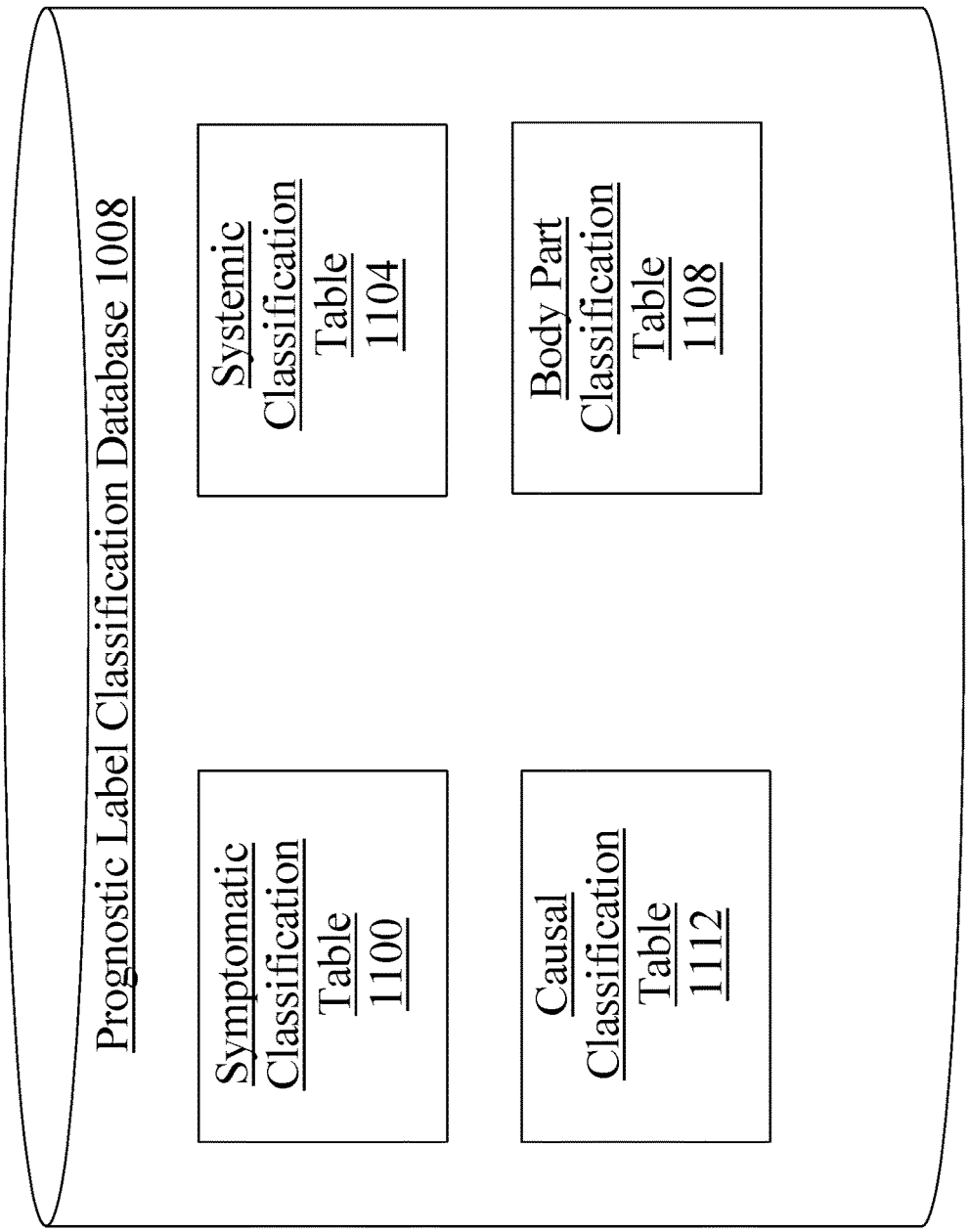
FIG. 11 is a block diagram illustrating an exemplary embodiment of a prognostic label classification database.

Referring now to FIG. 11, an exemplary embodiment of a prognostic label classification database 1008 is illustrated. Prognostic label classification database 1008 may be implemented as any database and/or datastore suitable for use as biological extraction database 200 as described above. One or more database tables in prognostic label classification database 1008 may include, without limitation, a symptomatic classification table 1200; symptomatic classification table 1200 may relate each prognostic label to one or more categories of symptoms associated with that prognostic label. As a non-limiting example, symptomatic classification table 1200 may include records indicating that each of lactose intolerance and gluten sensitivity results in symptoms including gas buildup, bloating, and abdominal pain. One or more database tables in prognostic label classification database 1108 may include, without limitation, a systemic classification table 1204; systemic classification table 1204 may relate each prognostic label to one or more systems associated with that prognostic label. As a non-limiting example, systemic classification table 1204 may include records indicating each of lactose intolerance and gluten sensitivity affects the digestive system; two digestive sensitivities linked to allergic or other immune responses may additionally be linked in systemic classification table 1204 to the immune system. One or more database tables in prognostic label classification database 1008 may include, without limitation, a body part classification table 1008; body part classification table 1208 may relate each prognostic label to one or more body parts associated with that prognostic label. As a non-limiting example, body part classification table 1208 may include records indicating each of psoriasis and rosacea affects the skin of a person. One or more database tables in prognostic label classification database 1008 may include, without limitation, a causal classification table 1212; causal classification table 1212 may relate each prognostic label to one or more causes associated with that prognostic label. As a non-limiting example, causal classification table 1212 may include records indicating each of type 2 diabetes and hypertension may have obesity as a cause. The above-described tables, and entries therein, are provided solely for exemplary purposes. Persons skilled in the art, upon reviewing the entirety of this disclosure, will be aware of various additional examples for tables and/or relationships that may be included or recorded in prognostic classification table consistently with this disclosure.

Referring again to FIG. 10, plan generator module 138 may be configured to generate current prognostic descriptor 1000 by converting one or more prognostic labels into narrative language. As a non-limiting example, plan generator module 138 may include a narrative language unit 1012, which may be configured to determine an element of narrative language associated with at least a prognostic label and include the element of narrative language in current prognostic label descriptor. Narrative language unit 1012 may implement this, without limitation, by using a language processing module 114 to detect one or more associations between prognostic labels, or lists of prognostic labels, and phrases and/or statements of narrative language. Alternatively or additionally, narrative language unit 1012 may retrieve one or more elements of narrative language from a narrative language database 1016, which may contain one or more tables associating prognostic labels and/or groups of prognostic labels with words, sentences, and/or phrases of narrative language. One or more elements of narrative language may be included in comprehensive instruction set 140, for instance for display to a user as text describing a current prognostic status of the user. Current prognostic descriptor 1000 may further include one or more images; one or more images may be retrieved by plan generator module 138 from an image database 1020, which may contain one or more tables associating prognostic labels, groups of prognostic labels, current prognostic descriptors 1000, or the like with one or more images.

With continued reference to FIG. 10, comprehensive instruction set 140 may include one or more follow-up suggestions, which may include, without limitation, suggestions for acquisition of an additional biological extraction; in an embodiment, additional biological extraction may be provided to diagnostic engine 104, which may trigger repetition of one or more processes as described above, including without limitation generation of prognostic output, refinement or elimination of ambiguous prognostic labels of prognostic output, generation of ameliorative output, and/or refinement or elimination of ambiguous ameliorative labels of ameliorative output. For instance, where a pegboard test result suggests possible diagnoses of Parkinson's disease, Huntington's disease, ALS, and MS as described above, follow-up suggestions may include suggestions to perform endocrinal tests, genetic tests, and/or electromyographic tests; results of such tests may eliminate one or more of the possible diagnoses, such that a subsequently displayed output only lists conditions that have not been eliminated by the follow-up test. Follow-up tests may include any receipt of any biological extraction as described above.

With continued reference to FIG. 10, comprehensive instruction set 140 may include one or more elements of contextual information, including without limitation any patient medical history such as current lab results, a current reason for visiting a medical professional, current status of one or more currently implemented treatment plans, biographical information concerning the patient, and the like. One or more elements of contextual information may include goals a patient wishes to achieve with a medical visit or session, and/or as result of interaction with diagnostic engine 104. Contextual information may include one or more questions a patient wishes to have answered in a medical visit and/or session, and/or as a result of interaction with diagnostic engine 104. Contextual information may include one or more questions to ask a patient. Persons skilled in the art, upon reviewing the entirety of this disclosure, will be aware of various forms of contextual information that may be included, consistently with this disclosure.

With continued reference to FIG. 10, comprehensive instruction set 140 may include at least a future prognostic descriptor 1024. As used herein, a future prognostic descriptor 1024 is an element of data describing a future prognostic status based on at least one prognostic output, which may include without limitation a desired further prognostic status. In an embodiment, future prognostic descriptor 1024 may include any element suitable for inclusion in current prognostic descriptor 1000. Future prognostic descriptor 1024 may be generated using any processes, modules, and/or components suitable for generation of current prognostic descriptor 1000 as described above.

Still referring to FIG. 10, comprehensive instruction set 140 includes at least an ameliorative process descriptor 1028, which as defined in this disclosure an element of data describing one or more ameliorative processes to be followed based on at least one ameliorative output; at least an ameliorative process descriptor 1028 may include descriptors for ameliorative processes usable to achieve future prognostic descriptor 1024. Plan generator module 138 may produce at least an ameliorative process descriptor 1028 using at least a prognostic output. In an embodiment, label synthesizer 1004 may be designed and configured to combine a plurality of labels in at least an ameliorative output together to provide maximally efficient data presentation. Combination of labels together may include elimination of duplicate information. For instance, label synthesizer 1004 and/or a computing device 102 may be designed and configure to determine a first ameliorative label of the at least an ameliorative label is a duplicate of a second ameliorative label of the at least an ameliorative label and eliminate the first ameliorative label. Determination that a first ameliorative label is a duplicate of a second ameliorative label may include determining that the first ameliorative label is identical to the second ameliorative label; for instance, a ameliorative label generated from test data presented in one biological extraction of at least a biological extraction may be the same as a ameliorative label generated from test data presented in a second biological extraction of at least a biological extraction. As a further non-limiting example, a first ameliorative label may be synonymous with a second ameliorative label, where detection of synonymous labels may be performed, without limitation, by a language processing module 114 as described above.

Continuing to refer to FIG. 10, label synthesizer 1004 may group ameliorative labels according to one or more classification systems relating the ameliorative labels to each other. For instance, plan generator module 138 and/or label synthesizer 1004 may be configured to determine that a first ameliorative label of the at least an ameliorative label and a second ameliorative label of the at least an ameliorative label belong to a shared category. A shared category may be a category of conditions or tendencies toward a future condition to which each of first ameliorative label and second ameliorative label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with ameliorative labels as well. A given ameliorative label may belong to a plurality of overlapping categories. Plan generator module 138 may be configured to add a category label associated with a shared category to comprehensive instruction set 140, where addition of the label may include addition of the label and/or a datum linked to the label, such as a textual or narrative description. In an embodiment, relationships between ameliorative labels and categories may be retrieved from an ameliorative label classification database 1032, for instance by generating a query using one or more ameliorative labels of at least an ameliorative output, entering the query, and receiving one or more categories matching the query from the ameliorative label classification database 1032.

Figure 12:
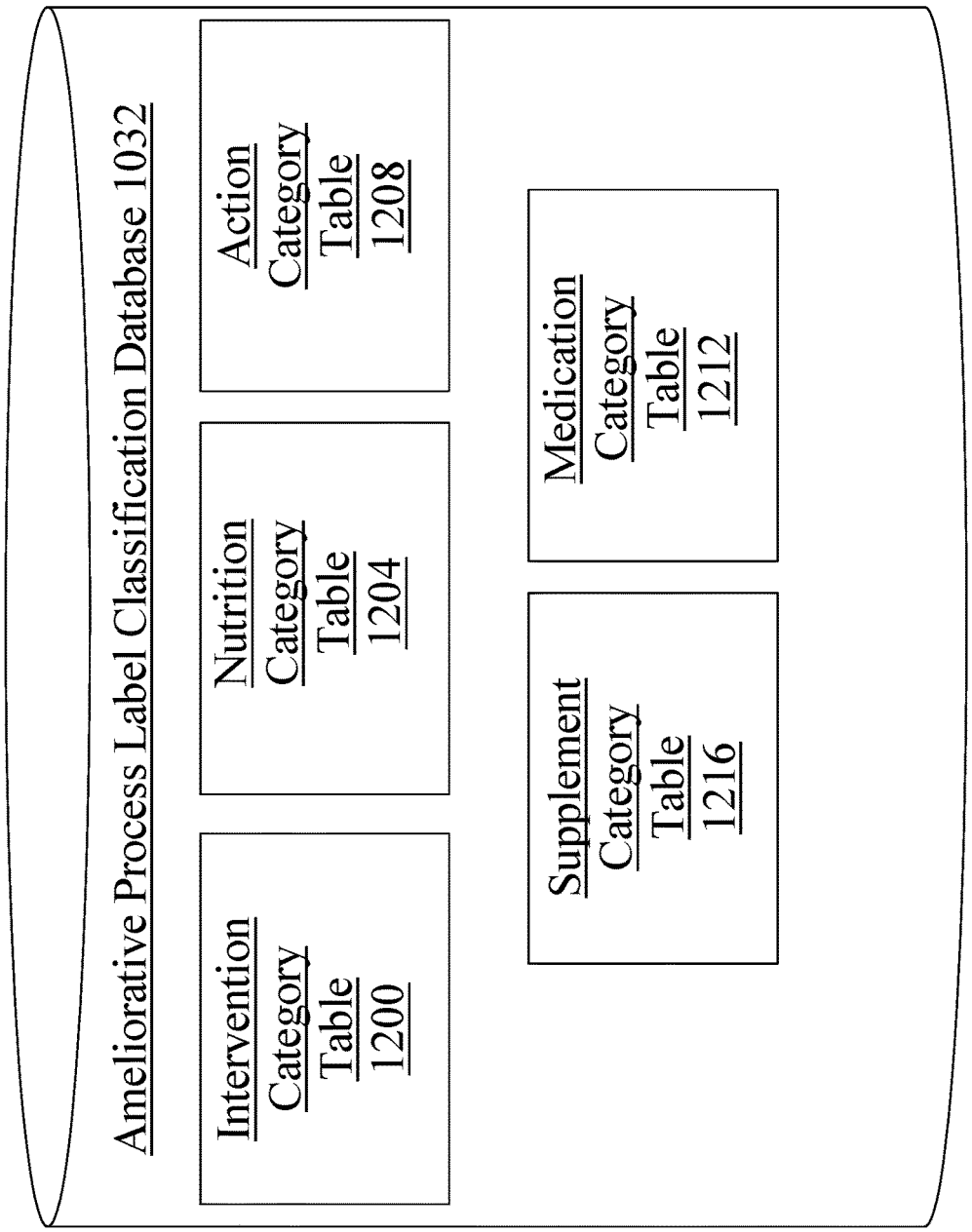
FIG. 12 is a block diagram illustrating an exemplary embodiment of an ameliorative process label classification database.

Referring now to FIG. 12, an exemplary embodiment of an ameliorative label classification database 1032 is illustrated. Ameliorative label classification database 1032 may be implemented as any database and/or datastore suitable for use as biological extraction database 200 as described above. One or more database tables in ameliorative label classification database 1032 may include, without limitation, an intervention category table 1200; intervention 1200 may relate each ameliorative label to one or more categories associated with that ameliorative label. As a non-limiting example, intervention category table 1200 may include records indicating that each of a plan to consume a given quantity of almonds and a plan to consume less meat maps to a category of nutritional instruction, while a plan to jog for 30 minutes per day maps to a category of activity. One or more database tables in ameliorative label classification database 1032 may include, without limitation, a nutrition category table 1204; nutrition category table 1204 may relate each ameliorative label pertaining to nutrition to one or more categories associated with that ameliorative label. As a non-limiting example, nutrition category table 1204 may include records indicating that each of a plan to consume more almonds and a plan to consume more walnuts qualifies as a plan to consume more nuts, as well as a plan to consume more protein. One or more database tables in ameliorative label classification database 1032 may include, without limitation, an action category table 1208; action category table 1208 may relate each ameliorative label pertaining to an action to one or more categories associated with that ameliorative label. As a non-limiting example, action category table 1208 may include records indicating that each of a plan jog for 30 minutes a day and a plan to perform a certain number of sit-ups per day qualifies as an exercise plan. One or more database tables in ameliorative label classification database 1032 may include, without limitation, a medication category table 1212; medication category table 1212 may relate each ameliorative label associated with a medication to one or more categories associated with that ameliorative label. As a non-limiting example, medication category table 1212 may include records indicating that each of a plan to take an antihistamine and a plan to take an anti-inflammatory steroid belongs to a category of allergy medications. One or more database tables in ameliorative label classification database 1032 may include, without limitation, a supplement category table 1216; supplement category table 1216 may relate each ameliorative label pertaining to a supplement to one or more categories associated with that ameliorative label. As a non-limiting example, supplement category table 1216 may include records indicating that each of a plan to consume a calcium supplement and a plan to consume a vitamin D supplement corresponds to a category of supplements to aid in bone density. Ameliorative labels may be mapped to each of nutrition category table 1204, action category table 1208, supplement category table 1216, and medication category table 1212 using intervention category table 1200. The above-described tables, and entries therein, are provided solely for exemplary purposes. Persons skilled in the art, upon reviewing the entirety of this disclosure, will be aware of various additional examples for tables and/or relationships that may be included or recorded in ameliorative classification table consistently with this disclosure.

Referring again to FIG. 10, plan generator module 138 may be configured to generate ameliorative process descriptor 1028 by converting one or more ameliorative labels into narrative language. As a non-limiting example, plan generator module 138 may include a narrative language unit 1012, which may be configured to determine an element of narrative language associated with at least an ameliorative label and include the element of narrative language in current ameliorative label descriptor. Narrative language unit 1012 may implement this, without limitation, by using a language processing module 114 to detect one or more associations between ameliorative labels, or lists of ameliorative labels, and phrases and/or statements of narrative language. Alternatively or additionally, narrative language unit 1012 may retrieve one or more elements of narrative language from narrative language database 1016, which may contain one or more tables associating ameliorative labels and/or groups of ameliorative labels with words, sentences, and/or phrases of narrative language. One or more elements of narrative language may be included in comprehensive instruction set 140, for instance for display to a user as text describing a current ameliorative status of the user. Ameliorative process descriptor 1028 may further include one or more images; one or more images may be retrieved by plan generator module 138 from an image database 1020, which may contain one or more tables associating ameliorative labels, groups of ameliorative labels, ameliorative process descriptors 1028, or the like with one or more images.

Figure 13:
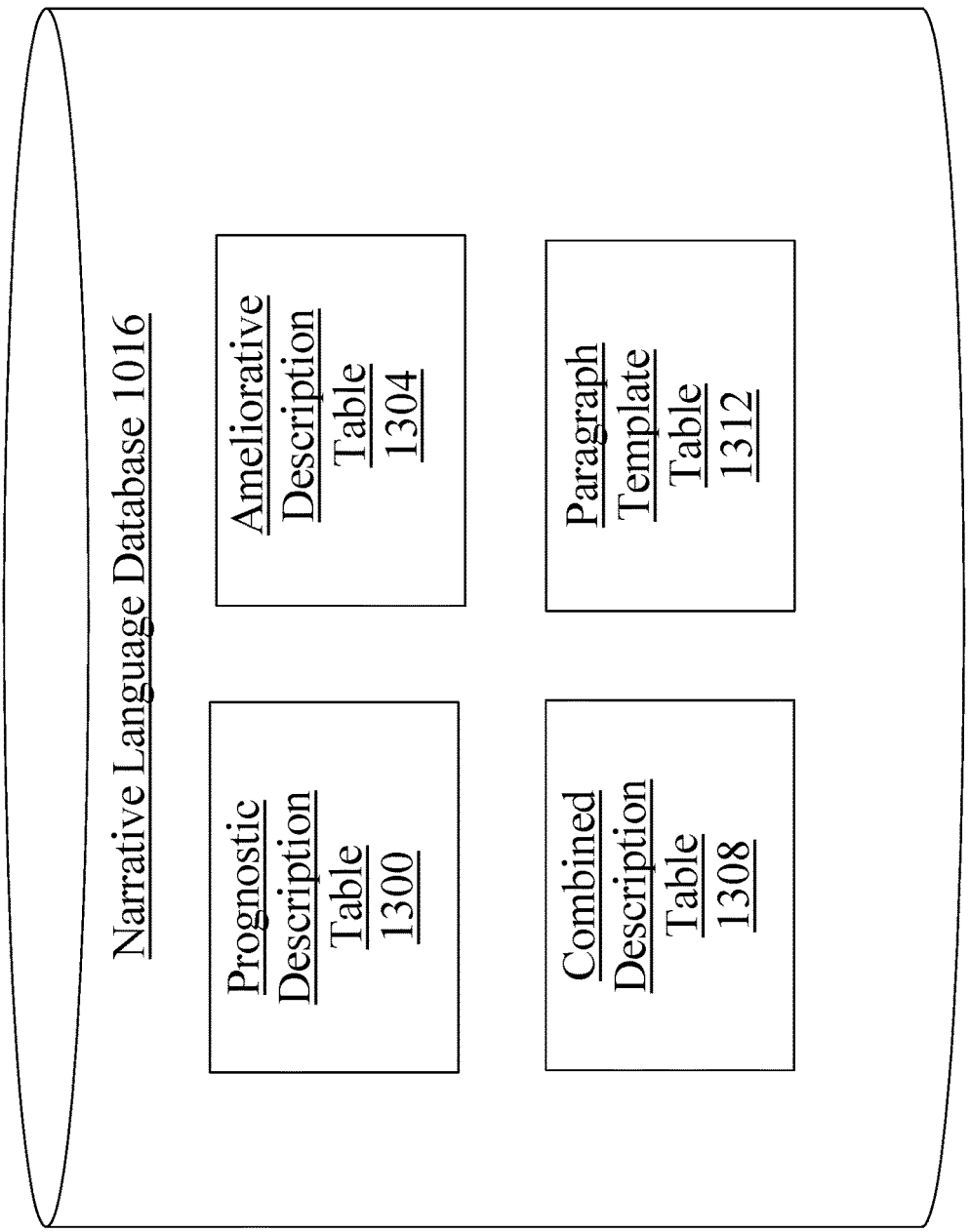
FIG. 13 is a block diagram illustrating an exemplary embodiment of a narrative language database.

Referring now to FIG. 13, and exemplary embodiment of a narrative language database 1016 is illustrated. Narrative language database 1016 may be implemented as any database and/or datastore suitable for use as biological extraction database 200 as described above. One or more database tables in narrative language database 1016 may include, without limitation, a prognostic description table 1300, which may link prognostic labels to narrative descriptions associated with prognostic labels. One or more database tables in narrative language database 1016 may include, without limitation, an ameliorative description table 1304, which may link ameliorative process labels to narrative descriptions associated with ameliorative process labels. One or more database tables in narrative language database 1016 may include, without limitation, a combined description table 1308, which may link combinations of prognostic labels and ameliorative labels to narrative descriptions associated with the combinations. One or more database tables in narrative language database 1016 may include, without limitation, a paragraph template table 1312, which may contain one or more templates of paragraphs, pages, reports, or the like into which images and text, such as images obtained from image database 1020 and text obtained from prognostic description table 1300, ameliorative description table 1304, and combined description table 1308 may be inserted. Tables in narrative description table 1016 may be populated, as a non-limiting example, using submissions from experts, which may be collected according to any processes described above. Persons skilled in the art, upon reviewing the entirety of this disclosure, will be aware of various way sin which entries in narrative description table 1016 may be categorized and/or organized.

Figure 14:
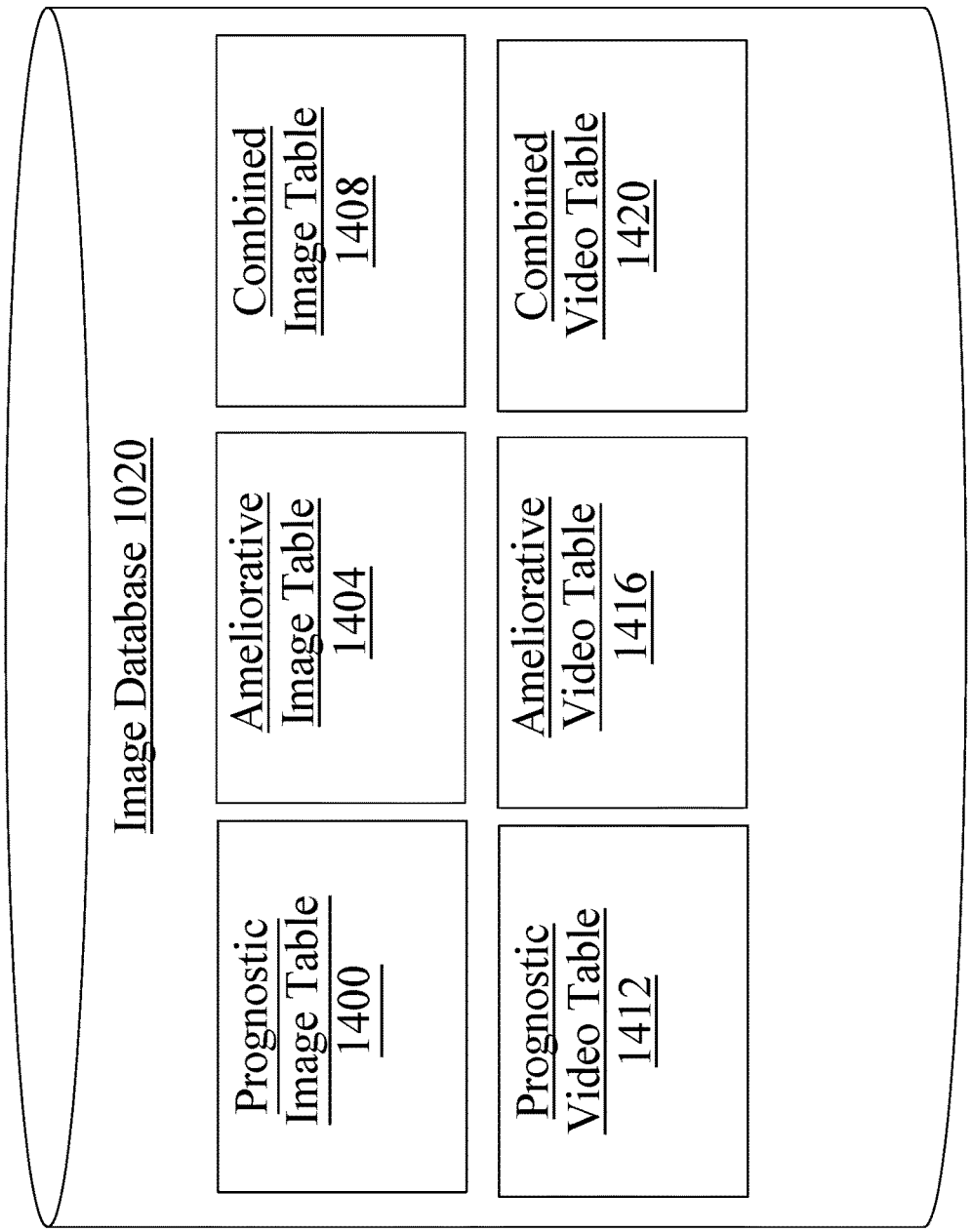
FIG. 14 is a block diagram illustrating an exemplary embodiment of an image database.

Referring now to FIG. 14, an exemplary embodiment of an image database 1020 is illustrated. Image database 1020 may be implemented as any database and/or datastore suitable for use as biological extraction database 200 as described above. One or more database tables in image database 102 may include, without limitation, a prognostic image table 1400, which may link prognostic labels to images associated with prognostic labels. One or more database tables in image database 1020 may include, without limitation, an ameliorative image table 1404, which may link ameliorative process labels to images associated with ameliorative process labels. One or more database tables in image database 1020 may include, without limitation, a combined description table 1408, which may link combinations of prognostic labels and ameliorative labels to images associated with the combinations. One or more database tables in image database 102 may include, without limitation, a prognostic video table 1412, which may link prognostic labels to videos associated with prognostic labels. One or more database tables in image database 1020 may include, without limitation, an ameliorative video table 1416, which may link ameliorative process labels to videos associated with ameliorative process labels. One or more database tables in image database 1020 may include, without limitation, a combined video table 1420, which may link combinations of prognostic labels and ameliorative labels to videos associated with the combinations. Tables in image database 1020 may be populated, without limitation, by submissions by experts, which may be provided according to any process or process steps described in this disclosure for collection of expert submissions.

Referring again to FIG. 10, plan generator module 138 may be configured to receive at least an element of user data and filter diagnostic output using the at least an element of user data. At least an element of user data, as used herein, is any element of data describing the user, user needs, and/or user preferences. At least an element of user data may include a constitutional restriction. At least a constitutional restriction may include any health-based reason that a user may be unable to engage in a given ameliorative process; at least a constitutional restriction may include any counter-indication as described above, including an injury, a diagnosis of something preventing use of one or more ameliorative processes, an allergy or food-sensitivity issue, a medication that is counter-indicated, or the like. At least an element of user data may include at least a user preference. At least a user preference may include, without limitation, any preference to engage in or eschew any ameliorative process and/or other potential elements of a comprehensive instruction set 140, including religious preferences such as forbidden foods, medical interventions, exercise routines, or the like.

Figure 15:
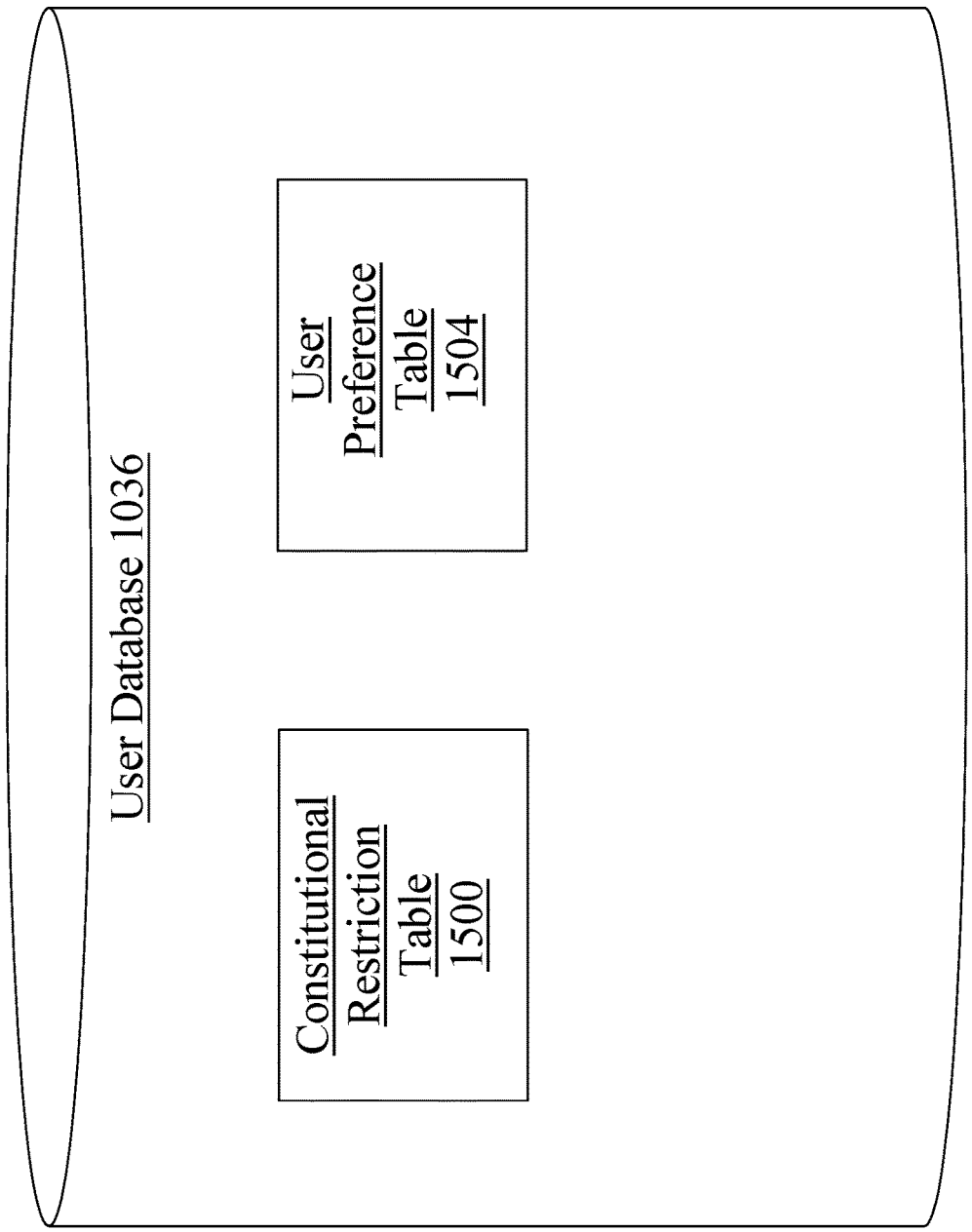
FIG. 15 is a block diagram illustrating an exemplary embodiment of a user database.

Referring to FIG. 15, an exemplary embodiment of a user database 1036 is illustrated. User database 1036 may be implemented as any database and/or datastore suitable for use as described above. One or more database tables in user database 1036 may include, without limitation, a constitution restriction table 1500; at least a constitutional restriction may be linked to a given user and/or user identifier in a constitutional restriction table 1500. One or more database tables in user database 1036 may include, without limitation, a user preference table 1504; at least a user preference may be linked to a given user and/or user identifier in a user preference table 1504.

Figure 16:
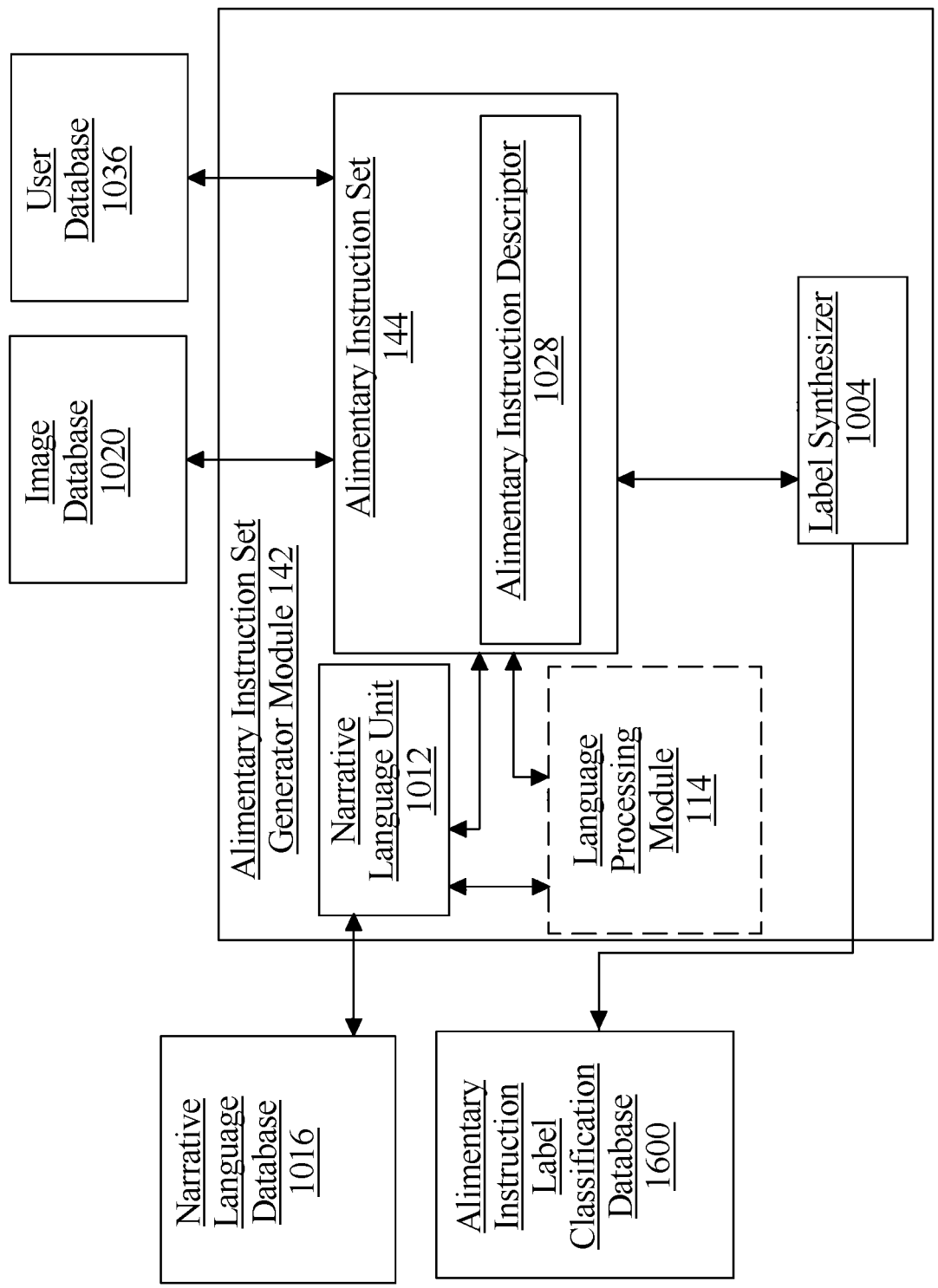
FIG. 16 is a block diagram illustrating an exemplary embodiment of an alimentary instruction set module and associated system elements.

Referring now to FIG. 16, an exemplary embodiment of alimentary instruction set module 142 is illustrated. In one embodiment, the alimentary instruction set generator module 142 may be configured to generate an alimentary instruction set comprising a plurality of information reflecting a comprehensive list of meals, supplements, and processes aimed towards resolving any identified issues, suggestions, or deficiencies as a function of the comprehensive instruction set 140. Alimentary instruction set generator module 142 may produce at least an alimentary instruction set process descriptor 1028 using at least an alimentary instruction set output. In an embodiment, alimentary instruction set generator module may include a label synthesizer 1004 as described above.

In one embodiment, and still referring to FIG. 16, the alimentary instruction set may be transmitted to a user via a graphical user interface coupled to user client device 156 associated with user operating in or subscribing to network 100. Alimentary instruction set 144 may be utilized to aid a user in performing alimentary instruction set 144 through self-fulfilling to achieve and/or maintain vibrant constitution. Self-fulfillment may include any food preparation, consuming food through food delivery, arranging for a vitamin/supplement coaching service, constitutional supplement delivery service, grocery shopping, arranging grocery delivery, picking up take-out from a food preparation center, buying a carry away meal at a grocery store or health food store, preparing a meal kit, cooking a meal from scratch in one's home, having a chef deliver and/or prepare a meal at a user's home or work, and the like.

Continuing to refer to FIG. 16, alimentary instruction set generator module 142 is designed and configured to an alimentary instruction set 144 based on comprehensive instruction set 140. In an embodiment, alimentary instruction set generator module 142 may generate alimentary instruction set 144 based on the integration of data associated with comprehensive instruction set 140, any applicable external sources, and any applicable database within system 100 or physical performance entity network 302. Generation of alimentary instruction set 144 may include identification of one or more alimentary instructions in comprehensive instruction set, and insertion of the one or more alimentary instructions in the alimentary instruction set 144; for instance, alimentary instruction set 144 may be formed, wholly or partially, by aggregating alimentary instructions from comprehensive instruction set 140 and combining the aggregated alimentary instructions using narrative language module, narrative language database, image database, or the like, according to any process suitable for generation of comprehensive instruction set as described above.

With continued reference to FIG. 16, alimentary instruction set generator module 142 may generate alimentary instruction set 144 based on alimentary data and non-alimentary data in order to facilitate both medicinal and holistic components in alimentary instruction set 144 specific to a user. In one embodiment, alimentary data may be identified and aggregated into a subset of applicable alimentary data based on at least a biological extraction and comprehensive instruction set 140. In application, alimentary instruction set 144 may comprise a plurality of alimentary data specific to user that is able to be used by machine learning and artificial intelligence systems in order to continuously update or modify training sets, and ultimately comprehensive instruction set 140 and alimentary instruction set 144 based on updated or progressions associated with implementation of alimentary instruction set 144 by user. Alimentary data and non-alimentary data may include compilations of instruction sets received over a period of time, the compilations may account for improvements or modifications associated with user. Alimentary instruction set 144 may further include instructions over time, in which the alimentary instructions may change in response to changes in a user's data and/or prognosis. Alternatively or additionally, system 100 may periodically iterate through one or more processes as described in this disclosure, such that repeated reevaluations may modify alimentary instruction set 144 as information concerning user and/or biological extractions obtained from the user change over time.

With continued reference to FIG. 16, alimentary instruction set generator module 142 may identify a non-alimentary instruction within comprehensive instruction set 140, determine an alimentary analog to the non-alimentary instruction and introduce the alimentary analog into the alimentary instruction set and/or use the alimentary analog to update the self-fulfillment instruction set. An alimentary analog, as used herein, is an alimentary process or instruction that achieves a similar purpose to a non-alimentary process and/or instruction. As a non-limiting example, certain foods such as grapefruit may act to lower blood sugar; where the impact of consuming a particular quantity of such foods is similar to or the same as an impact of consuming a blood sugar medication, the former may be an alimentary analog of the latter. In one embodiment, non-alimentary data within comprehensive instruction set 140 may be subsequently substituted in alimentary instruction set 144 with alimentary data configured to provide user with holistic solutions to issues that were initially treated with non-holistic approaches. For example, if initially diagnostic output indicates that the blood sugar of user is abnormally high then comprehensive instruction set 140 may recommend that user take applicable medications classified as non-alimentary in order to lower the blood sugar immediately. However, alimentary instruction set 144 may subsequently or concurrently provide one or more sets of instructions to remedy the improved blood sugar of user via an alimentary solution such as increased consumption of grapefruits, configured to be executed by a user. As a further example, a supplement initially presented in comprehensive instruction set 140 may be subsequently replaced, in alimentary instruction set 144, by a specific food categorized as alimentary in order to remedy the issues in which the initial supplement sought to address. In another example, alimentary data and alimentary solutions may be incorporated into alimentary instruction set 144 upon one or more determinations that the alimentary data and implementations of the alimentary solution are more efficient than non-alimentary solutions initially included in alimentary instruction set 144. Alimentary data and alimentary solutions may also be substituted for less efficient alimentary solutions. For example, if user, based on comprehensive instruction set 140, is deemed to need a boost in HDL, then a secondary alimentary solution of eating certain foods may be determined more efficient than a primary alimentary solution of increasing cardio activity.

Still referring to FIG. 16, alimentary instruction set generator module 142 may generate alimentary instruction set 144, at least in part, by identifying at least a negative effect associated with an ameliorative instruction of comprehensive instruction set 140; at least a negative effect may include a "side-effect" of an ameliorative process, such as a side effect of a medication, an increase risk of a type of injury associated with an exercise program, or the like. Alimentary instruction set generator module 142 may determine an alimentary instruction that alleviates the at least a negative effect; for instance, a side-effect of a medication may be alleviated and/or prevented by consumption of an alimentary element tending to alleviate the side-effect. As a non-limiting example, a medication that may cause fluid retention and edema may be provided in comprehensive instruction set 140; alimentary instruction set generator module 142 may determine that consumption of an alimentary element having a diuretic effect, such as a food or drink containing caffeine, may act to prevent or alleviate fluid retention. As a further non-limiting example, comprehensive instruction set 140 may include an instruction for a user to increase his or her exercise regimen, or to begin a new regimen of regular exercise; a counterindication and/or other element of data may indicate an elevated risk of joint injury and/or inflammation as a result of the increased exercise, which may be alleviated or prevented by a lower-calorie diet, consumption of foods containing glucosamine or some other ingredient associated with a reduced risk of joint pain.

Continuing to refer to FIG. 16, alimentary instruction set generator module 142 may determine an alimentary instruction that alleviates the at least a negative effect using machine-learning processes and/or modules as described above; for instance, and without limitation, alimentary instruction set generator module 142 may provide at least a negative effect to ameliorative process label learner and/or alimentary instruction set label leaner in the form of at least a prognostic label; ameliorative process label learner and/or alimentary instruction set label leaner may generate one or more ameliorative labels associated with an alimentary process for alleviating the at least a negative effect.

Continuing to refer to FIG. 16, label synthesizer 1004 may group alimentary labels according to one or more classification systems relating the alimentary labels to each other. For instance, plan generator module 138 and/or label synthesizer 1004 may be configured to determine that a first alimentary label of the at least an alimentary label and a second alimentary label of the at least an alimentary label belong to a shared category. A shared category may be a category of alimentary elements to which each of first alimentary label and second alimentary label belongs; for instance, a first alimentary label associated with tofu and a second alimentary label associated with nuts may each be grouped as a protein source. A given ameliorative label may belong to a plurality of overlapping categories. Plan generator module 138 may be configured to add a category label associated with a shared category to alimentary instruction set 144, where addition of the label may include addition of the label and/or a datum linked to the label, such as a textual or narrative description.

With continued reference to FIG. 16, label synthesizer 1004 may be designed and configured to combine a plurality of labels in at least the alimentary instruction set output together to provide maximally efficient data presentation. Combination of labels together may include elimination of duplicate information. For instance, label synthesizer 1004 and/or a computing device 102 may be designed and configure to determine a first alimentary instruction set label of the at least an alimentary instruction set label is a duplicate of a second alimentary instruction set label of the at least a alimentary instruction set label and eliminate the first alimentary instruction set label. Determination that a first alimentary instruction set label is a duplicate of a second alimentary instruction set label may include determining that the first alimentary instruction set label is identical to the second alimentary instruction set label; for instance, a alimentary instruction set label generated from test data presented in one biological extraction of at least a biological extraction may be the same as a alimentary instruction set label generated from test data presented in a second biological extraction of at least a biological extraction. As a further non-limiting example, a first alimentary instruction set label may be synonymous with a second alimentary instruction set label, where detection of synonymous labels may be performed, without limitation, by a language processing module 114 as described above.

In one embodiment, and still referring to FIG. 16, label synthesizer 1004 may group alimentary instruction set labels according to one or more classification systems relating the alimentary instruction set labels to each other. For instance, plan generator module 138 and/or label synthesizer 1004 may be configured to determine that a first alimentary instruction set label of the at least an alimentary instruction set label and a second alimentary instruction set label of the at least a alimentary instruction set label belong to a shared category. A shared category may be a category of conditions or tendencies toward a future condition to which each of first alimentary instruction set label and second alimentary instruction set label belongs; as an example, lactose intolerance and gluten sensitivity may each be examples of digestive sensitivity, for instance, which may in turn share a category with food sensitivities, food allergies, digestive disorders such as celiac disease and diverticulitis, or the like. Shared category and/or categories may be associated with alimentary instruction set labels as well. A given alimentary instruction set label may belong to a plurality of overlapping categories. Plan generator module 138 may be configured to add a category label associated with a shared category to comprehensive instruction set 140, where addition of the label may include addition of the label and/or a datum linked to the label, such as a textual or narrative description. In an embodiment, relationships between alimentary instruction set labels and categories may be retrieved from an alimentary instruction set label classification database 1600, for instance by generating a query using one or more alimentary instruction set labels of at least a alimentary instruction set output, entering the query, and receiving one or more categories matching the query from the alimentary instruction set label classification database 1600. In one embodiment, the alimentary instruction set label classification database 1600 is configured to generate queries based on preferences of user. Preferences may be based upon religious, dietary (vegan/gluten-free), lifestyle, or any other applicable factor associated with user that is able to be manifested in the alimentary instruction set.

With continued reference to FIG. 16, in one embodiment, alimentary instruction set generator module 142 may be configured to generate alimentary instruction set process descriptor 1028 by converting one or more alimentary instruction set labels into narrative language. As a non-limiting example, plan generator module 168 may include and/or communicate with narrative language unit 1012, which may be configured to determine an element of narrative language associated with at least an alimentary instruction set label and include the element of narrative language in current alimentary instruction set label descriptor. Narrative language unit 1012 may implement this, without limitation, by using a language processing module 114 to detect one or more associations between alimentary instruction set labels, or lists of alimentary instruction set labels, and phrases and/or statements of narrative language. Alternatively or additionally, narrative language unit 1012 may retrieve one or more elements of narrative language from narrative language database 1016, which may contain one or more tables associating alimentary instruction set labels and/or groups of alimentary instruction set labels with words, sentences, and/or phrases of narrative language. One or more elements of narrative language may be included in alimentary instruction set, for instance for display to a user as text describing a current alimentary instruction set status of the user. Alimentary instruction set process descriptor 1028 may further include one or more images; one or more images may be retrieved by plan generator module 138 from an image database 1120, which may contain one or more tables associating alimentary instruction set labels, groups of alimentary instruction set labels, alimentary instruction set process descriptors 1028, or the like with one or more images.

With continued reference to FIG. 16, in an embodiment, relationships between alimentary labels and categories may be retrieved from an alimentary instruction label classification database 1600, for instance by generating a query using one or more alimentary labels of at least an alimentary output, entering the query, and receiving one or more categories matching the query from the alimentary instruction label classification database 1600.

Figure 17:
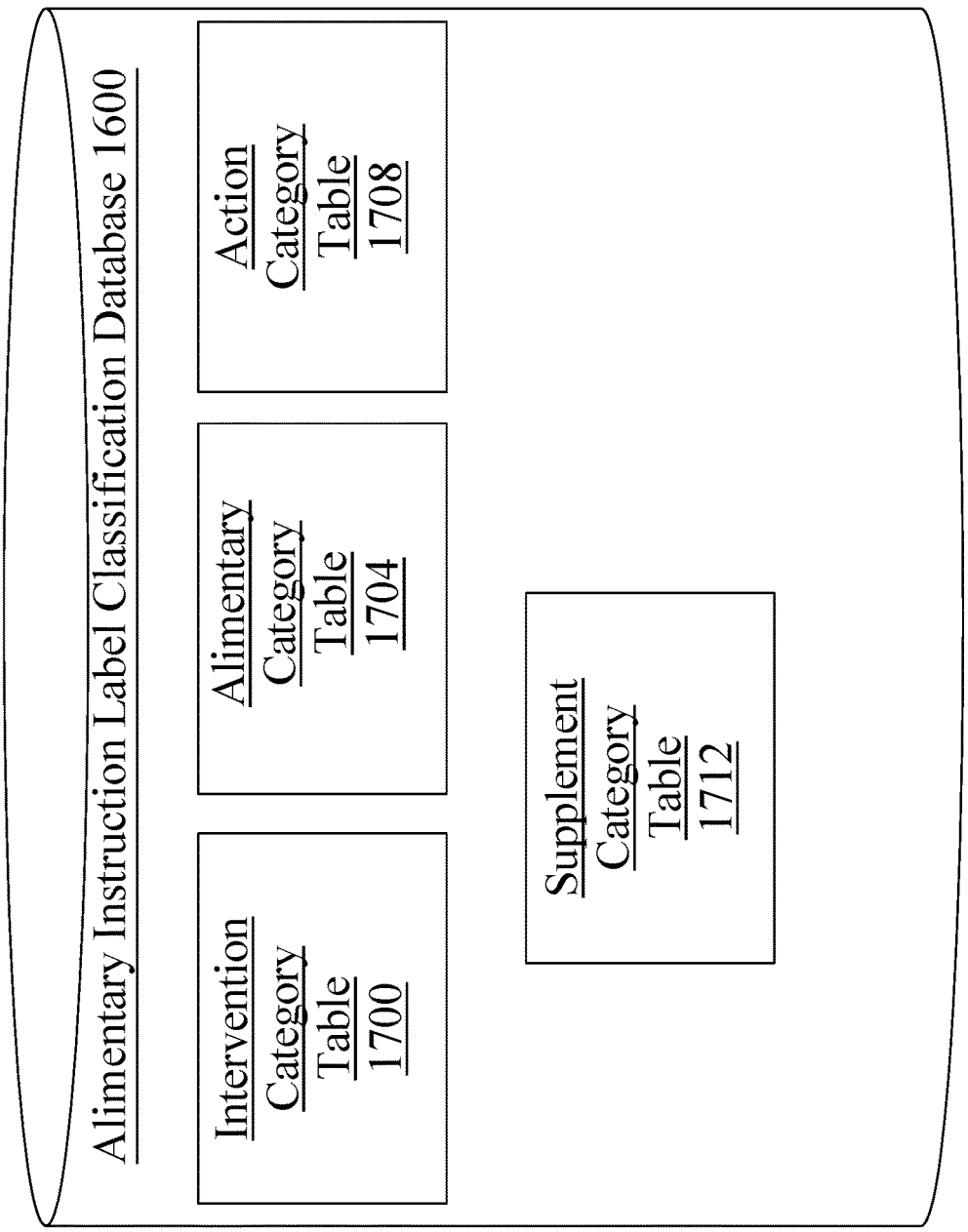
FIG. 17 is a block diagram illustrating an exemplary embodiment of an alimentary instruction label classification database.

Referring now to FIG. 17, an exemplary embodiment of an alimentary instruction label classification database 1700 is illustrated. Alimentary instruction label classification database 1700 may operate on the diagnostic engine 104. Alimentary instruction label classification database 1700 may be implemented as any database and/or datastore suitable for use as a database. One or more database tables in alimentary instruction label classification database 1700 may include, without limitation, an intervention category table 1700; an intervention may relate each alimentary label to one or more categories of conditions to be addressed by an alimentary instruction associated with that alimentary label, such as a nutritional imbalance to be corrected or the like. One or more database tables in alimentary instruction label classification database 1700 may include, without limitation, an alimentary category table 1704; which may associate an alimentary instruction label with one or more categories of nutritional properties, foodstuffs, or the like. One or more database tables in alimentary instruction label classification database 1700 may include, without limitation, an action category table 2508, which may describe one or more categories of actions, such as calorie reduction, sugar intake reduction, or the like, to which a given alimentary instruction may belong. One or more database tables in alimentary instruction label classification database 1700 may include, without limitation, a supplement table 2512, which may describe a supplement that relates to a nutritional need filled by an alimentary instruction.

Figure 18:
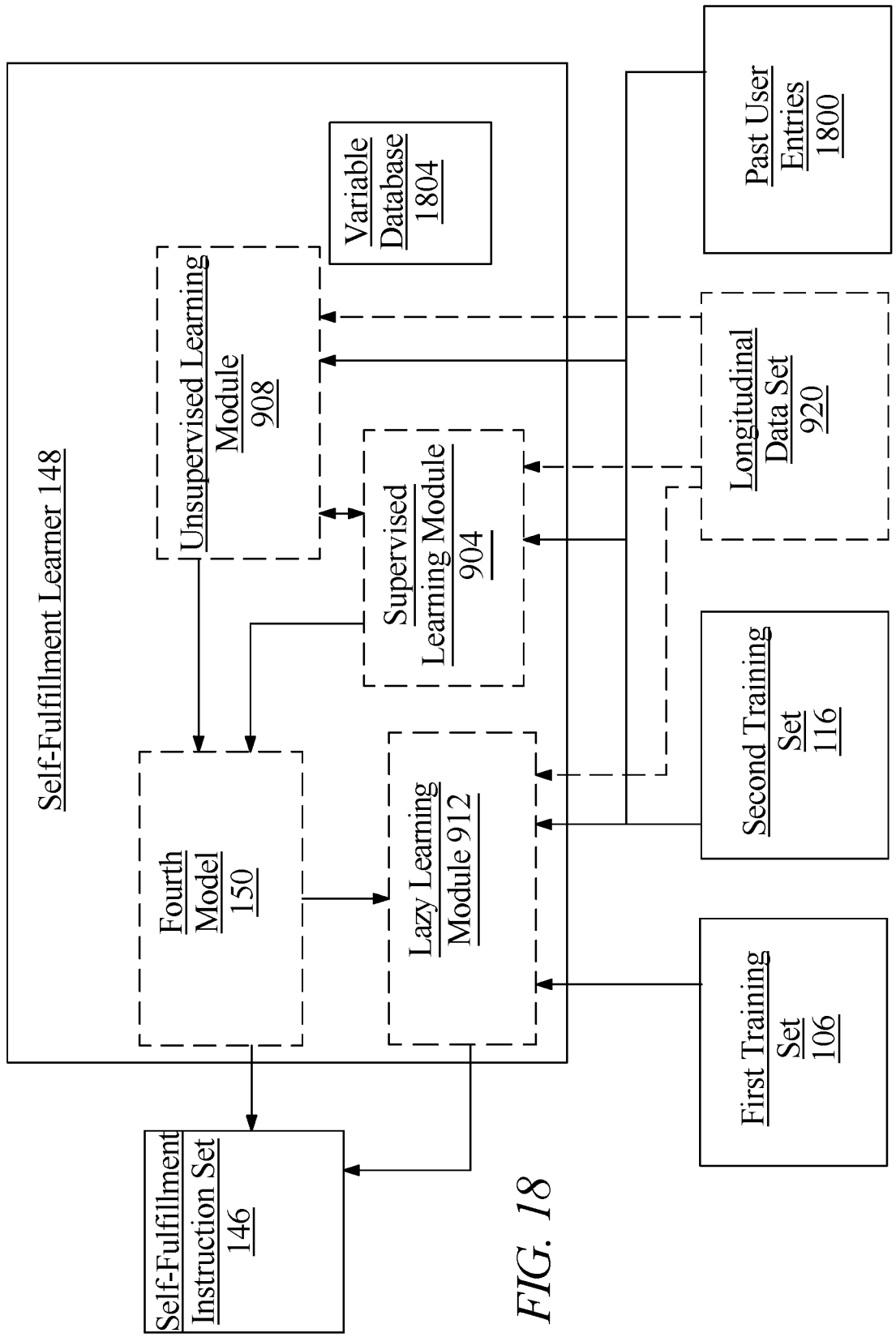
FIG. 18 is a block diagram illustrating an exemplary embodiment of a self-fulfillment learner and associated system elements.

Referring now to FIG. 18, an exemplary embodiment of self-fulfillment learner 148 is illustrated. Self-fulfillment learner 148 may be configured to perform one or more supervised learning processes, as described above; supervised learning processes may be performed by a supervised learning module 904 executing on diagnostic engine 104 and/or on another computing device in communication with diagnostic engine 104, which may include any hardware or software module. For example, supervised learning algorithm may use alimentary instruction set as inputs, and user entries containing an alimentary self-fulfillment action as outputs and/or self-fulfillment instruction set as output and a scoring function representing a desired form of relationship to be detected between alimentary self-fulfillment action and alimentary instruction sets; scoring function may, for instance, seek to maximize the probability that a given alimentary instruction set is associated with an alimentary self-fulfillment action. In yet another non-limiting example, supervised learning algorithm may use self-fulfillment instruction set as inputs and user entries containing an alimentary self-fulfillment action as output and a scoring function representing a desired form of relationship to be detected between alimentary self-fulfillment action and self-fulfillment instruction sets; scoring function may, for instance seek to maximize the probability that a given self-fulfillment instruction set is associated with an alimentary self-fulfillment action. In an embodiment, one or more supervised machine-learning algorithms may be restricted to a particular domain; for instance, a supervised machine-learning process may be performed with respect to a given set of parameters and/or categories of self-fulfillment instruction sets that have been suspected to be related to a given set of user entries containing an alimentary self-fulfillment action for instance because the user entries containing an alimentary self-fulfillment action corresponding to the self-fulfillment instruction set are hypothesized or suspected to be linked to a field of actions or group of actions. For example, a particular set of self-fulfillment instruction sets relating to obtaining groceries such as creating grocery lists, ordering groceries, shopping for groceries, and putting groceries away may all relate to obtaining groceries, and a supervised machine-learning process may be performed to relate these self-fulfillment actions to those contained within a self-fulfillment instruction set.

With continued reference to FIG. 18, self-fulfillment learner 148 may perform one or more supervised machine-learning processes as described above, including a loss function analysis utilizing linear regression based on past user interactions with system 100, such as information collected from user entries and alimentary instruction sets and/or self-fulfillment instruction sets. Loss function analysis may use supervised machine-learning processes and algorithms to iterate and converge towards a minimum where further tweaks to the variables produce little or zero changes in the loss or convergence by optimizing weights utilized by machine learning algorithms. Self-fulfillment learner 148 may utilize variables to model relationships between past interactions between a user such as previously generated user entries and self-fulfillment instruction sets and/or alimentary instruction sets. Loss function analysis may utilize variables that may be weighted and adjusted to predict outcomes. Variables may be personalized based on user inputs and weighted based on user inputs. For example, a user may weight one variable as being more important than another while another user may attribute equal weight to each variable. Variables may be contained with a variables database 1804 as described in more detail below in reference to FIG. 19. Loss function analysis may utilize past user entries 1800 to generate outputs such as self-fulfillment instruction set 146. Past user entries 1800 may include any information pertaining to user's previous interactions with system 100. Past user entries 1800 may include for example, previous user entries containing self-fulfillment actions, previous self-fulfillment instruction sets generated for a user, previous prognostic labels, previous ameliorative process labels, and/or previously alimentary instruction sets generated for a user.

With continued reference to FIG. 18, self-fulfillment learner 148 may utilize linear loss function algorithms customized around a user and based on user entries and past user performances to more accurately generate an alimentary instruction set 144 for a user, a self-fulfillment instruction set 146 for a user, and/or to update information and training sets utilized by plan generator module 138. Loss function algorithms may utilize weighted variables customized to a user. Loss function algorithms may minimize distance between variables and may seek to minimize distance variable to variable. In an embodiment, after a user has submitted a user entry, the loss function may be re-run and updated. For example, if a user found a certain ingredient at a grocery store then self-fulfillment instruction set may be re-generated to update based on this development. Loss function algorithms may utilize weighted variables that are customized to a user. For example, user entries that contain trends and patterns as to self-fulfillment actions may be utilized by self-fulfillment learner to generate self-fulfillment instruction sets based on user trends and patterns to self-fulfill. For example, a user who enters user entries that show a frequency of cooking meals at home may be utilized by self-fulfillment learner 148 to generate self-fulfillment instruction sets that include recipes for the user or suggestions as to potential new ingredients to try. In yet another non-limiting example, a user who enters user entries that show a frequency of eating out at restaurants may be utilized by self-fulfillment learner 148 to generate self-fulfillment instruction sets that contain very basic recipes to prepare at home or that contain recommendations as to where a user can buy a meal on the go in user's area.

Figure 19:
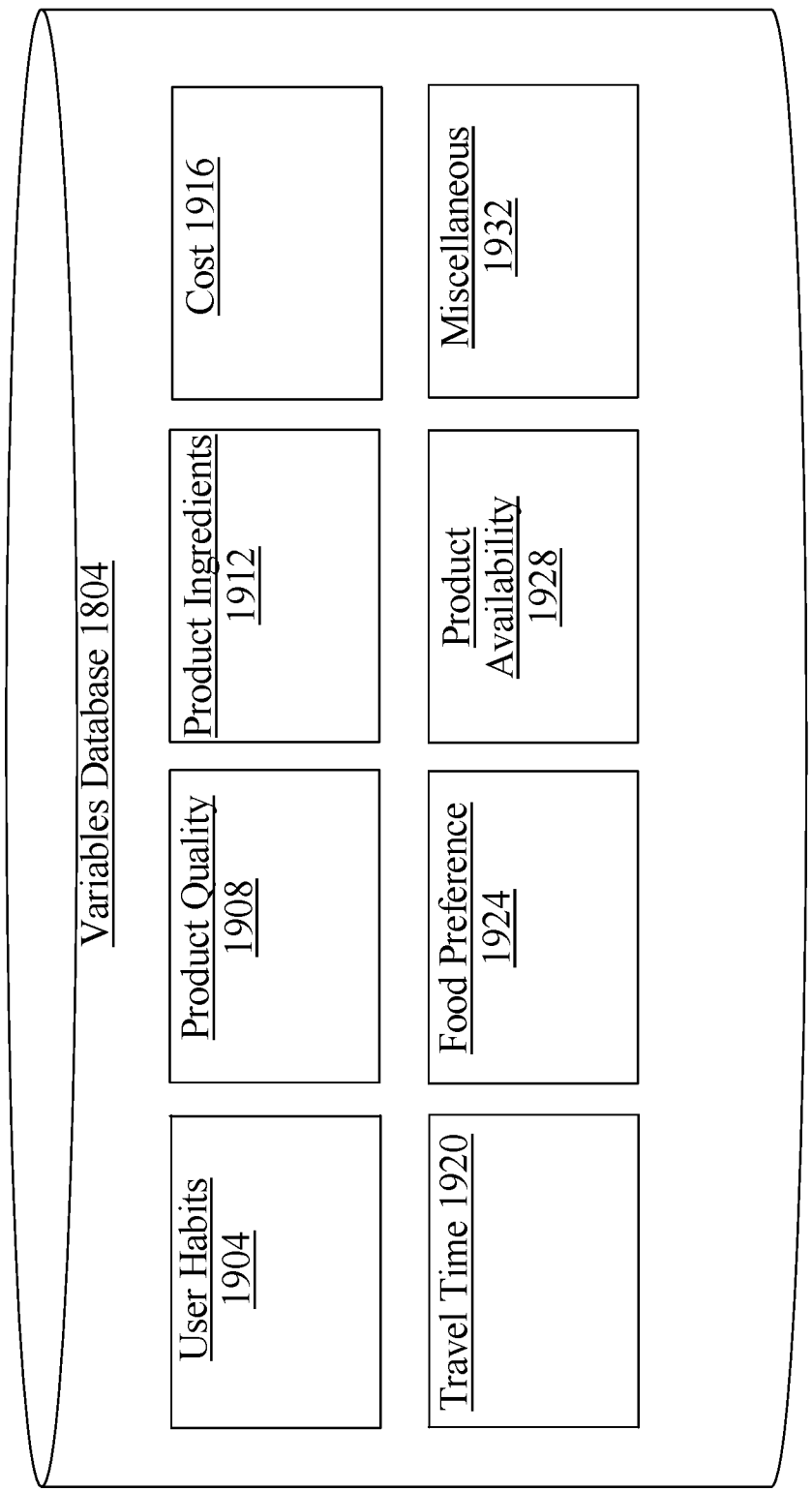
FIG. 19 is a block diagram illustrating an exemplary embodiment of a variables database.

Referring now to FIG. 19, an exemplary embodiment of variables database 1804 is illustrated. Variables database 1804 may be implemented as any database and/or datastore suitable for use as described above. One or more database tables in variables database 1804 may include, without limitation, a user habits table 1904; user habits may contain information pertaining to ways in which a user self-fulfills such as a preference for eating out at restaurants, shopping for groceries, ordering meal kits, cooking at home, having a chef prepare meals, and the like. One or more database tables in variables database 1804 may include without limitation, a product quality table; product quality may contain information relating to quality of food that a user typically consumes, such as a preference for organic produce, wild raised seafood, sustainably grown meats, free range poultry, locally sourced products and/or ingredients, products grown without the use of pesticides and the like. One or more database tables in variables database 1804 may include without limitation, a product ingredients table 1912; product ingredients may include information pertaining to if a certain food or item fulfills an alimentary instruction set. For example, a product such as kale, milk, and spinach may be categorized as containing calcium to aid a user in consuming more calcium rich foods while ingredients such as coconut oil and macaroons may be categorized as containing lauric acid. One or more database tables in variables database 1804 may include without limitation, cost table 1916; cost may include information relating to user cost preference; cost preference may include user preference for eating out at restaurants versus cooking at home, buying groceries at a store versus cost to have groceries delivered, cost for organic versus inorganic products, cost for buying groceries as compared to having meals delivered, user budget for nutrition and supplements, and the like. One or more database tables in variables database 1804 may include without limitation, travel time table 1920; travel time may include information relating to how far a user is willing to travel for nutrition such as for example the miles or minutes a user will drive in a car to a restaurant or grocery store. One or more database tables in variables database 1804 may include without limitation, food preference table 1924; food preferences may include a user's preference to consume certain foods or food groups, such as for example a user's preference to consume chicken and beef but a dislike of plant proteins such as tofu and lentils. One or more database tables in variables database 1804 may include without limitation, product availability table 1928; product availability may include information as to whether certain products, foods, meals, supplements and the like are available in certain geographical locations. For example, fish tacos may be available in Anchorage, Alaska but not in Little Rock, Arkansas, as hazelnuts may be bountiful in the Pacific Northwest but scarce in Anchorage, Alaska. One or more database tables in variables database 1804 may include without limitation, miscellaneous table 1932; miscellaneous may include other variables that may be utilized but have not been discussed above.

Referring back now to FIG. 18, self-fulfillment learner 148 may perform one or more unsupervised machine-learning processes as described above, unsupervised processes may be performed by an unsupervised learning module 908 executing on diagnostic engine 104 and/or on another computing device in communication with diagnostic engine 104, which may include any hardware or software module. For instance and without limitation, self-fulfillment learner 148 may perform an unsupervised machine learning process on second training set 116, which may cluster data of second training set 116 according to detected relationships between elements of the second training set 116, including for example relationships between user entries and alimentary instruction sets and/or self-fulfillment instruction sets; such information may then be combined with supervised machine learning results to add new criteria for self-fulfillment learning 148 to apply in relating between user entries and alimentary instruction sets and/or self-fulfillment instruction sets.

With continued reference to FIG. 18, self-fulfillment learner 148 may be configured to perform a lazy learning process as a function of first training set 106 and/or second training set 116 to examine relationships between user entries and alimentary instruction sets and/or self-fulfillment instruction sets. Lazy learning process may include any lazy learning process as described above regarding prognostic label learner 126. Lazy learning processes may be performed by a lazy learning module 912 operating on diagnostic engine 104 and/or on another computing device in communication with diagnostic engine 104, which may include any hardware or software module.

Figure 20:
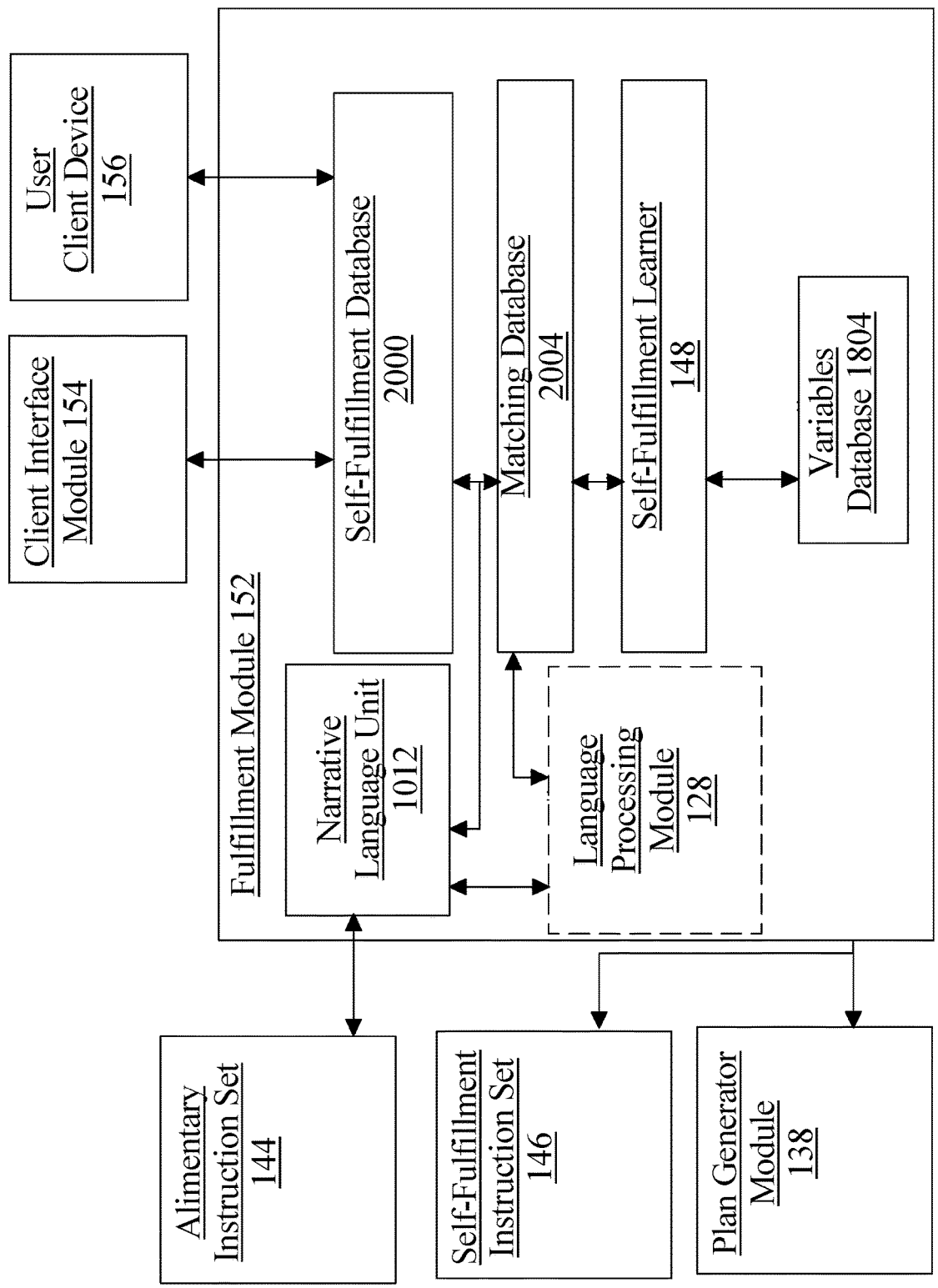
FIG. 20 is a block diagram illustrating an exemplary embodiment of a fulfillment module and associated system elements.

Referring now to FIG. 20, an exemplary embodiment of fulfillment module 152 is illustrated. Fulfillment module 152 may be designed and configured to receive a user entry containing an alimentary self-fulfillment action. Fulfillment module 152 may receive a user entry containing an alimentary self-fulfillment action from user client device 156 and/or through client interface module 154. Self-fulfillment action may include a description, photograph, selection, choice, and the like describing an action a user engaged in to self-fulfill alimentary instruction set 144. Action may include any steps, effort, and/or tasks that a user engage in to self-fulfill alimentary instruction set. Action may include for example, making a grocery list, shopping for supplements, preparing a meal kit, grabbing take out at a restaurant, purchasing a take away meal at a grocery store or meal delivery kitchen and the like. In an embodiment, self-fulfillment action may include an action as recommended by self-fulfillment instruction set and/or be related to an action as recommended by self-fulfillment instruction set. For example, self-fulfillment instruction set may recommend an action such as cooking a recipe containing wild salmon and broccoli rabe. Self-fulfillment action may include an action user took such as purchasing wild salmon at a grocery store or ordering a takeout meal that contained wild salmon and broccoli rabe.

With continued reference to FIG. 20, fulfillment module 152 may contain self-fulfillment database 2000. Self-fulfillment database 2000 may contain different database tables as described below in more detail in FIG. 21, that user entry containing an alimentary self-fulfillment action may be matched with to discover how user's behaviors are contributing to or hurting a user's vibrant constitution by affecting prognostic label and/or ameliorative process label. For example, a user with a prognostic label such as Lyme Disease may receive an ameliorative process label that recommends eating a grain free diet to reduce inflammation and reduce bacterial burden in user's body. User entries describing self-fulfillment actions over a period of time may then be matched against database tables located within self-fulfillment database 2000 to examine how user's actions have contributed to grain free diet, vibrant constitution, health goals, and/or nutrient density scores.

With continued reference to FIG. 20, fulfillment module 152 may contain matching database 2004. Matching database 2004 may include different database tables as described below in more detail in FIG. 22. User entries containing alimentary self-fulfillment action may be matched utilizing matching database 20004 and/or self-fulfillment database 2000. User entries may be received by fulfillment module 152 as either textual entries such as a description of what a user consumed or purchased, graphical entries such as an upload of a meal user ate at a restaurant, and/or by user selection whereby user may select some type of self-fulfillment action from a predetermined list or chart. In an embodiment, user may select a self-fulfillment action from a list, such as one containing actions and/or recommendations from self-fulfillment instruction set. For example, self-fulfillment instruction set may contain a list of 3 options such as a new recipe user could cook, a recommended meal a user could consume, or a grocery store where a user could purchase groceries at. User may then select which of those 3 options user performed if any. In an embodiment, user may provide comments or edit selections such as if instead of consuming salmon and broccoli rabe as recommended by self-fulfillment instruction set 146, user instead consumed salmon and spinach. User entry may then be matched against a table contained within self-fulfillment database 2000 to examine how user entry may affect user's vibrant constitution. For example, user entry containing repetitive self-fulfillment actions such as consuming fried foods may negatively affect user's vibrant constitution. User entry containing a one-time self-fulfillment action of consuming fried food may not have such an impact on one's vibrant constitution. Fulfillment module 152 may utilize matching to compare user entry containing an alimentary self-fulfillment action to at least an alimentary instruction set. For example, an alimentary self-fulfillment action containing a list of meals user consumed in one day may be matched against alimentary instruction set to determine if user consumed recommended nutrients or supplements as provided for by alimentary instruction set. For example, a user entry containing a home cooked meal that contained miso cod over buckwheat with a side salad may be matched against alimentary instruction set to determine if a user entry contains recommended nutrients such as for example an increase in dietary magnesium intake. In yet another non-limiting example, user entry such as a grocery list of purchased groceries from an online grocery store may be matched against alimentary instruction set to determine if user's purchases will fulfill recommended nutrient and dietary recommendations contained within alimentary instruction set. In an embodiment, alimentary instruction set may be modified as a function of user entry. For example, an alimentary instruction set may be updated to contain new nutrients or recommended lower amounts if a user consumes what is recommended and subsequent biological samples reflect restored levels within normal ranges. In yet another non-limiting example, alimentary instruction set may be updated as a function of user entry such as for example, in the winter time when user needs to supplement with higher dosages of vitamin D due to less sun exposure.

With continued reference to FIG. 20, fulfillment module 152 may use machine-learning such as by self-fulfillment learner 148 to utilize user entries in a feedback mechanism to provide subsequent an alimentary instruction set 144, self-fulfillment instruction set 146, and/or provide captured data to plan generator module 138. Fulfillment module 152 may utilize supervised and/or unsupervised machine-learning processes as described above in reference to FIG. 1 and FIG. 18. Fulfillment module 152 mat utilize lazy learning processes as described above in reference to FIG. 1 and FIG. 18.

Figure 21:
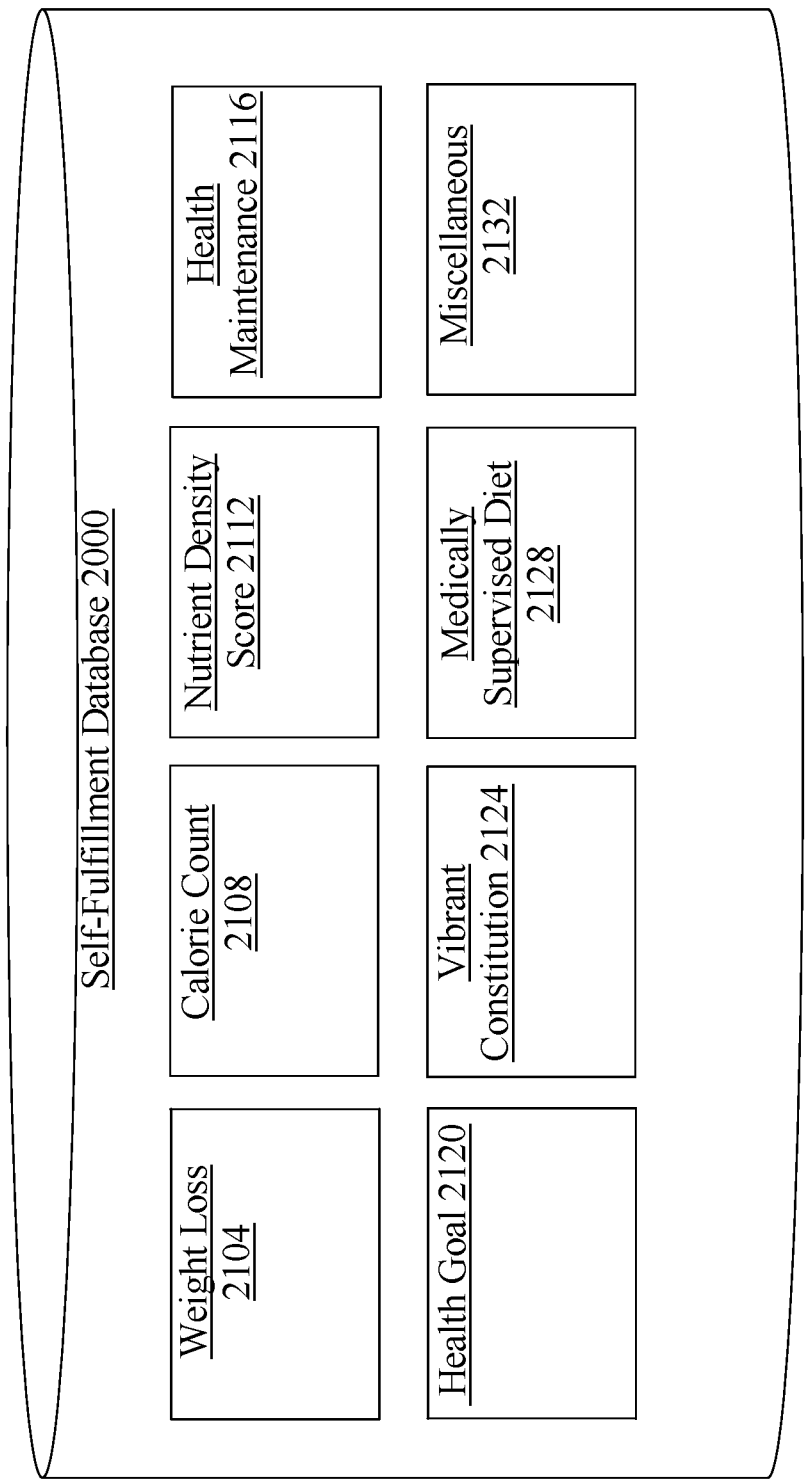
FIG. 21 is a block diagram illustrating an exemplary embodiment of a fulfillment database.

Referring now to FIG. 21, an exemplary embodiment of fulfillment database 2000 is illustrated. Self-fulfillment database 2000 may be implemented as any database and/or datastore suitable for use as described above. Self-fulfillment database 2000 may contain information examining how user's self-fulfillment selections as transmitted to computing device 102 and processed by fulfillment module 152 have affected a user's ability to achieve and/or maintain vibrant constitution. One or more database tables in self-fulfillment database 2000 may include, weight loss table 2104; weight loss may include information describing how user's self-fulfillment options and selections have attributed to weight loss if any over a specific period of time. One or more database tables in self-fulfillment database 2000 may include calorie count table 2108, calorie count may include information describing how user's self-fulfillment options and selections have attributed to certain calorie requirements such as those recommended by an informed advisor. One or more database tables in self-fulfillment database 2000 may include nutrient density score table 2112, nutrient density score may include information describing how user's self-fulfillment options and selections have led to nutrient dense selections such as for example the nutrient density score of consuming a home cooked meal with little oil versus a friend chicken sandwich from a fast food restaurant. One or more database tables in self-fulfillment database 2000 may include health maintenance table 2116, health maintenance may include information describing how user's self-fulfillment options and selections have aided a user in maintaining user's health. User's health may include maintaining a certain status or level of health, such as for example staying free of any diagnosed medical conditions or keeping a disease state such as Ulcerative Colitis in remission without any flares. One or more database tables in self-fulfillment database 2000 may include health goal table 2120, which may include information describing how user's self-fulfillment options and selections helped or hurt a user in achieving a particular health goal. Health goal may include any goal a user may set as it relates to user's health, such as for example, cooking three meals each week at home or ordering low carbohydrate meals at restaurants. One or more database tables in self-fulfillment database 2000 may include vibrant constitution database 2124, which may include information describing how user's self-fulfillment options and selections have attributed or hindered a user in achieving and/or maintaining vibrant constitution. One or more database tables in self-fulfillment database 2000 may include medically supervised diet table 2128, which may include information describing how user's self-fulfillment options and selections have attributed to or hindered a user in adhering to a medically supervised diet. Medically supervised diet may include a diet designed for weight loss such as one prescribed by a functional medicine doctor or functional nutritionist, or a medically supervised diet may include a diet utilized to treat or maintain a medical condition to achieve remission such as a ketogenic diet for epilepsy, a gluten free diet for hypothyroidism or the Wahls protocol for multiple sclerosis. One or more database tables in self-fulfillment database 2000 may include miscellaneous table 2132, which may contain any other information relating a user's self-fulfillment options and selections to achieving vibrant constitutional state.

Figure 22:
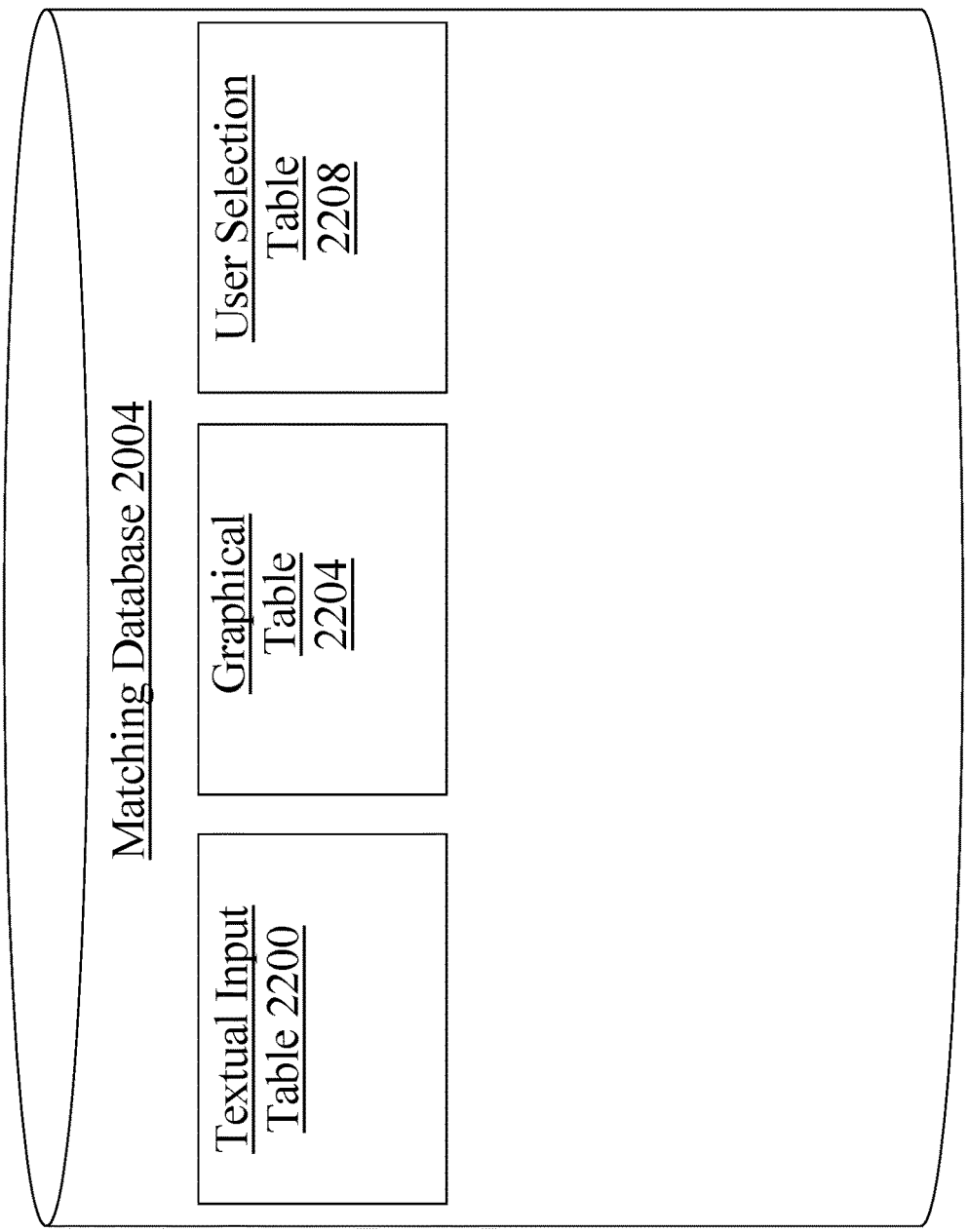
FIG. 22 is a block diagram illustrating an exemplary embodiment of a matching database.

Referring now to FIG. 22, an exemplary embodiment of matching database 2004 is illustrated. Matching database 2004 may be implemented as any database and/or datastore suitable for use as described above. Matching database 2004 may include one or more tables containing one or more categories of user entries that may be matched against information contained within self-fulfillment database 2000 such as by fulfillment module 152. One or more database tables in matching database 2004 may include textual input table 2200, which may include user entries containing text such as a word or string of words, description, or paragraph describing user's alimentary self-fulfillment actions. One or more database tables in matching database 2004 may include graphical table 2204, which may include user entries containing graphics such as pictures, images, and/or graphical representations describing user's alimentary self-fulfillment actions. One or more database tables in matching database 2004 may include user selection table 2208, which may include user entries that a user has selected from a list or drop-down menu.

Figure 23:
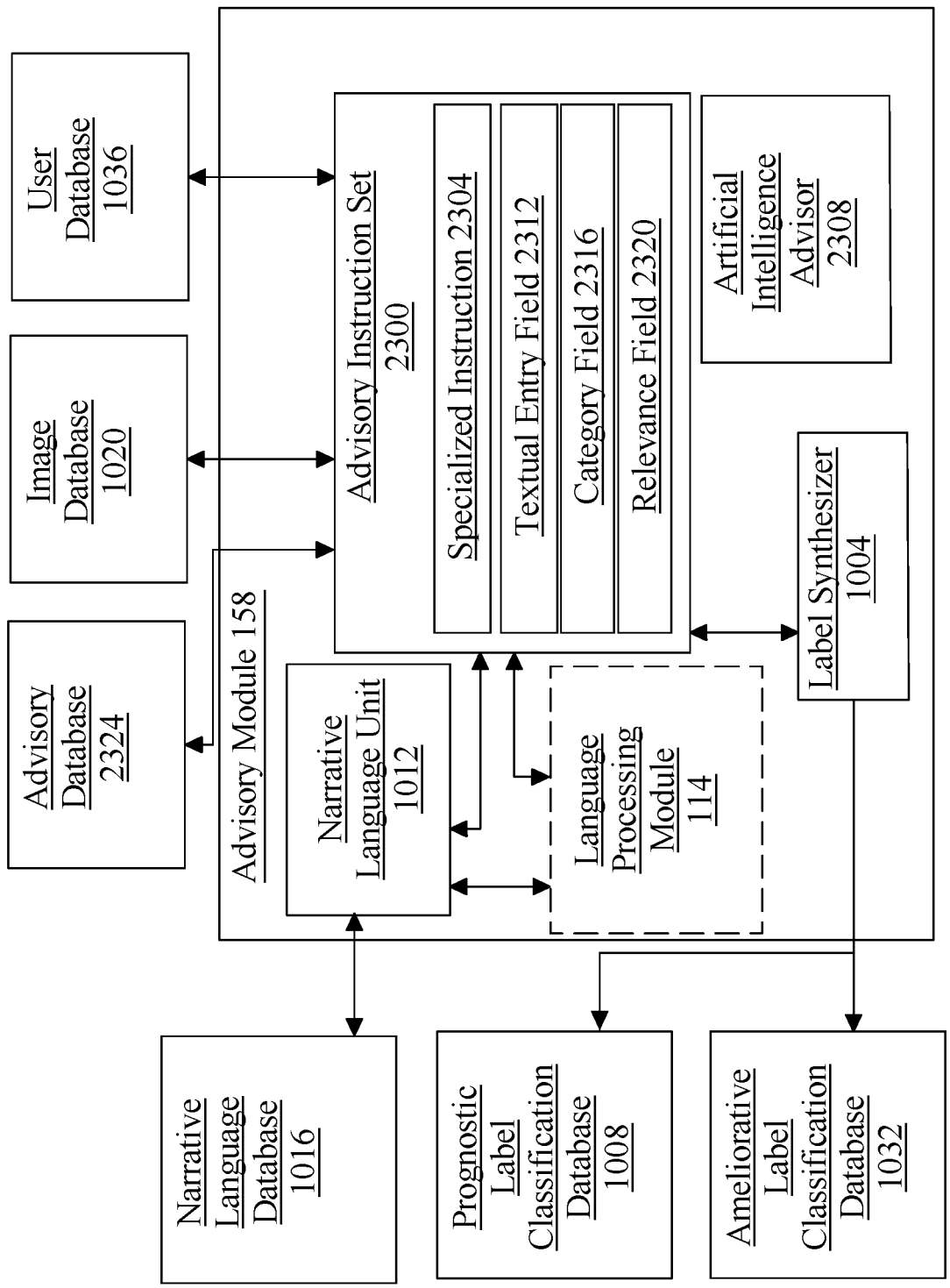
FIG. 23 is a block diagram illustrating an exemplary embodiment of an advisory module and associated system elements.

Referring now to FIG. 23, an exemplary embodiment of an advisory module 158 is illustrated. Advisory module 158 may be configured to generate an advisor instruction set 1600 as a function of the diagnostic output. Advisory instruction set 2300 may contain any element suitable for inclusion in comprehensive instruction set 140; advisory instruction set 2300 and/or any element thereof may be generated using any process suitable for generation of comprehensive instruction set 140. Advisory instruction set 2300 may include one or more specialized instructions 1504; specialized instructions, as used herein, are instructions the contents of which are selected for display to a particular informed advisor. Selection of instructions for a particular informed advisor may be obtained, without limitation, from information concerning the particular informed advisor, which may be retrieved from a user database 1036 or the like. As a non-limiting example, where an informed advisor is a doctor, specialized instruction 2304 may include data from biological extraction as described above; specialized instruction may include one or more medical records of user, which may, as a non-limiting example, be downloaded or otherwise received from an external database containing medical records and/or a database (not shown) operating on a computing device 102. As a further non-limiting example medical data relevant to fitness, such as orthopedic reports, may be provided to an informed advisor whose role is as a fitness instructor, coach, or the like.

In an embodiment, and continuing to refer to FIG. 23, advisory module 158 may be configured to receive at least an advisory input from the advisor client device 160. At least an advisory input may include any information provided by an informed advisor via advisor client device 160. Advisory input may include medical information and/or advice. Advisory input may include user data, including user habits, preferences, religious affiliations, constitutional restrictions, or the like. Advisory input may include spiritual and/or religious advice. Advisory input may include user-specific diagnostic information. Advisory input may be provided to user client device 156; alternatively or additionally, advisory input may be fed back into system 100, including without limitation insertion into user database 1036, inclusion in or use to update diagnostic engine 104, for instance by augmenting machine-learning models and/or modifying machine-learning outputs via a lazy-learning protocol or the like as described above.

With continued reference to FIG. 23, advisory module 158 may include an artificial intelligence advisor 2308 configured to perform a user textual conversation with the user client device 156. Artificial intelligence advisor 2308 may provide output to advisor client device 160 and/or user client device 156. Artificial intelligence advisor 2308 may receive inputs from advisor client device 160 and/or user client device 156. Inputs and/or outputs may be exchanged using messaging services and/or protocols, including without limitation any instant messaging protocols. Persons skilled in the art, up reviewing the entirety of this disclosure, will be aware of a multiplicity of communication protocols that may be employed to exchange text messages as described herein. Text messages may be provided in textual form and/or as audio files using, without limitation, speech-to-text and/or text-to-speech algorithms.

With continued reference to FIG. 23, advisory module 158 may output, with advisory output, a textual entry field 2312. Textual entry field 2312 may include a searchable input field that allows entry of a search term such as a word or phrase to be entered by a user such as an informed advisor. In an embodiment, textual entry field 2312 may allow for entry of a search term to be matched with labels contained within the at least at diagnostic output. For example, an informed advisor such as a medical professional may enter into a search term a results of a fasting glucose test after receiving at least a diagnostic output of diabetes. In such an instance, user such as an informed advisor may be able to search multiple results such as fasting glucose test levels recorded over a certain period of time such as several years and/or months. In yet another non-limiting example, an informed advisor such as a fitness professional may search for user's most recent exercise log and/or nutrition records. In yet another non-limiting example, an informed advisor such as a nurse practitioner may enter information into textual entry field 2312 to search for information pertaining to user's medication history after receiving at least a diagnostic output of acute kidney injury. In an embodiment, textual entry field 2312 may allow a user such as an informed advisor to navigate different areas of advisory output. For example, an informed advisor may utilize textual entry field 2312 to navigate to different locations such as a table of contents, and or sections organized into different categories as described in more detail below.

With continued reference to FIG. 23, advisory module 158 may include in an advisory output a category field 2316. Category field 2316 may include a textual field that contains advisory output organized into categories. Category, as used herein, is any breakdown of advisory output by shared characteristics. Categories may include for example, breakdown by informed advisor type. For example, informed advisors may be categorized into categories of expertise such as spiritual professionals, nutrition professionals, fitness professionals and the like. Categories may include sub-categories of specialties such as for example functional medicine informed advisors may be organized into sub-categories based on body system they may be treating. This could include sub-categories such as dermatology specialists, Genito-urology specialists, gastroenterology specialists, neurology specialists and the like. Categories may include a breakdown by time such as chronological order and/or reverse chronological order. Categories may be modified and/or organized into test results such as for example all complete blood counts that a user has ever had performed may be located in one category, and all CT scans that a user has had performed may be located in another category. Categories may include a breakdown by relevance, such as highly relevant test results and/or test results that are outside normal limits.

With continued reference to FIG. 23, advisory module 158 may include in an advisory output a relevance field 2320. Relevance field 2320 as used herein is a textual field that contains advisory output information labeled as being relevant. Relevance, as used herein, is any information contained within advisory output that is closely connected and/or related to diagnostic output. Relevance may include information that would be of interest to a particular category of informed advisor. For example, an informed advisor such as an ophthalmologist may deem information contained within at least an advisory output such as a measurement of a user's intra-ocular pressure to be of relevance, while an advisory output containing information summarizing a user's last appointment with a podiatrist to not be of relevance. In yet another non-limiting example, an informed advisor such as a fitness professional may deem information contained within an advisory output such as a summary of a user's last appointment with an orthopedic doctor to be relevant while a summary of a user's last colonoscopy may not be relevant. In an embodiment, relevance may be viewed on a continuum. Information contained within at least an advisory output that directly relates to an informed advisor and is of high probative value to an informed advisor may be highly relevant. For example, a nutritionist may deem a journal of a user's eating habits as highly relevant. In yet another non-limiting example, a spiritual professional may deem a summary of a user's church patterns as highly relevant. Information that is related to an informed advisor but does not directly affect an informed advisor may be moderately relevant. For example, a dermatologist may deem information pertaining to a user's last physical exam with an internal medicine doctor to be moderately relevant. In yet another non-limiting example, an endocrinologist may deem information pertaining to a user's last appointment with a podiatrist to be moderately relevant for a user diagnosed with diabetes. Information that is not related to an informed advisor and does not affect an informed advisor may be of low relevance. For example, a trauma surgeon may deem information about a user's last dental cleaning to be of low relevance. In yet another non-limiting example, a cardiologist may deem information about a user's last bone density scan to be of low relevance. In an embodiment, user such as informed advisor may use textual entry field 2312 to navigate advisory output to find information that is relevant. In an embodiment, information contained within at least an advisory output may be marked as relevant such as by another informed advisor. For example, a functional medicine doctor may mark an elevated fasting blood glucose level as relevant before transmitting such a result to a nutrition professional.

In an embodiment, and still referring to FIG. 23, a relevance field 2320 may include an image, link, or other visual element that an informed advisor may select or otherwise interact with to expand or contract a portion of advisory output; for instance, relevance field 2320 may include a symbol next to or on a section heading that can cause a corresponding section of text to display when activated a first time and disappear when activated a second time. As a result, an informed advisor may be presented initially with some text visible and other text not visible; initial presentation may hide all text but section headers. Alternatively or additionally, where informed advisor belongs to a particular category of informed advisor and/or has a profile in, for instance, advisory database 2324 indicating categories of interest to the informed advisor, sections of text and/or images related to such categories may initially display while other sections do not display unless a relevance field 2320 corresponding to such sections is selected by the informed advisor.

With continued reference to FIG. 23, advisory module 158 contains advisory database 2324. Advisory database 2324 may be implemented as any database and/or datastore suitable for use as an advisory database. An exemplary embodiment of an advisory database 2324 is provided below in FIG. 25.

Figure 24:
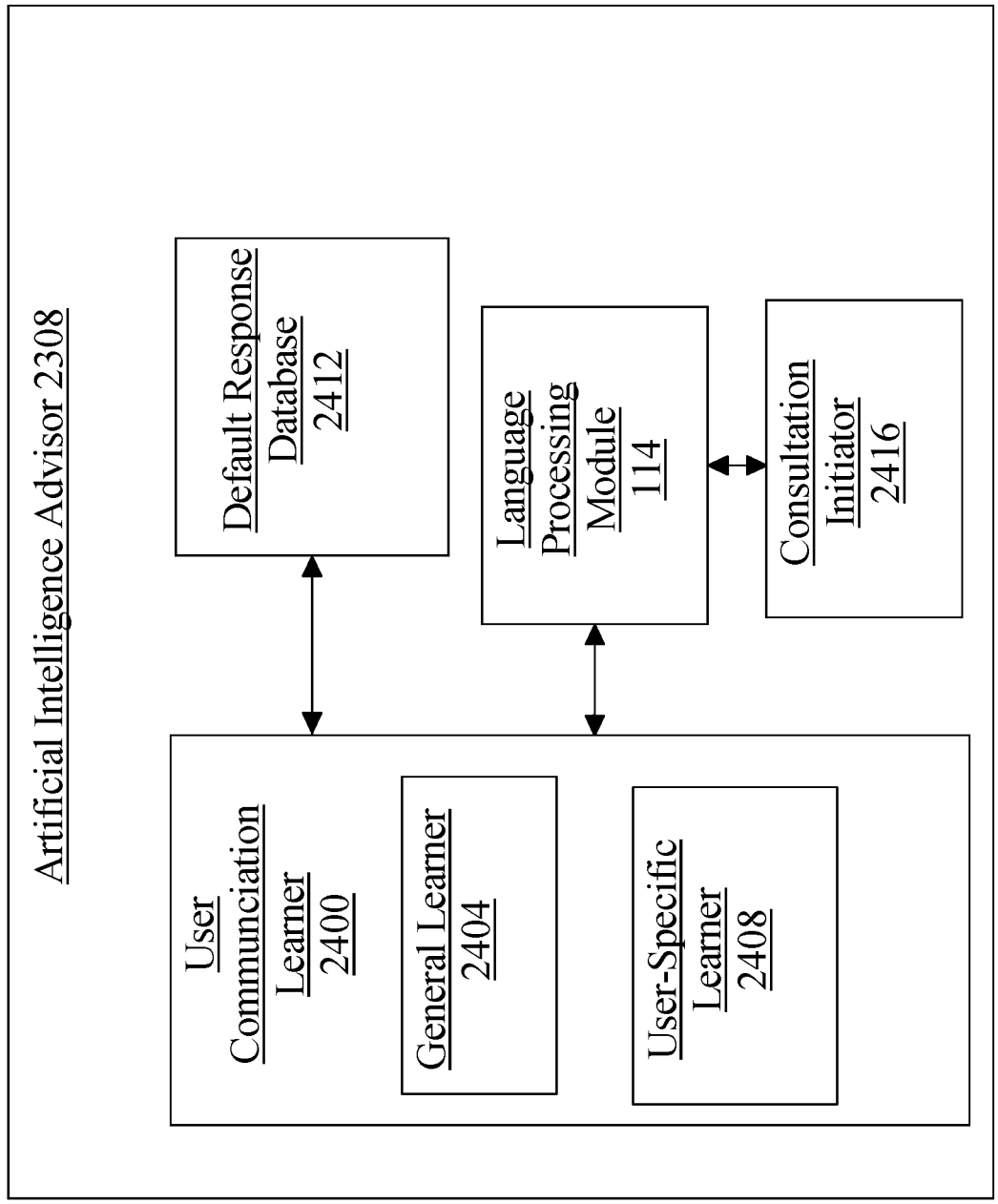
FIG. 24 is a block diagram illustrating an exemplary embodiment of an artificial intelligence advisor and associated system elements.

Referring now to FIG. 24, an exemplary embodiment of an artificial intelligence advisor 2308 is illustrated. Artificial intelligence advisor 2308 may include a user communication learner 2400. User communication learner 2400 may be any form of machine-learning learner as described above, implementing any form of language processing and/or machine learning. In an embodiment, user communication learner 2400 may include a general learner 2404; general learner 2404 may be a learner that derives relationships between user inputs and correct outputs using a training set that includes, without limitation, a corpus of previous conversations. Corpus of previous conversations may be logged by a computing device 102 as conversations take place; user feedback, and/or one or more functions indicating degree of success of a conversation may be used to differentiate between positive input-output pairs to use for training and negative input-output pairs not to use for training. Outputs may include textual strings and/or outputs from any databases, modules, and/or learners as described in this disclosure, including without limitation prognostic labels, prognostic descriptors, ameliorative labels, ameliorative descriptors, user information, or the like; for instance, general learner 2404 may determine that some inputs optimally map to textual response outputs, while other inputs map to outputs created by retrieval of module and/or database outputs, such as retrieval of prognostic descriptors, ameliorative descriptors, or the like. User communication learner may include a user-specific learner 2408, which may generate one or more modules that learn input-output pairs pertaining to communication with a particular user; a user specific learner 1708 may initially use input-output pairs established by general learner 2404 and may modify such pairs to match optimal conversation with the particular user by iteratively minimizing an error function.

Still referring to FIG. 24, general learner 2404 and/or user-specific learner 2408 may initialize, prior to training, using one or more record retrieved from a default response database 2412. Default response database 2412 may link inputs to outputs according to initial relationships entered by users, including without limitation experts as described above, and/or as created by a previous instance or version of general learner 2404 and/or user-specific learner 2408. Default response database 2412 may periodically be updated with information from newly generated instances of general learner 2404 and/or user-specific learner 2408. Inputs received by artificial intelligence advisor 2308 may be mapped to canonical and/or representative inputs by synonym detection as performed, for instance, by a language processing module 114; language processing module 114 may be involved in textual analysis and/or generation of text at any other point in machine-learning and/or communication processes undergone by artificial intelligence advisor 2308.

Figure 25:
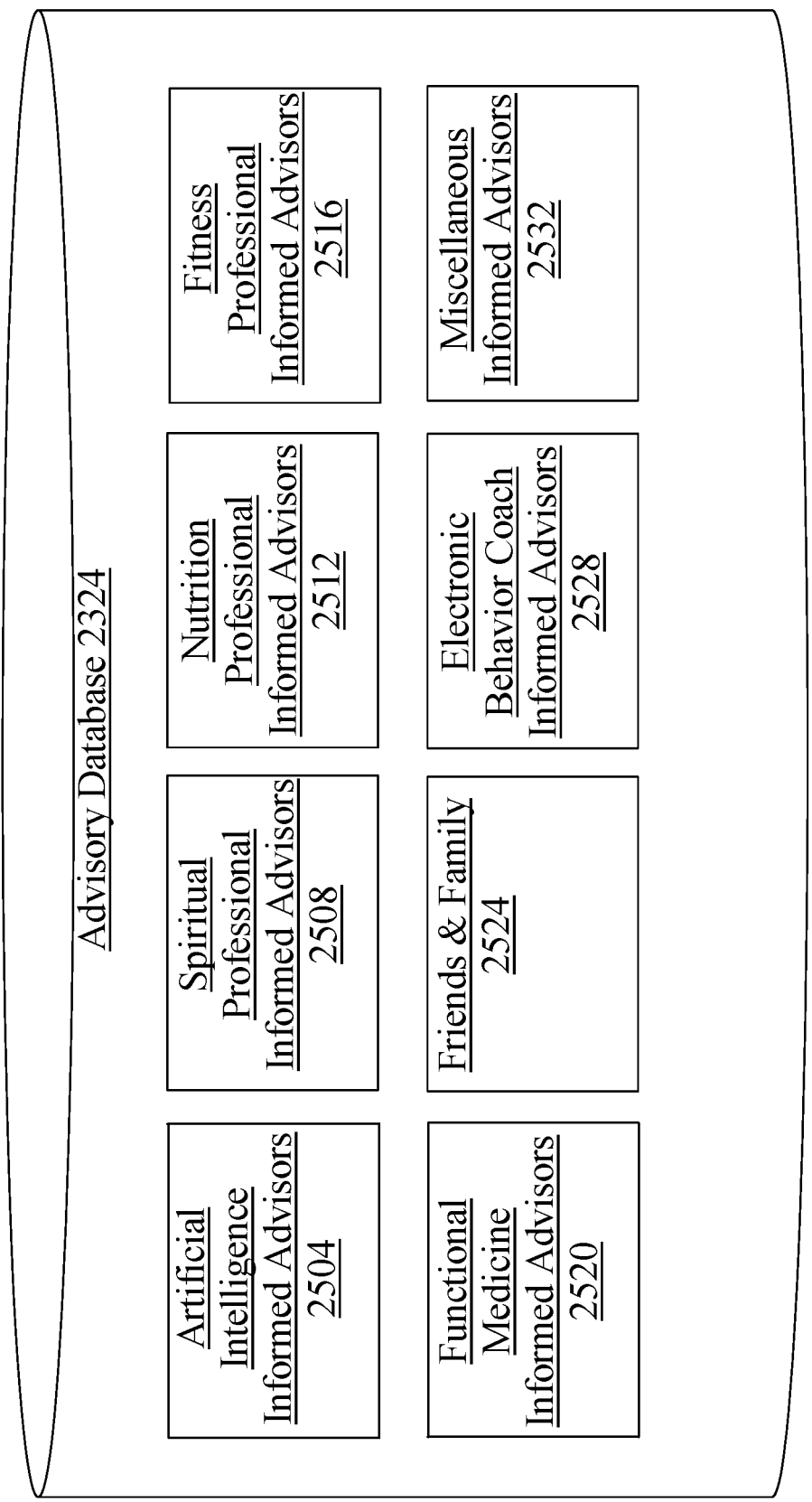
FIG. 25 is a block diagram illustrating an exemplary embodiment of an advisory database.

Referring now to FIG. 25, an exemplary embodiment of advisory database 2324 is illustrated. One or more database tables in advisory database 2324 may link to data surrounding an informed advisor. Advisory database 2324 may include one or more database tables categorized by expertise of informed advisor. One or more database tables in advisory database 2324 may include, without limitation, an artificial intelligence informed advisors table 2504, which may contain any and all information pertaining to artificial intelligence informed advisors. One or more database tables in advisory database 2324 may include, without limitation, a spiritual professional informed advisors table 2508, which may contain any and all information pertaining to spiritual professional informed advisors. Spiritual professional informed advisors may include spiritual professionals who may participate in cultivating spirituality through exercise of practices such as prayer, meditation, breath work, energy work, and the like. One or more database tables in advisory database 2324 may include, without limitation, a nutrition professional informed advisors table 2512, which may include any and all information pertaining to nutritional informed advisors. Nutritional informed advisors may include dietitians, chefs, and nutritionists who may offer expertise around a user's diet and nutrition state and supplementation. One or more database tables in advisory database 2324 may include, without limitation a fitness professional informed advisors table 2516, which may include any and all information pertaining to fitness professional informed advisors. Fitness professional informed advisors may examine the fitness state of a user and may include personal trainers, coaches, group exercise instructors, and the like. One or more database tables in advisory database 2324 may include, without limitation a functional medicine informed advisors table 2520, which may include any and all information pertaining to functional medicine informed advisors. Functional medicine informed advisors may include doctors, nurses, physician assistants, nurse practitioners and other members of the health care team. One or more database tables in advisory database 2324 may include, without limitation a friends and family informed advisors table 2524, which may include any and all information pertaining to friends and family informed advisors. Friends and family informed advisors may include friends and family members of a user who may create a positive community of support for a user. One or more database tables in advisory database 2324 may include, without limitation an electronic behavior coach informed advisor table 2528, which may include any and all information pertaining to electronic behavior coach informed advisors. Electronic behavior coach informed advisors may assist a user in achieving certain results such as modifying behaviors to achieve a result such as assisting in addition recovery and/or changing a user's eating habits to lose weight. One or more database tables in advisory database 2324 may include without limitation a miscellaneous informed advisor table 2532, which may include any and all information pertaining to miscellaneous informed advisors. Miscellaneous informed advisors may include any informed advisors who do not fit into one of the categories such as for example insurance coverage informed advisors. Miscellaneous informed advisor table 2532 may also contain miscellaneous information pertaining to informed advisors such as a user's preference for informed advisors in a certain geographical location and/or other preferences for informed advisors.

Figure 26:
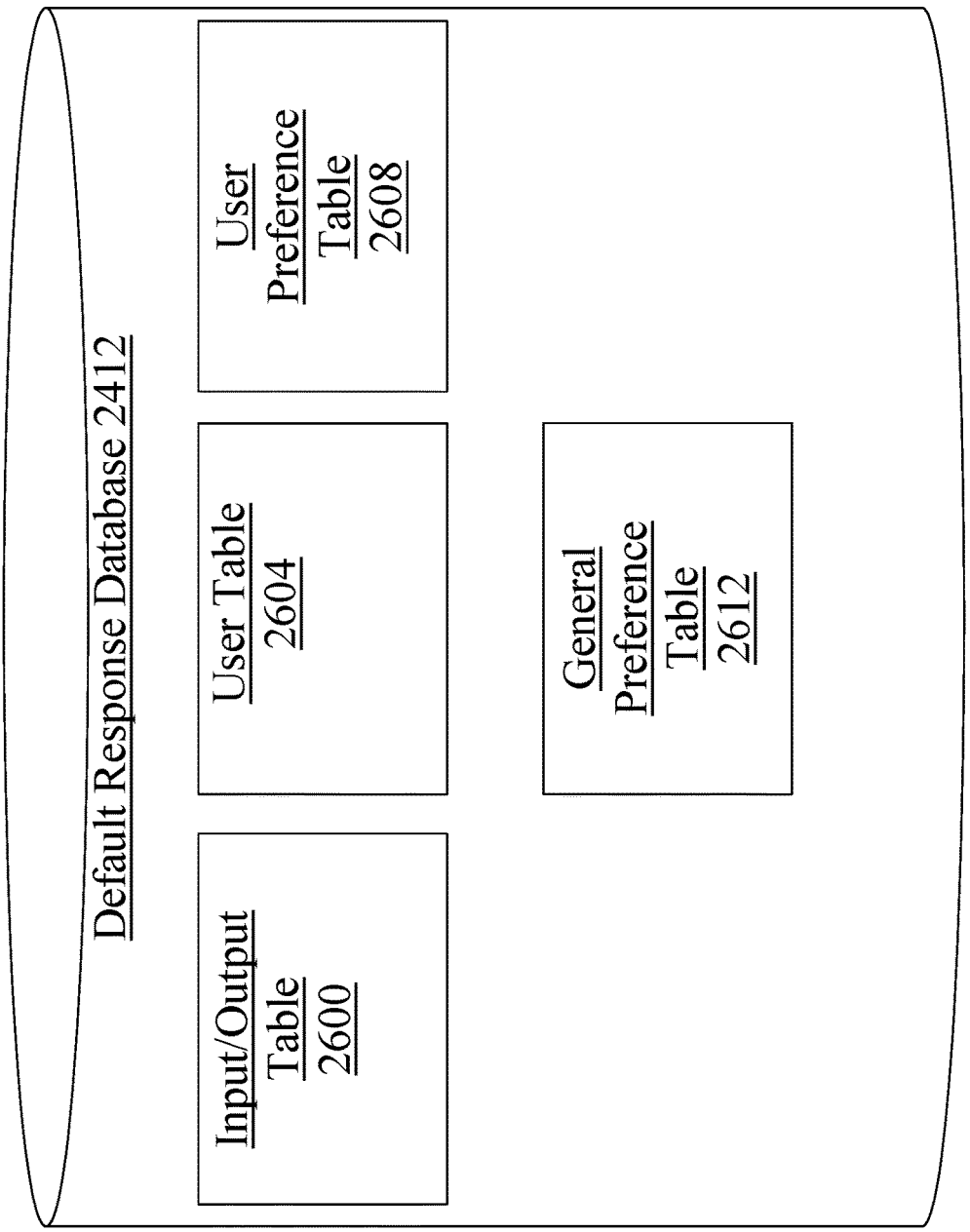
FIG. 26 is a block diagram illustrating an exemplary embodiment of a default response database.

Referring now to FIG. 26, an exemplary embodiment of a default response database 2412 is illustrated. Default response database 2412 may be implemented as any database and/or datastore suitable for use as described above. One or more database tables in default response database 2412 may include, without limitation, an input/output table 2600, which may link default inputs to default outputs. Default response database 2412 may include a user table 2604, which may, for instance, map users and/or a user client device 180 to particular user-specific learners and/or past conversations. Default response database 2412 may include a user preference table 2608 listing preferred modes of address, turns of phrase, or other user-specific communication preferences. Default response database 2412 may include a general preference table 2612, which may track, for instance, output-input pairings associated with greater degrees of user satisfaction.

Referring again to FIG. 24, artificial intelligence advisor may include a consultation initiator 2416 configured to detect a consultation event in a user textual conversation and initiate a consultation with an informed advisor as a function of the consultation event. A consultation event, as used herein, is a situation where an informed advisor is needed to address a user's situation or concerns, such as when a user should be consulting with a doctor regarding an apparent medical emergency or new condition, or with an advisor who can lend emotional support when particularly distraught. Detection may be performed, without limitation, by matching an input and/or set of inputs to an output that constitutes an action of initiating a consultation; such a pairing of an input and/or input set may be learned using a machine learning process, for instance via general learner and/or user specific learner 2408. In the latter case, information concerning a particular user's physical or emotional needs or condition may be a part of the training set used to generate the input/input set to consultation event pairing; for instance, a user with a history of heart disease may trigger consultation events upon any inputs describing shortness of breath, chest discomfort, arrhythmia, or the like. Initiation of consultation may include transmitting a message to an advisor client device 160 associated with an appropriate informed advisor, such as without limitation transmission of information regarding a potential medical emergency to a doctor able to assist in treating the emergency. Initiation of consultation may alternatively or additionally include providing an output to the user informing the user that a consultation with an informed advisor, who may be specified by name or role, is advisable.

Figure 27:
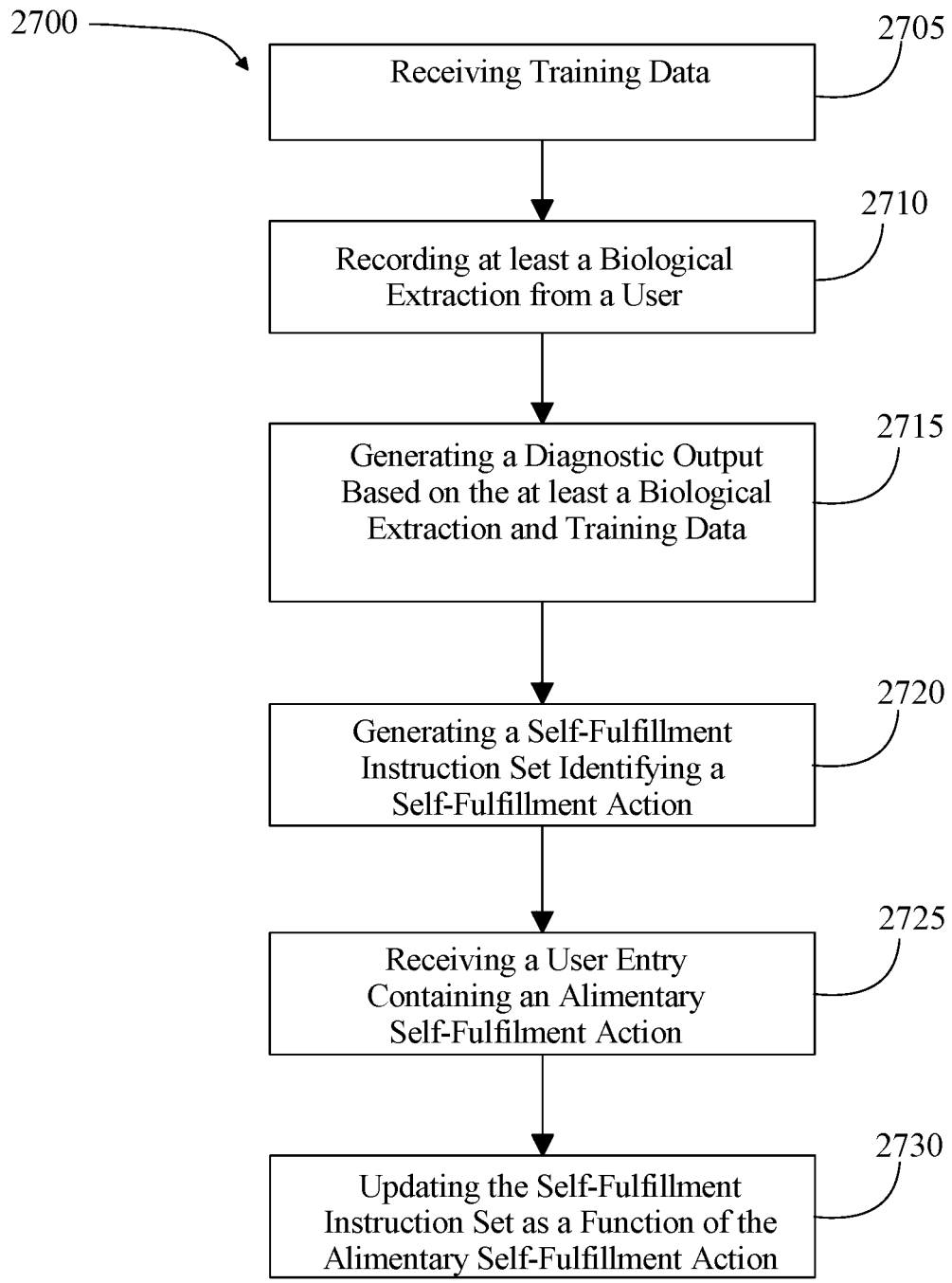
FIG. 27 is a flow diagram illustrating an exemplary embodiment of a method of self-fulfillment of an alimentary instruction set based on vibrant constitutional guidance.

Referring now to FIG. 27, an exemplary embodiment of method of self-fulfillment of an alimentary instruction set based on vibrant constitutional guidance 2700 is illustrated. At step 2705 at least a server receives training data. Receiving training data includes receiving a first training set including a plurality of first data entries, each first data entry of the plurality of first data entries including at least an element of physiological state data and at least a correlated first prognostic label. Receiving training data includes receiving a second training set including a plurality of second data entries, each second data entry of the plurality of second data entries including at least a second prognostic label and at least a correlated ameliorative process label. Receiving training data may be performed by any of the methodologies a described in FIGS. 1-27. Training data may include any of the training data as described in FIGS. 1-27.

With continued reference to FIG. 27, at step 2710, a computing device records at least a biological extraction from a user. Biological extraction may include any of the biological extractions as described above in FIGS. 1-27. Recording biological extraction may be performed by any of the methodologies as described above in FIGS. 1027.

With continued reference to FIG. 27, at step 2715 a computing device generates a diagnostic output based on the at least a biological extraction and training data. Generating diagnostic output may include performing at least a machine-learning algorithm as a function of the training data and the at least a biological extraction. Machine-learning algorithm may include any of the machine-learning algorithms as described above in reference to FIGS. 1027.

With continued reference to FIG. 27, a computing device generates a comprehensive instruction set associated with the user as a function of the diagnostic output. Comprehensive instruction set may include any of the comprehensive instruction sets as described above in reference to FIGS. 1-27 and may include follow-up suggestions, contextual information, future prognostic descriptor, and/or alimentary plan descriptor. Comprehensive instruction set may be generated utilizing any of the methodologies as described above in reference to FIG. 1-27.

With continued reference to FIG. 27, a computing device generates an alimentary instruction set associated with the user as a function of the comprehensive instruction set. Alimentary instruction set may be generated upon receiving at least a datum of user data including a constitutional restriction. Constitutional restriction may include any of the constitutional restrictions as described above in reference to FIGS. 1-27. Alimentary instruction set may be generated upon receiving at least a datum of user data such as a user preference. In an embodiment, alimentary instruction set may be transmitted to a user. This may be done for example, by transmitting alimentary instruction set to user client device 156. In an embodiment, self-fulfillment instruction set may be generated utilizing a loss function of user specific variables and minimizing the loss function. This may be done on a variable by variable basis. In an embodiment, after a user has implemented one step of the self-fulfillment instruction set, the loss function may be re-run to update the self-fulfillment instruction set. In an embodiment, the self-fulfillment instruction set may be generated as a function of user geolocation. In an embodiment, self-fulfillment instruction set may be transmitted to a user. Self-fulfillment instruction set may include any of the self-fulfillment instruction sets as described above in reference to FIGS. 1-27.

With continued reference to FIG. 27, at step 2715, a computing device 102 generates a self-fulfillment instruction set identifying a self-fulfillment action. Self-fulfillment instruction set includes any of the self-fulfillment instruction sets as described above in more detail. Self-fulfillment instruction set is generated utilizing any of the methodologies as described above in more detail. Computing device 102 generates self-fulfillment instruction set utilizing a fulfillment machine-learning model. Computing device 102 receives user training data containing previous user alimentary instruction sets and a plurality of correlated self-fulfillment instruction sets. Computing device 102 generates a self-fulfillment instruction set utilizing user training data and fulfillment machine-learning model. Fulfillment machine-learning model includes any of the machine-learning models as described above in more detail. Computing device 102 generates a self-fulfillment instruction set based on a user geolocation. Computing device 102 may generate a self-fulfillment instruction set to identify a self-fulfillment action located with a user geolocation. For instance and without limitation, computing device 102 may generate a self-fulfillment instruction set to identify a self-fulfillment action located within a user geolocation. For example, for a user with a geolocation in Miami, Fla., computing device 102 may generate a self-fulfillment instruction set that contains a list of groceries that can be purchased online and shipped to the user in Miami Florida. In yet another non-limiting example, for a user with a geolocation in Denver Colorado, computing device 102 may generate a self-fulfillment instruction set that contains a meal a user can order from a restaurant located in Denver Colorado.

With continued reference to FIG. 27, at step 2725 a computing device receives a user entry containing an alimentary self-fulfillment action. Alimentary self-fulfillment action may include any of the alimentary self-fulfillment actions as described above in reference to FIGS. 1-27. Reception of self-fulfillment action may be utilized to track a user location and match alimentary instruction sets and/or self-fulfillment instruction sets to a user. For example, if a user decides to take action regarding a self-fulfillment instruction set such as following directions to a specific grocery store, then user entry may be analyzed and matched to inquire if user actually purchased items relating to alimentary instruction set. In an embodiment, a user may pull up a screen that may allow a user to enter purchased ingredients or scan barcodes pertaining to specific ingredients. Alimentary self-fulfillment action may be received using any of the methodologies as described herein. In an embodiment, user entry containing alimentary self-fulfillment action may be matched by fulfillment module 152. Matching may include any of the matching methodologies as described above in reference to FIGS. 20-22. Matching may include matching a user entry containing an alimentary self-fulfillment action to at least an alimentary instruction set and/or to at least a self-fulfillment instruction set. In an embodiment, self-fulfillment action may include textual entries, graphics such as photographs, and/or user selection from a drop-down menu and may be received using any methodologies as described herein. In an embodiment, alimentary instruction set may be modified as a function of user entry. For example, an alimentary instruction set that recommends a user to increase intake of iodine rich foods such as kelp and seaweed for a sluggish thyroid may be modified after a user has entered user entries that contain consumption of such foods. In yet another non-limiting example, alimentary instruction set that recommends a user to increase intake of iron rich foods for a user with anemia may be updated to recommend consumption of iron rich foods with vitamin c foods to better increase absorption of iron if iron levels do not increase after user entries contain descriptions of foods and/or meals consumed that contain iron rich ingredients. In yet another non-limiting example, alimentary instruction set may be modified once user's blood stores of iron are replete.

With continued reference to FIG. 27, computing device 102 is configured to receive a user entry containing a photograph of a self-fulfillment action. Computing device 102 may receive a wireless transmission from a user client device, containing a photograph of a self-fulfillment action. For example, computing device 102 may receive a photograph of a meal a user ordered from a restaurant or a photograph of produce user purchased at a farm stand. In an embodiment, a photograph may include receipt data. Receipt data includes any of the receipt data as described above. For example, receipt data may include a receipt of an electronic grocery order or a receipt of a meal delivery service. Computing device 102 may classify a photograph of a self-fulfillment action to a self-fulfillment activity category label utilizing self-fulfillment classifier as described above in more detail. For example, computing device 102 may classify a photograph of a grocery receipt purchased at a food store to a self-fulfillment activity category label that indicates in store grocery shopping. In yet another non-limiting example, computing device 102 may classify a photograph of a meal delivery kit to a self-fulfillment activity category label that indicates home cook. Computing device 102 updates a self-fulfillment instruction set utilizing a self-fulfillment activity category label. For instance and without limitation, a photograph categorized to in store grocery shopping may be utilized to generate a self-fulfillment instruction set that contains a self-fulfillment activity for subsequent in store grocery shopping. In yet another non-limiting example, a photograph categorized to restaurant ordering may be utilized to generate a self-fulfillment instruction set that contains subsequent menu ordering and suggested meal options.

With continued reference to FIG. 27, at step 2730 computing device 102 updates a self-fulfillment instruction set utilizing a self-fulfillment action. Computing device 102 updates a self-fulfillment instruction set utilizing any of the methods as described herein. Computing device 102 may update a self-fulfillment instruction set utilizing user input. Computing device 102 receives a user input from a user client device containing a variable related to fulfillment. Computing device 102 may receive a user input utilizing any network methodology as described herein. Computing device 102 generates a loss function utilizing a user input and minimizes the loss function. This may be performed utilizing any of the methodology as described above. Computing device 102 may update a self-fulfillment action utilizing a biological extraction that indicates user digestibility. Computing device 102 records a second biological extraction containing an element of user physiological data containing an indication of user digestibility. An indication of user digestibility includes any of the indicators as described above in more detail in reference to FIG. 1. Computing device 102 updates a self-fulfillment instruction set utilizing an indication of user digestibility. For instance and without limitation, an indication of user digestibility that indicates a user has low intracellular levels of Vitamin C may be utilized by computing device 102 to update a self-fulfillment instruction set to recommend self-fulfillment actions that contain high amounts of Vitamin C. In yet another non-limiting example, an indication of user digestibility that indicates a user has low blood levels of iron may be utilized by computing device 102 to update a self-fulfillment instruction set to recommend self-fulfillment actions that contain slow cooked meats and fulfillment actions that With continued reference to FIG. 1, computing device 102 is configured to evaluate a nourishment allotment of a completed alimentary self-fulfillment action and update a self-fulfillment instruction set utilizing a nourishment outcome. A nourishment allotment, as used in this disclosure, is data describing any nutritional content of any food item. A nutritional content may indicate if a food item is a vegetable or fruit, or if a food item contains nutrients such as iron or fiber. A nutritional content may indicate if a food item is something that has a negative effect on a human body such as fried foods or foods high in added sugars. A nutritional content may indicate if a food item is something that has a positive effect on a human body such as cruciferous vegetables or foods high in monounsaturated fats such as avocado, almond, or peanuts. For example, a nourishment allotment for a meal a user purchased at a restaurant may indicate that the meal contained wild salmon high in protein and omega three fatty acids, and broccoli sautéed in avocado oil and high in Vitamin K, potassium, and indole 3 carbinol. Computing device 102 may compare a nourishment allotment of a completed alimentary self-fulfillment action to a nourishment requirement contained within an alimentary instruction set. A nourishment requirement, as used in this disclosure, is data describing nutritional needs of a user. A nourishment requirement may be generated based on a user's alimentary instruction set. For instance and without limitation, a nourishment requirement may indicate that a user has high blood sugar and needs to consume a Mediterranean diet. In yet another non-limiting example, a nourishment requirement may indicate that a user has anemia and needs to consume twenty five milligrams per day of iron. Computing device 102 compares a nourishment allotment to a nourishment requirement to determine a nourishment outcome. A nourishment outcome, as used in this disclosure, is data describing any nutritional status of a user. A nutritional status may indicate if a user has completed a user's nourishment requirement and if user needs an updated nourishment allotment. For example, computing device 102 may determine that a user with hypothyroidism has not consumed enough iodine from food sources based on a user's nourishment allotment as compared to a user's nourishment requirement to consume 500 micrograms per day of iodine. In such an instance, computing device 102 may determine a nourishment outcome that indicates the user needs to consume additional iodine. Computing device 102 may update a self-fulfillment instruction set to account for the additional iodine and may recommend self-fulfillment actions that contain groceries, meals, and/or food items that contain additional iodine.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 28:
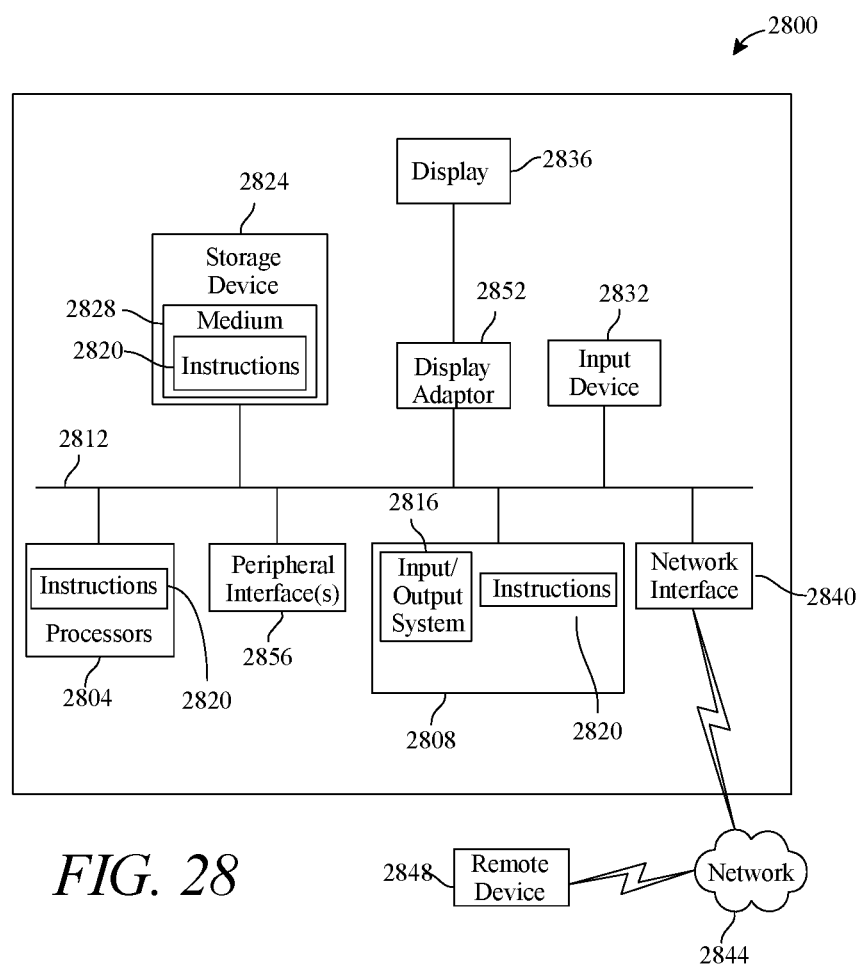
FIG. 28 is a block diagram of a computing system that can be used to implement any one or more of the methodologies disclosed herein and any one or more portions thereof.

FIG. 28 shows a diagrammatic representation of one embodiment of a computing device in the exemplary form of a computer system 2800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2800 includes a processor 2804 and a memory 2808 that communicate with each other, and with other components, via a bus 2812. Bus 2812 may include any of several types of bus structures including, but not limited to, a memory bus, a memory controller, a peripheral bus, a local bus, and any combinations thereof, using any of a variety of bus architectures.

Memory 2808 may include various components (e.g., machine-readable media) including, but not limited to, a random-access memory component, a read only component, and any combinations thereof. In one example, a basic input/output system 2816 (BIOS), including basic routines that help to transfer information between elements within computer system 2800, such as during start-up, may be stored in memory 2808. Memory 2808 may also include (e.g., stored on one or more machine-readable media) instructions (e.g., software) 2820 embodying any one or more of the aspects and/or methodologies of the present disclosure. In another example, memory 2808 may further include any number of program modules including, but not limited to, an operating system, one or more application programs, other program modules, program data, and any combinations thereof.

Computer system 2800 may also include a storage device 2824. Examples of a storage device (e.g., storage device 2824) include, but are not limited to, a hard disk drive, a magnetic disk drive, an optical disc drive in combination with an optical medium, a solid-state memory device, and any combinations thereof. Storage device 2824 may be connected to bus 2812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2824 (or one or more components thereof) may be removably interfaced with computer system 2800 (e.g., via an external port connector (not shown)). Particularly, storage device 2824 and an associated machine-readable medium 2828 may provide nonvolatile and/or volatile storage of machine-readable instructions, data structures, program modules, and/or other data for computer system 2800. In one example, software 2820 may reside, completely or partially, within machine-readable medium 2828. In another example, software 2820 may reside, completely or partially, within processor 2804.

Computer system 2800 may also include an input device 2832. In one example, a user of computer system 2800 may enter commands and/or other information into computer system 2800 via input device 2832. Examples of an input device 2832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2832 may be interfaced to bus 2812 via any of a variety of interfaces (not shown) including, but not limited to, a serial interface, a parallel interface, a game port, a USB interface, a FIREWIRE interface, a direct interface to bus 2812, and any combinations thereof. Input device 2832 may include a touch screen interface that may be a part of or separate from display 2836, discussed further below. Input device 2832 may be utilized as a user selection device for selecting one or more graphical representations in a graphical interface as described above.

A user may also input commands and/or other information to computer system 2800 via storage device 2824 (e.g., a removable disk drive, a flash drive, etc.) and/or network interface device 2840. A network interface device, such as network interface device 2840, may be utilized for connecting computer system 2800 to one or more of a variety of networks, such as network 2844, and one or more remote devices 2848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2844, may employ a wired and/or a wireless mode of communication. In general, any network topology may be used. Information (e.g., data, software 2820, etc.) may be communicated to and/or from computer system 2800 via network interface device 2840.

Computer system 2800 may further include a video display adapter 2852 for communicating a displayable image to a display device, such as display device 2836. Examples of a display device include, but are not limited to, a liquid crystal display (LCD), a cathode ray tube (CRT), a plasma display, a light emitting diode (LED) display, and any combinations thereof. Display adapter 2852 and display device 2836 may be utilized in combination with processor 2804 to provide graphical representations of aspects of the present disclosure. In addition to a display device, computer system 2800 may include one or more other peripheral output devices including, but not limited to, an audio speaker, a printer, and any combinations thereof. Such peripheral output devices may be connected to bus 2812 via a peripheral interface 2856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for self-fulfillment of an alimentary instruction set based on vibrant constitutional guidance, the system comprising:
   a computing device;
   a diagnostic engine operating on the computing device, the diagnostic engine configured to:
      receive training data, wherein receiving the training data further comprises:
         receiving a first training set including a plurality of first data entries, each first data entry of the plurality of first data entries including at least an element of physiological state data and at least a correlated first prognostic label; and
         receiving a second training set including a plurality of second data entries, each second data entry of the plurality of second data entries including at least a second prognostic label and at least a correlated ameliorative process label;
      record at least a biological extraction from a user wherein the at least a biological extraction contains at least an element of physiological state data; and
      generate a diagnostic output based on the at least a biological extraction and the training data, wherein generating further comprises performing at least a machine-learning algorithm as a function of the training data and the at least a biological extraction; and
   a fulfillment module operating on the at least a server the fulfillment module designed and configured to:
      generate a self-fulfillment instruction set utilizing the diagnostic output wherein the self-fulfillment instruction set identifies a self-fulfillment action;
      receive at least a user entry containing a completed alimentary self-fulfillment action;
      update the self-fulfillment instruction set as a function of the alimentary self-fulfillment action;
      record at least a second biological extraction wherein the second biological extraction contains an element of user physiological data containing an indication as to user digestibility; and
      update the self-fulfillment instruction set utilizing the indication as to user digestibility.

2. The system of claim 1, wherein the computing device further comprises:
   a plan generator module operating on the computing device, the plan generator module configured to generate a comprehensive instruction set associated with the user as a function of the diagnostic output; and
   an alimentary instruction set generator module operating on the computing device, the alimentary instruction set generator module designed and configured to generate at least an alimentary instruction set as a function of the comprehensive instruction set.

3. The system of claim 1, wherein the fulfillment module is further configured to:
   receive user training data, wherein user training data further comprises a plurality of previous user entries containing previous user alimentary instruction sets, and a plurality of correlated self-fulfillment instruction sets; and
   generate a self-fulfillment instruction set utilizing the user training data and a first machine-learning model.

4. The system of claim 1, wherein the fulfillment module is further configured to:
- receive from a user client device, an element of data describing a user geolocation; and
- generate the self-fulfillment instruction set to identify a self-fulfillment action located within the user geolocation.

5. The system of claim 1, wherein the fulfillment module further is further configured to receive, at an image capture device, located on the computing device, a wireless transmission from a user client device, containing a photograph of a self-fulfillment action.

6. The system of claim 5, wherein the fulfillment module is further configured to:
- input, the user entry containing the photograph of the self-fulfillment action, to a self-fulfillment classifier, the self-fulfillment classifier configured to input the photograph of the self-fulfillment action and output a self-fulfillment activity category label; and
- update the self-fulfillment instruction set utilizing the self-fulfillment activity category label.

7. The system of claim 5, wherein the photograph of the self-fulfillment action further comprises receipt data.

8. The system of claim 1, wherein the fulfillment module is further configured to:
- compare a nourishment allotment of the completed alimentary self-fulfillment action to a nourishment requirement contained within an alimentary instruction set to determine a nourishment outcome; and
- update the self-fulfillment instruction set utilizing the nourishment outcome.

9. The system of claim 1, wherein the fulfillment module is further configured to:
- receive a user input from a user client device, wherein the user input contains a variable preference related to fulfillment;
- generate a loss function utilizing the user input; and
- minimize the loss function.

10. A method of self-fulfillment of an alimentary instruction set based on vibrant constitutional guidance, the method comprising:
- receiving by a computing device training data, wherein receiving the training data further comprises:
  - receiving a first training set including a plurality of first data entries, each first data entry of the plurality of first data entries including at least an element of physiological state data and at least a correlated first prognostic label; and
  - receiving a second training set including a plurality of second data entries, each second data entry of the plurality of second data entries including at least a second prognostic label and at least a correlated ameliorative process label;
- recording by the computing device at least a biological extraction from a user wherein the at least a biological extraction contains at least an element of physiological state data;
- generating by the computing device a diagnostic output based on the at least a biological extraction and the training data, wherein generating further comprises performing at least a machine-learning algorithm as a function of the training data and the at least a biological extraction;
- generating by the computing device a self-fulfillment instruction set utilizing the diagnostic output wherein the self-fulfillment instruction set identifies a self-fulfillment action;
- receiving by the computing device at least a user entry containing a completed alimentary self-fulfillment action;
- updating by the computing device the self-fulfillment instruction set as a function of the alimentary self-fulfillment action, wherein updating the self-fulfillment instruction set further comprises:
  - recording at least a second biological extraction wherein the second biological extraction contains an element of user physiological data containing an indication as to user digestibility; and
  - updating the self-fulfillment instruction set utilizing the indication as to user digestibility.

11. The method of claim 10, wherein generating the diagnostic output further comprises:
- generating a comprehensive instruction set associated with the user as a function of the diagnostic output; and
- generating at least an alimentary instruction set as a function of the comprehensive instruction set.

12. The method of claim 10, wherein generating the self-fulfillment instruction set further comprises:
- receiving user training data, wherein user training data further comprises a plurality of previous user entries containing previous user alimentary instruction sets, and a plurality of correlated self-fulfillment instruction sets; and
- generating a self-fulfillment instruction set utilizing the user training data and a first machine-learning model.

13. The method of claim 10, wherein generating the self-fulfillment instruction set further comprises:
- receiving from a user client device an element of data describing a user geolocation; and
- generating the self-fulfillment instruction set to identify a self-fulfillment action located within the user geolocation.

14. The method of claim 10, wherein receiving the at least a user entry further comprises receiving at an image capture device, located on the computing device, a wireless transmission from a user client device, containing a photograph of a self-fulfillment action.

15. The method of claim 14 further comprising:
- inputting, the user entry containing the photograph of the self-fulfillment action, to a self-fulfillment classifier, the self-fulfillment classifier configured to input the photograph of the self-fulfillment action and output a self-fulfillment activity category label; and
- updating the self-fulfillment instruction set utilizing the self-fulfillment activity category label.

16. The method of claim 14, wherein receiving the photograph of the self-fulfillment action further comprises receiving receipt data.

17. The method of claim 10, wherein updating the self-fulfillment instruction set further comprises:
- comparing a nourishment allotment of the completed alimentary self-fulfillment action to a nourishment requirement contained within an alimentary instruction set to determine a nourishment outcome; and
- updating the self-fulfillment instruction set utilizing the nourishment outcome.

18. The method of claim 10, wherein updating the self-fulfillment instruction set further comprises:
- receiving a user input from a user client device, wherein the user input contains a variable preference related to fulfillment;
- generating a loss function utilizing the user input; and
- minimizing the loss function.

* * * * *